US008557290B2

(12) United States Patent
Wu et al.

(10) Patent No.: US 8,557,290 B2
(45) Date of Patent: Oct. 15, 2013

(54) MULTIFUNCTION NANOCONJUGATES FOR IMAGING APPLICATIONS AND TARGETED TREATMENT

(75) Inventors: Ai-Guo Wu, Chicago, IL (US); Tatjana Paunesku, Chicago, IL (US); Gayle E. Woloschak, Chicago, IL (US)

(73) Assignee: Northwestern University, Evanston, IL (US)

( * ) Notice: Subject to any disclaimer, the term of this patent is extended or adjusted under 35 U.S.C. 154(b) by 601 days.

(21) Appl. No.: 12/403,970

(22) Filed: Mar. 13, 2009

(65) Prior Publication Data

US 2009/0263331 A1 Oct. 22, 2009

Related U.S. Application Data

(60) Provisional application No. 61/036,628, filed on Mar. 14, 2008.

(51) Int. Cl.

| | |
|---|---|
| ***A61K 9/14*** | (2006.01) |
| ***A61K 49/04*** | (2006.01) |
| ***A61K 49/06*** | (2006.01) |
| ***C01F 17/00*** | (2006.01) |
| ***C01G 49/02*** | (2006.01) |
| ***C01G 23/047*** | (2006.01) |
| *A61K 47/48* | (2006.01) |

(52) U.S. Cl.

CPC . *A61K 9/14* (2013.01); *C01F 17/00* (2013.01); *A61K 47/48076* (2013.01); *A61K 47/48315* (2013.01); *C01G 49/02* (2013.01); *C01G 23/047* (2013.01); *Y10S 977/773* (2013.01); *Y10S 977/838* (2013.01); *Y10S 977/904* (2013.01); *Y10S 977/911* (2013.01); *Y10S 977/927* (2013.01); *Y10S 977/928* (2013.01); *Y10S 977/93* (2013.01)

USPC ..................... 424/489; 252/62.59; 424/9.323; 424/9.42; 424/9.6; 424/646; 423/610; 977/773; 977/838; 977/904; 977/911; 977/927; 977/928; 977/930

(58) Field of Classification Search

None

See application file for complete search history.

(56) References Cited

U.S. PATENT DOCUMENTS

| | | | | |
|---|---|---|---|---|
| 6,540,981 | B2 | 4/2003 | Klaveness | |
| 6,677,606 | B1 | 1/2004 | Rajh | |
| 7,412,279 | B2 | 8/2008 | Weisskoff | |
| 2005/0130167 | A1 * | 6/2005 | Bao et al. | 435/6 |

OTHER PUBLICATIONS

CT Chen, YC Chen. "Fe3O4/TiO2 Core/Shell Nanoparticles as Affinity Probes for the Analysis of Phosphopeptides Using TiO2 Surface-Assisted Laser Desorption/Ionization Mass Spectrometry." Anal. Chem., vol. 77, 2005, pp. 5912-5919.*

BL Oliva, A Pradhan, D Caruntu, CJ O'Connor, MA Tarr. "Formation of gold-coated magnetic nanoparticles using TiO2 as a bridging material." Journal of Materials Research, vol. 21, No. 5, May 2006, pp. 1312-1316.*

D Zhu, RD White, PA Hardy, N Weerapreeyakul, K Sutthanut, M Jay. "Biocompatible Nanotemplate-Engineered Nanoparticles Containing Gadolinium: Stability and Relaxivity of a Potential MRI Contrast Agent." Journal of Nanoscience and Nanotechnology, vol. 6, 2006, pp. 996-1003.*

Smolina et al., "End invasion of peptide nucleic acids (PNAs) with mixed-base composition into linear DNA duplexes." Nucleic Acids Research, 2005, vol. 33, No. 17, e146 (9 pgs.).

Sparrow et al., "Involvement of oxidative mechanisms in blue-light-induced damage to A2E-laden RPE." Investigative Ophthalmology & Visual Science, Apr. 2002, vol. 43, No. 4, pp. 1222-1227.

Sugden et al., "Oxidative activation of the human carcinogen chromate by arsenite: a model for synergistic metal activation leading to oxidative DNA damage." Toxicology In Vitro, 2004, vol. 18, pp. 741-748.

Sugden, "Photochemistry of dyes and fluorochromes used in biology and medicine: some physicochemical background and current applications." Biotechnic & Histochemistry, 2004, vol. 79(2), pp. 71-90.

Summerton James E.; "Morpholinos and PNAs Compared"; in Peptide Nucleic Acids, Morpholinos, and Related Antisense Biomolecules, During, C.G.J.A.M.K. Ed. Springer US 2006 pp. 89-96.

Thurn et al., "Nanoparticles for Applications in Cellular Imaging" Nanoscale Research Letters, (2007), 2, pp. 430-441.

Tom et al., "Mechanism whereby proliferating cell nuclear antigen stimulates flap endonuclease 1." The Journal of Biological Chemistry, Apr. 7 2000, vol. 275, No. 14, pp. 10498-10505.

Wang et al.; "Knockdown of c-Myc expression by RNAi inhibits MCF-7 breast tumor cells growth in vitro and in vivo"; Breast Cancer Research, 2005, 7(2) R220-228.

Wang et al., "Controlled Assembly of Monolayer-Protected Gold Clusters by Dissolved DNA" Nano Letters, 2004, vol. 4, No. 1, pp. 95-101.

Weinstein et al., "Mechanisms of disease: Oncogene addiction—a rationale for molecular targeting in cancer therapy." Nature Clinical Practice Oncology, Aug. 2006, vol. 3, No. 8, pp. 448-457.

Whittemore et al., "A detailed analysis of hydrogen peroxide-induced cell death in primary neuronal culture." Neuroscience, 1995, vol. 67, No. 4, pp. 921-932.

Wittung et al., "Interactions of DNA binding ligands with PNA-DNA hybrids." Nucleic Acids Research, 1994, vol. 22, No. 24, pp. 5371-5377.

Armitage et al., "Peptide nucleic acid-anthraquinone conjugates: strand invasion and photoinduced cleavage of duplex DNA." Nucleic Acids Research, 1997, vol. 25, No. 2, pp. 4674-4678.

Arsac et al.,"DNA damage photoinduced by titanium dioxide in the presence of anionic vesicles under uv illumination: influence of sodium chloride concentration." Journal of Oleo Science, 2007, vol. 56(11), pp. 595-601.

(Continued)

*Primary Examiner* — Frederick Krass
*Assistant Examiner* — Isaac Shomer
(74) *Attorney, Agent, or Firm* — Casimir Jones, S.C.; Tanya A. Arenson

(57) ABSTRACT

The present invention relates to nanoconjugates. In particular, the present invention provides nanoconjugates for diagnostic (e.g., imaging), research, and clinical (e.g., targeted treatment) applications.

20 Claims, 55 Drawing Sheets

(56) References Cited

OTHER PUBLICATIONS

Ashikaga et al., "Effect of the photocatalytic activity of TiO(2) on plasmid DNA." Mutation Research, 2000, vol. 466, pp. 1-7.
Betts et al., "A nucleic acid triple helix formed by a peptide nucleic acid-DNA complex." Science, Dec. 15, 1995, vol. 270, pp. 1838-1841.
Braasch et al., "Synthesis, analysis, purification, and intracellular delivery of peptide nucleic acids." Methods 2001 vol. 23 pp. 97-107.
Braun et al., "A biological transporter for the delivery of peptide nucleic acids (PNAs) to the nuclear compartment of living cells." J. Mol. Biol. 2002 vol. 318 pp. 237-243.
Brown et al., "Methods for assessing DNA hybridization of peptide nucleic acid-titanium dioxide nanoconjugates." Analytical Biochemistry, 2008, vol. 383, pp. 226-235.
Brown et al., "NMR solution structure of a peptide nucleic acid complexed with RNA." Science , Aug. 5, 1994,vol. 265, pp. 777-780.
Cao et al., "DNA-Modified Core-Shell Ag/Au Nanoparticles" J. Am. Soc. 2001 123 pp. 7961-7962.
Celis et al., "Cell cycle-dependent variations in the distribution of the nuclear protein cyclin proliferating cell nuclear antigen in cultured cells: subdivision of S phase." Proc. Natl. Acad. Sci. USA, vol. 82, May 1985, pp. 3262-3266.
Chin et al., "Essential role for oncogenic Ras in tumour maintenance." Nature, Jul. 29, 1999, vol. 400, pp. 468-472.
Demidov et al., "Stability of peptide nucleic acids in human serum and cellular extracts." Biochemical Pharmacology, Sep. 15, 1994, vol. 48, Issue 6, pp. 1310-1313.
Devaraj et al., "18F labeled nanoparticles for in vivo PET-CT imaging." Bioconjug. Chem., Feb. 18, 2009, vol. 20(2), pp. 397-401.
Endres et al., "DNA-TiO2 nanoconjugates labeled with magnetic resonance contrast agents." J. Am. Chem. Soc. 2007 vol. 129 pp. 15760-15761.
Eriksson et al., "Solution structure of a peptide nucleic acid-DNA duplex." Nature Structural Biology, May 1996, vol. 3, No. 5, pp. 410-413.
Felsher, "Cancer revoked: oncogenes as therapeutic targets." Nature Reviews/Cancer, May 2003, vol. 3(5), pp. 375-380.
Hamilton et al., "Specific and Nonspecific Inhibition of Transcription by DNA, PNA, and Phosphorothioate Promoter Analog Duplexes"; Bioorganic & Medicinal Letters, 1996, vol. 6, No. 23, pp. 2897-2900.
Herbert et al., "Inhibition of human telomerase in immortal human cells leads to progressive telomere shortening and cell death." Proc. Natl. Acad. Sci. USA, Dec. 7, 1999, vol. 96, No. 25, pp. 14276-14281.
Jin et al., "What controls the melting properties of DNA-linked gold nanoparticle assemblies?" J. Am. Chem. Soc. 2003 vol. 125 1643-1654.
Shammas et al., "Telomerase inhibition by peptide nucleic acids reverses 'immortality' of transformed human cells." Oncogene 1999 vol. 18 pp. 6191-6200.
Kaihatsu et al., "Extending recognition by peptide nucleic acids (PNAs): binding to duplex DNA and inhibition of transcription by tail-clamp PNA-peptide conjugates." Biochemistry, 2003, vol. 42, pp. 13996-14003.
Kaihatsu et al., "Recognition of chromosomal DNA by PNAs." Chemistry and Biology, Jun. 2004, vol. 11, pp. 749-758.
Karras et al., "Peptide nucleic acids are potent modulators of endogenous pre-mRNA splicing of the murine interleukin-5 receptor-alpha chain." Biochemistry (Mosc.) 2001 vol. 40 pp. 7853-7859.
Laktionov et al., "Characterisation of membrane oligonucleotide-binding proteins and oligonucleotide uptake in keratinocytes." Nucleic Acids Research, 1999, vol. 27, No. 11, pp. 2315-2324.
Lal et al., "Nanoshell-enabled photothermal cancer therapy: impending clinical impact." Accounts of Chemical Research, Dec. 2008, vol. 41, No. 12, pp. 1842-1851.
Liu et al.; "Photocatalytic probing of DNA sequence by using TiO2/dopamine-DNA triads"; Chemical Physics, 2007, 339, pp. 154-163.
Liu et al.; "Photooxidation mechanism of dye alizarin red in TiO2 dispersions under visible illumination: an experimental and theoretical examination"; Journal of Molecular Catalysis A: Chemical, 2000, vol. 153, pp. 221-229.
Liu et al., "Hybrid TiO2 Nanoparticles: An Approach for Developing Site Specific DNA Cleavage" Proc. of SPIE, 2006, vol. 6096, pp. 60960F-1-10.
Lytton-Jean et al., "A thermodynamic investigation into the binding properties of DNA functionalized gold nanoparticle probes and molecular fluorophore probes." J. Am. Chem. Soc. 2005 vol. 127 pp. 12754-12755.
Mayfield et al., "Automated Synthesis of Peptide Nucleic Acids and Peptide Nucleic Acid±Peptide Conjugates" Anal. Biochem. 1999 vol. 286 pp. 401-404.
McMahon et al., "Pharmacokinetics and tissue distribution of a peptide nucleic acid after intravenous administration." Antisense & Nucleic Acid Drug Development, 2002, vol. 12, pp. 65-70.
Michelmore et al., "The interaction of linear polyphosphates with titanium dioxide Surfaces" Phys. Chem. 2000 vol. 2 pp. 2985-2992.
Mirkin et al., "A DNA-based Method for Rationally Assembling Nanoparticles into Macroscopic Materials"; Nature, Aug. 15, 1996, vol. 382, pp. 607-609.
Nestle et al., "Cationic lipid is not required for uptake and selective inhibitory activity of ICAM-1 phosphorothioate antisense oligonucleotides in keratinocytes." J. Invest Dermatol. 1994 103(4) pp. 569-575.
Niedre et al., "Direct near-infrared luminescence detection of singlet oxygen generated by photodynamic therapy in cells in vitro and tissues in vivo." Photochemistry and Photobiology, 2002, vol. 75(4), pp. 382-391.
Nielson et al., "Sequence-Selective Recognition of DNA by Strand Displacement with a Thymine-Substituted Polyamide" Science, Dec. 6, 1991, vol. 254, pp. 1497-1500.
Noonberg et al., "Characteristics of oligonucleotide uptake in human keratinocyte cultures." J. Invest. Dermatol. 1993 101(5) pp. 727-731.
Paunesku et al., "X-ray fluorescence microprobe imaging in biology and medicine." Journal of Cellular Biochemistry, 2006, vol. 99, pp. 1489-1502.
Paunesku et al., "Intracellular distribution of TiO2-DNA oligonucleotide nanoconjugates directed to nucleolus and mitochondria indicates sequence specificity." Nano Letters, 2007, vol. 7, No. 3, pp. 596-601.
Paunesku et al., "Gadolinium-conjugated TiO2-DNA oligonucleotide nanoconjugates show prolonged intracellular retention period and T1-weighted contrast enhancement in magnetic resonance images." Nanomedicine: Nanotechnology, Biology and Medicine; (2008) vol. 4, pp. 201-207.
Paunesku et al., "Biology of TiO2-oligonucleotide nanocomposites." Nature Materials, May 2003, vol. 2, pp. 343-346.
Puchtler et al., "On the History and Mechanism of Alizarin and Alizarin Red S Stains for Calicum"; The Journal of Histochemistry and Cytochemistry, 1969, vol. 17, No. 2, pp. 110-124.
Rajh et al., "Spin polarization mechanisms in early stages of photoinduced charge separation in surface-modified TiO2 naonparticles" Chemical Physics Letters, Aug. 17, 2001, 344, pp. 31-39.
Rajh et al., "Improving Optical and Charge Separation Properties of Nanocrystalline TiO2 by Surface Modification with Vitamin C" J. Phys. Chem. B, 1999, 103(18), pp. 3515-3519.
Rajh et al., "Surface Restructuring of Nanoparticles: An Efficient Route for Ligand-Metal Oxide Crosstalk" J. Phys. Chem. B. 2002, vol. 106, pp. 10543-10552.
Rajh et al., "Charge Transfer Across the Nanocrystalline-DNA Interface: Probing DNA Recognition" Nano Letters. 2004, vol. 4, No. 6, pp. 1017-1023.
Rasmussen et al., "Crystal structure of a peptide nucleic acid (PNA) duplex at 1.7 A resolution." Nature Structural Biology, Feb. 1997, vol. 4, No. 2, pp. 98-101.
Schneider et al., "Multifunctional Cytotoxic Stealth Nanoparticles. A Model Approach with Potential for Cancer Therapy" Nano Letters, 2009, vol. 9, No. 2, pp. 636-642.
Seo et al., "Development of water-soluble single-crystalline TiO2 nanoparticles for photocatalytic cancer-cell treatment." Small 2007 3(5) pp. 850-853.
Zhang et al., "Photocatalytic killing effect of TiO2 nanoparticles on Ls-174-t human colon carcinoma cells." World Journal of Gastroenterology, 2004, 10(21), 3191-3193.

* cited by examiner

Figure 42

SEQ. ID. NO.: 10

PNA Sequence "r18s" 16-mer (N-terminal end) [dopamine - succinic acid linker - TTTCCTTGGATGTGGT ]

SEQ. ID. NO.: 1

Target: pKaede plasmid with R18 sequence as insert has 16-mer full match and three 7-mer full matches (1, 4 and 9 nt from 3' end)

tgatcctcaggtaccggaactgcagcagagaattcaccacatccaaggaaagggaaactcgagaacaaagcttggatcagcggccgcggggaccatggtgagtctgattaaaccagaaatgaagatcaagctg
cttatggaaggcaatgtaaacgggcaccagtttgttattgagggagatggaaaaggccatcctttgagggaaaacagagtatggaccttgtagtcaaagaaggcgcacctctccctttgcctacgatatcttgacaaca
gcattccattatggtaacagggtttttgctaaatacccagaccatataccagactacttcaagcagtcgtttcccaaagggttttcttgggagcgaagcctgatgttcgaggacggggcgtttgcatcgctacaaatgacata
acactgaaaggagacactttttttaacaaagttcgatttgatggcgtaaactttcccccaaatggtcctgttatgcagaagaagactctgaaatgggaggcatccactgagaaaatgtatttgcgtgatggagtgttgacggg
cgatattacaatggctctgctgcttaaaggagatgtccattaccgatgtgacttcagaactacttacaaatctaggcaggagggtgtcaagttgccaggatatcactttgtcgatcactgcatcagcatattgaggcatgaca
aagactacaacgaggttaagctgtatgagcacgctgttgcccattctggattgccggacaacgtcaagtaatctagagggggccgcgactctagatcataatcagccataccacatttgtagaggttttacttgctttaaaa
aacctcccacacctccccctgaacctgaaacataaaatgaatgcaattgttgttgttaacttgtttattgcagcttataatggttacaaataaagcaatagcatcacaaatttcacaaataaagcatttttttcactgcattctagtt
gtggtttgtccaaactcatcaatgtatcttaaggcgtaaattgtaagcgttaatattttgttaaaattcgcgttaaatttttgttaaatcagctcattttttaaccaataggccgaaatcggcaaaatcccttataaatcaaaagaata
gaccgagatagggttgagtgttgttccagtttggaacaagagtccactattaaagaacgtggactccaacgtcaaagggcgaaaaaccgtctatcagggcgatggcccactacgtgaaccatcaccctaatcaagttttttt
ggggtcgaggtgccgtaaagcactaaatcggaaccctaaagggagcccccgatttagagcttgacggggaaagccggcgaacgtggcgagaaaggaagggaagaaagcgaaaggagcgggcgctagggcg
ctggcaagtgtagcggtcacgctgcgcgtaaccaccacacccgccgcgcttaatgcgccgctacagggcgcgtcaggtggcacttttcggggaaatgtgcgcggaacccctatttgtttatttttctaaatacattcaaatat
gtatccgctcatgagacaataaccctgataaatgcttcaataatattgaaaaaggaagagtcctgaggcggaaagaaccagctgtggaatgtgtgtcagttagggtgtggaaagtccccaggctccccagcaggcaga
agtatgcaaagcatgcatctcaattagtcagcaaccaggtgtggaaagtccccaggctccccagcaggcagaagtatgcaaagcatgcatctcaattagtcagcaaccatagtcccgcccctaactccgcccatcccg
cccctaactccgcccagttccgcccattctccgccccatggctgactaattttttttatttatgcagaggccgaggccgcctcggcctctgagctattccagaagtagtgaggaggcttttttggaggcctaggcttttgcaaaga
tcgatcaagagacaggatgaggatcgtttcgcatgattgaacaagatggattgcacgcaggttctccggccgcttgggtggagaggctattcggctatgactgggcacaacagacaatcggctgctctgatgccgccgtg
ttccggctgtcagcgcaggggcgcccggttctttttgtcaagaccgacctgtccggtgccctgaatgaactgcaagacgaggcagcgcggctatcgtggctggccacgacgggcgttccttgcgcagctgtgctcgacg
ttgtcactgaagcgggaagggactggctgctattgggcgaagtgccggggcaggatctcctgtcatctcaccttgctcctgccgagaaagtatccatcatggctgatgcaatgcggcggctgcatacgcttgatccggcta
cctgcccattcgaccaccaagcgaaacatcgcatcgagcgagcacgtactcggatggaagccggtcttgtcgatcaggatgatctggacgaagagcatcaggggctcgcgccagccgaactgttcgccaggctcaa
ggcgagcatgcccgacggcgaggatctcgtcgtgacccatggcgatgcctgcttgccgaatatcatggtggaaaatggccgcttttctggattcatcgactgtggccggctgggtgtggcggaccgctatcaggacatag
cgttggctacccgtgatattgctgaagagcttggcggcgaatgggctgaccgcttcctcgtgctttacggtatcgccgctcccgattcgcagcgcatcgccttctatcgccttcttgacgagttcttctgagcgggactctggggt
tcgaaatgaccgaccaagcgacgcccaacctgccatcacgagatttcgattccaccgccgccttctatgaaaggttgggcttcggaatcgttttccgggacgccggctggatgatcctccagcgcggggatctcatgctg
gagttcttcgcccaccctagggggaggctaactgaaacacggaaggagacaataccggaaggaacccgcgctatgacggcaataaaaagacagaataaaacgcacggtgttgggtcgtttgttcataaacgcggg
gttcggtcccagggctggcactctgtcgataccccaccgagaccccattggggccaatacgcccgcgtttcttccttttccccaccccaccccccaagttcgggtgaaggcccagggctcgcagccaacgtcggggcgg
caggccctgccatagcctcaggttactcatatatactttagattgatttaaaacttcatttttaatttaaaaggatctaggtgaagatcctttttgataatctcatgaccaaaatcccttaacgtgagttttcgttccactgagcgtcag
accccgtagaaaagatcaaaggatcttcttgagatcctttttttctgcgcgtaatctgctgcttgcaaacaaaaaaaccaccgctaccagcggtggtttgtttgccggatcaagagctaccaactctttttccgaaggtaactgg
cttcagcagagcgcagataccaaatactgtccttctagtgtagccgtagttaggccaccacttcaagaactctgtagcaccgcctacatacctcgctctgctaatcctgttaccagtggctgctgccagtggcgataagtcgt
gtcttaccgggttggactcaagacgatagttaccggataaggcgcagcggtcgggctgaacggggggttcgtgcacacagcccagcttggagcgaacgacctacaccgaactgagatacctacagcgtgagctatg
agaaagcgccacgcttcccgaagggagaaaggcggacaggtatccggtaagcggcagggtcggaacaggagagcgcacgagggagcttccagggggaaacgcctggtatctttatagtcctgtcgggtttcgcca
cctctgacttgagcgtcgatttttgtgatgctcgtcaggggggcggagcctatggaaaaacgccagcaacgcggcctttttacggttcctggccttttgctggccttttgctcacatgttctttcctgcgttatcccctgattctgtgg
ataaccgtattaccgccatgcattagttattaatagtaatcaattacggggtcattagttcatagcccatatatggagttccgcgttacataacttacggtaaatggcccgcctggctgaccgcccaacgacccccgcccattg
acgtcaataatgacgtatgttcccatagtaacgccaatagggactttccattgacgtcaatgggtggagtatttacggtaaactgcccacttggcagtacatcaagtgtatcatatgccaagtacgccccctattgacgtcaat
gacggtaaatggcccgcctggcattatgcccagtacatgaccttatgggactttcctacttggcagtacatctacgtattagtcatcgctattaccatggtgatgcggttttggcagtacatcaatgggcgtggatagcggtttga
ctcacggggatttccaagtctccaccccattgacgtcaatgggagtttgttttggcaccaaaatcaacgggactttccaaaatgtcgtaacaactccgccccattgacgcaaatgggcggtaggcgtgtacggtgggaggt
ctatataagcagagctggtttagtgaaccgtcagatccgctagcatt

Figure 43

SEQ. ID. NO.: 18

PNA Sequence "5' line human" 15-mer (N-terminal end) [dopamine - succinic acid linker - AAGATATTCCATGAC ]

SEQ. ID. NO.: 2

Target: pKaede plasmid with R18 sequence as insert has a 10-mer match with a single mismatch (1 nt from 3' end) and three 7-mer full matches (0, 2 and 3 nt distant from 3'end)

ggatcctcaggtaccggaactgcagcagagaattcaccacatccaaggaaagggaaactcgagaacaaagcttggatcagcggccgcggggaccatggtgagtctgattaaaccagaaatgaagatcaagctgct
tatggaaggcaatgtaaacgggcaccagtttgttattgagggagatggaaaaggccatccttttgagggaaaacagagtatggaccttgtagtcaaagaaggcgcacctctcccttttgcctacgatatcttgacaacag
cattccattatggtaacagggtttttgctaaatacccagaccatataccagactacttcaagcagtcgtttcccaaagggttttcttggcagcgaagcctgatgttcgaggacggggggcgtttgcatcgctacaaatgacata
acactgaaaggagacacttttttaacaaagttcgatttgatggcgtaaactttcccccaaatggtcctgttatgcagaagaagactctgaaatgggaggcatccactgagaaaatgtatttgcgtgatggagtgttgacggg
cgatattacaatggctctgctgcttaaaggagatgtccattaccgatgtgacttcagaactacttacaaatctaggcaggagggtgtcaagttgccaggatatcactttgtcgatcactgcatcagcatattgaggcatgaca
aagactacaacgaggttaagctgtatgagcacgctgttgcccattctggattgccggacaacgtcaagtaatctagagggggccgcgactctagatcataatcagccataccacatttgtagaggttttacttgctttaaaaa
acctcccacacctccccctgaacctgaaacataaaatgaatgcaattgttgttgttaacttgtttattgcagcttataatggttacaaataaagcaatagcatcacaaatttcacaaataaagcatttttttcactgcattctagttgt
ggtttgtccaaactcatcaatgtatcttaaggcgtaaattgtaagcgttaatattttgttaaaattcgcgttaaatttttgttaaatcagctcattttttaaccaataggccgaaatcggcaaaatcccttataaatcaaaagaataga
ccgagatagggttgagtgttgttccagtttggaacaagagtccactattaaagaacgtggactccaacgtcaaagggcgaaaaaccgtctatcagggcgatggcccactacgtgaaccatcaccctaatcaagttttttgg
ggtcgaggtgccgtaaagcactaaatcggaaccctaaagggagcccccgatttagagcttgacggggaaagccggcgaacgtggcgagaaaggaagggaagaaagcgaaaggagcgggcgctagggcgctg
gcaagtgtagcggtcacgctgcgcgtaaccaccacacccgccgcgcttaatgcgccgctacagggcgcgtcaggtggcacttttcggggaaatgtgcgcggaacccctatttgtttatttttctaaatacattcaaatatgta
tccgctcatgagacaataaccctgataaatgcttcaataatattgaaaaaggaagagtcctgaggcggaaagaaccagctgtggaatgtgtgtcagttagggtgtggaaagtccccaggctccccagcaggcagaagt
atgcaaagcatgcatctcaattagtcagcaaccaggtgtggaaagtccccaggctccccagcaggcagaagtatgcaaagcatgcatctcaattagtcagcaaccatagtcccgcccctaactccgcccatcccgccc
ctaactccgcccagttccgcccattctccgccccatggctgactaattttttttatttatgcagaggccgaggccgcctcggcctctgagctattccagaagtagtgaggaggcttttttggaggcctaggcttttgcaaagatc
gatcaagagacaggatgaggatcgtttcgcatgattgaacaagatggattgcacgcaggttctccggccgcttgggtggagaggctattcggctatgactgggcacaacagacaatcggctgctctgatgccgccgtgtt
ccggctgtcagcgcaggggcgcccggttctttttgtcaagaccgacctgtccggtgccctgaatgaactgcaagacgaggcagcgcggctatcgtggctggccacgacgggcgttccttgcgcagctgtgctcgacgttg
tcactgaagcgggaagggactggctgctattgggcgaagtgccggggcaggatctcctgtcatctcaccttgctcctgccgagaaagtatccatcatggctgatgcaatgcggcggctgcatacgcttgatccggctacct
gcccattcgaccaccaagcgaaacatcgcatcgagcgagcacgtactcggatggaagccggtcttgtcgatcaggatgatctggacgaagagcatcaggggctcgcgccagccgaactgttcgccaggctcaagg
cgagcatgcccgacggcgaggatctcgtcgtgacccatggcgatgcctgcttgccgaatatcatggtggaaaatggccgcttttctggattcatcgactgtggccggctgggtgtggcggaccgctatcaggacatagcg
ttggctacccgtgatattgctgaagagcttggcggcgaatgggctgaccgcttcctcgtgctttacggtatcgccgctcccgattcgcagcgcatcgccttctatcgccttcttgacgagttcttctgagcgggactctggggttc
gaaatgaccgaccaagcgacgcccaacctgccatcacgagatttcgattccaccgccgccttctatgaaaggttgggcttcggaatcgttttccgggacgccggctggatgatcctccagcgcggggatctcatgctgga
gttcttcgcccaccctagggggaggctaactgaaacacggaaggagacaataccggaaggaacccgcgctatgacggcaataaaaagacagaataaaacgcacggtgttgggtcgtttgttcataaacgcggggtt
cggtcccagggctggcactctgtcgataccccaccgagaccccattggggccaatacgcccgcgtttcttccttttccccaccccaccccccaagttcgggtgaaggcccagggctcgcagccaacgtcggggcggca
ggccctgccatagcctcaggttactcatatatactttagattgatttaaaacttcatttttaatttaaaaggatctaggtgaagatcctttttgataatctcatgaccaaaatcccttaacgtgagttttcgttccactgagcgtcagac
cccgtagaaaagatcaaaggatcttcttgagatcctttttttctgcgcgtaatctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgctctgctaatcctgttaccagtggctgctgccagtggcgataagtcgtgtc
ttaccgggttggactcaagacgatagttaccggataaggcgcagcggtcgggctgaacggggggttcgtgcacacagcccagcttggagcgaacgacctacaccgaactgagatacctacagcgtgagctatgaga
aagcgccacgcttcccgaagggagaaaggcggacaggtatccggtaagcggcagggtcggaacaggagagcgcacgagggagcttccagggggaaacgcctggtatctttatagtcctgtcgggtttcgccacct
ctgacttgagcgtcgatttttgtgatgctcgtcaggggggcggagcctatggaaaaacgccagcaacgcggcctttttacggttcctggccttttgctggccttttgctcacatgttctttcctgcgttatcccctgattctgtggata
accgtattaccgccatgcattagttattaatagtaatcaattacggggtcattagttcatagcccatatatggagttccgcgttacataacttacggtaaatggcccgcctggctgaccgcccaacgacccccgcccattgac
gtcaataatgacgtatgttcccatagtaacgccaatagggactttccattgacgtcaatgggtggagtatttacggtaaactgcccacttggcagtacatcaagtgtatcatatgccaagtacgccccctattgacgtcaatga
cggtaaatggcccgcctggcattatgcccagtacatgaccttatgggactttcctacttggcagtacatctacgtattagtcatcgctattaccatggtgatgcggttttggcagtacatcaatgggcgtggatagcggtttgact
cacggggatttccaagtctccaccccattgacgtcaatgggagtttgttttggcaccaaaatcaacgggactttccaaaatgtcgtaacaactccgccccattgacgcaaatgggcggtaggcgtgtacggtgggaggtct
atataagcagagctggtttagtgaaccgtcagatccgctagcatt

Figure 44

SEQ. ID. NO.: 19

PNA Sequence "telomerase inhibitor" 13-mer (N-terminal end) [dopamine - succinic acid linker - CAGTTAGGGTTAG ]

SEQ. ID. NO.: 3

Target: pKaede plasmid with R18 sequence as insert has a 10 full match (0 nt from 3' end); 10-mer match with a single mismatch (1 nt from 3'); three 8-mer full matches (1, 1 and 3 nt from 3') and three 7-mer full matches (0, 1 and 3 nt from 3')

ggatcctcaggtaccggaactgcagcagagaattcaccacatccaaggaaagggaaactcgagaacaaagcttggatcagcggccgcggggaccatggtgagtctgattaaaccagaaatgaagatcaagctgct
tatggaaggcaatgtaaacgggcaccagtttgttattgagggagatggaaaaggccatccttttgagggaaaacagagtatggaccttgtagtcaaagaaggcgcacctctccctttgcctacgatatcttgacaacagc
attccattatggtaacagggttttgctaaatacccagaccatataccagactacttcaagcagtcgtttcccaaagggttttcttgggagcgaagcctgatgttcgaggacgggggcgtttgcatcgctacaaatgacataac
actgaaaggagacactttttttaacaaagttcgatttgatggcgtaaactttcccccaaatggtcctgttatgcagaagaagactctgaaatgggaggcatccactgagaaaatgtatttgcgtgatggagtgttgacgggcg
atattacaatggctctgctgcttaaaggagatgtccattaccgatgtgacttcagaactacttacaaatctaggcaggagggtgtcaagttgccaggatatcactttgtcgatcactgcatcagcatattgaggcatgacaaa
gactacaacgaggttaagctgtatgagcacgctgttgcccattctggattgccggacaacgtcaagtaatctagagggggccgcgactctagatcataatcagccataccacatttgtagaggttttacttgctttaaaaaac
ctcccacacctccccctgaacctgaaacataaaatgaatgcaattgttgttgttaacttgtttattgcagcttataatggttacaaataaagcaatagcatcacaaatttcacaaataaagcatttttttcactgcattctagttgtgg
tttgtccaaactcatcaatgtatcttaaggcgtaaattgtaagcgttaatattttgttaaaattcgcgttaaatttttgttaaatcagctcattttttaaccaataggccgaaatcggcaaaatcccttataaatcaaaagaatagacc
gagatagggttgagtgttgttccagtttggaacaagagtccactattaaagaacgtggactccaacgtcaaagggcgaaaaaccgtctatcagggcgatggcccactacgtgaaccatcaccctaatcaagtttttgg
ggtcgaggtgccgtaaagcactaaatcggaaccctaaagggagcccccgatttagagcttgacggggaaagccggcgaacgtggcgagaaaggaagggaagaaagcgaaaggagcgggcgctagggcgct
ggcaagtgtagcggtcacgctgcgcgtaaccaccacacccgccgcgcttaatgcgccgctacagggcgcgtcaggtggcacttttcggggaaatgtgcgcggaacccctatttgtttatttttctaaatacattcaaatatgt
atccgctcatgagacaataaccctgataaatgcttcaataatattgaaaaaggaagagtcctgaggcggaaagaaccagctgtggaatgtgtgtcagttagggtgtggaaagtccccaggctccccagcaggcaga
agtatgcaaagcatgcatctcaattagtcagcaaccaggtgtggaaagtccccaggctccccagcaggcagaagtatgcaaagcatgcatctcaattagtcagcaaccatagtcccgcccctaactccgcccatccc
gcccctaactccgcccagttccgcccattctccgccccatggctgactaattttttttatttatgcagaggccgaggccgcctcggcctctgagctattccagaagtagtgaggaggcttttttggaggcctaggcttttgcaaa
gatcgatcaagagacaggatgaggatcgtttcgcatgattgaacaagatggattgcacgcaggttctccggccgcttgggtggagaggctattcggctatgactgggcacaacagacaatcggctgctctgatgccgcc
gtgttccggctgtcagcgcaggggcgcccggttctttttgtcaagaccgacctgtccggtgccctgaatgaactgcaagacgaggcagcgcggctatcgtggctggccacgacgggcgttccttgcgcagctgtgctcga
cgttgtcactgaagcgggaagggactggctgctattgggcgaagtgccggggcaggatctcctgtcatctcaccttgctcctgccgagaaagtatccatcatggctgatgcaatgcggcggctgcatacgcttgatccggc
tacctgcccattcgaccaccaagcgaaacatcgcatcgagcgagcacgtactcggatggaagccggtcttgtcgatcaggatgatctggacgaagagcatcaggggctcgcgccagccgaactgttcgccaggctca
aggcgagcatgcccgacggcgaggatctcgtcgtgacccatggcgatgcctgcttgccgaatatcatggtggaaaatggccgcttttctggattcatcgactgtggccggctgggtgtggcggaccgctatcaggacata
gcgttggctacccgtgatattgctgaagagcttggcggcgaatgggctgaccgcttcctcgtgctttacggtatcgccgctcccgattcgcagcgcatcgccttctatcgccttcttgacgagttcttctgagcgggactctggg
gttcgaaatgaccgaccaagcgacgcccaacctgccatcacgagatttcgattccaccgccgccttctatgaaaggttgggcttcggaatcgttttccgggacgccggctggatgatcctccagcgcggggatctcatgct
ggagttcttcgcccaccctaggggggaggctaactgaaacacggaaggagacaataccggaaggaacccgcgctatgacggcaataaaaagacagaataaaacgcacggtgttgggtcgtttgttcataaacgcg
gggttcggtcccagggctggcactctgtcgataccccaccgagaccccattggggccaatacgcccgcgtttcttccttttccccaccccaccccccaagttcgggtgaaggcccagggctcgcagccaacgtcggggc
ggcaggccctgccatagcctcaggttactcatatatactttagattgatttaaaacttcatttttaatttaaaaggatctaggtgaagatcctttttgataatctcatgaccaaaatcccttaacgtgagttttcgttccactgagcgtc
agaccccgtagaaaagatcaaaggatcttcttgagatcctttttttctgcgcgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatacctcgctctgctaatcctgttaccagtggctgctgccagtggcgataagt
cgtgtcttaccgggttggactcaagacgatagttaccggataaggcgcagcggtcgggctgaacggggggttcgtgcacacagcccagcttggagcgaacgacctacaccgaactgagatacctacagcgtgagcta
tgagaaagcgccacgcttcccgaagggagaaaggcggacaggtatccggtaagcggcagggtcggaacaggagagcgcacgagggagcttccagggggaaacgcctggtatctttatagtcctgtcgggtttcgc
cacctctgacttgagcgtcgatttttgtgatgctcgtcaggggggcggagcctatggaaaaacgccagcaacgcggcctttttacggttcctggccttttgctggccttttgctcacatgttctttcctgcgttatcccctgattctgt
ggataaccgtattaccgccatgcattagttattaatagtaatcaattacggggtcattagttcatagcccatatatggagttccgcgttacataacttacggtaaatggcccgcctggctgaccgcccaacgacccccgccca
ttgacgtcaataatgacgtatgttcccatagtaacgccaatagggactttccattgacgtcaatgggtggagtatttacggtaaactgcccacttggcagtacatcaagtgtatcatatgccaagtacgccccctattgacgtc
aatgacggtaaatggcccgcctggcattatgcccagtacatgaccttatgggactttcctacttggcagtacatctacgtattagtcatcgctattaccatggtgatgcggttttggcagtacatcaatgggcgtggatagcggtt
tgactcacggggatttccaagtctccaccccattgacgtcaatgggagtttgttttggcaccaaaatcaacgggactttccaaaatgtcgtaacaactccgccccattgacgcaaatgggcggtaggcgtgtacggtggga
ggtctatataagcagagctggtttagtgaaccgtcagatccgctagcatt Figure 48
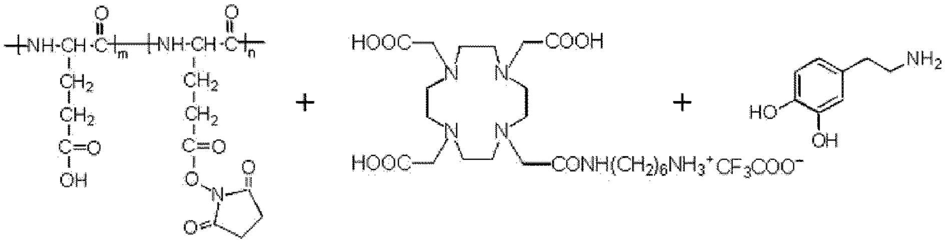
(1) (2) (3)
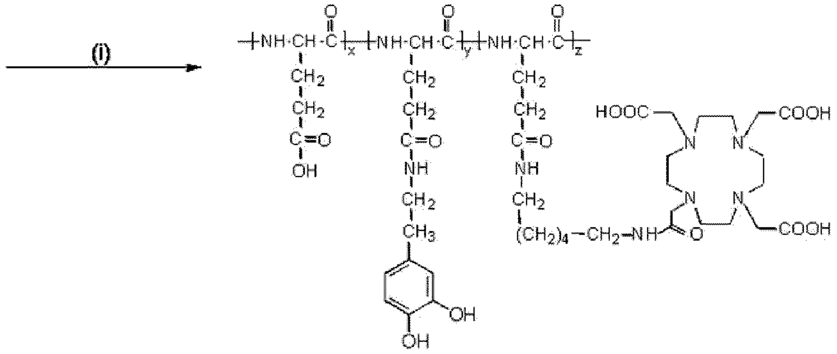
(4)
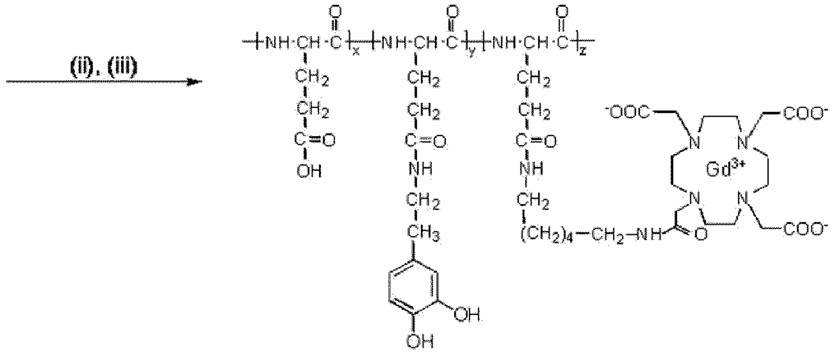
(5)

SEQUENCE LISTING

```
<160> NUMBER OF SEQ ID NOS: 19

<210> SEQ ID NO 1
<211> LENGTH: 4715
<212> TYPE: DNA
<213> ORGANISM: Artificial Sequence
<220> FEATURE:
<223> OTHER INFORMATION: Synthetic

<400> SEQUENCE: 1

tgatcctcag gtaccggaac tgcagcagag aattcaccac atccaaggaa agggaaactc     60
```

-continued

```
gagaacaaag cttggatcag cggccgcggg gaccatggtg agtctgatta aaccagaaat    120
gaagatcaag ctgcttatgg aaggcaatgt aaacgggcac cagtttgtta ttgagggaga    180
tggaaaaggc catccttttg agggaaaaca gagtatggac cttgtagtca aagaaggcgc    240
acctctccct tttgcctacg atatcttgac aacagcattc cattatggta acagggtttt    300
tgctaaatac ccagaccata taccagacta cttcaagcag tcgtttccca aagggttttc    360
ttgggagcga agcctgatgt tcgaggacgg gggcgtttgc atcgctacaa atgacataac    420
actgaaagga gacacttttt ttaacaaagt tcgatttgat ggcgtaaact ttcccccaaa    480
tggtcctgtt atgcagaaga agactctgaa atgggaggca tccactgaga aaatgtattt    540
gcgtgatgga gtgttgacgg gcgatattac aatggctctg ctgcttaaag gagatgtcca    600
ttaccgatgt gacttcagaa ctacttacaa atctaggcag gagggtgtca agttgccagg    660
atatcacttt gtcgatcact gcatcagcat attgaggcat gacaaagact acaacgaggt    720
taagctgtat gagcacgctg ttgcccattc tggattgccg gacaacgtca agtaatctag    780
agggggccgc gactctagat cataatcagc cataccacat ttgtagaggt tttacttgct    840
ttaaaaaacc tcccacacct ccccctgaac ctgaaacata aaatgaatgc aattgttgtt    900
gttaacttgt ttattgcagc ttataatggt tacaaataaa gcaatagcat cacaaatttc    960
acaaataaag catttttttc actgcattct agttgtggtt tgtccaaact catcaatgta   1020
tcttaaggcg taaattgtaa gcgttaatat tttgttaaaa ttcgcgttaa atttttgtta   1080
aatcagctca ttttttaacc aataggccga aatcggcaaa atcccttata aatcaaaaga   1140
atagaccgag atagggttga gtgttgttcc agtttggaac aagagtccac tattaaagaa   1200
cgtggactcc aacgtcaaag ggcgaaaaac cgtctatcag ggcgatggcc cactacgtga   1260
accatcaccc taatcaagtt ttttggggtc gaggtgccgt aaagcactaa atcggaaccc   1320
taaagggagc ccccgattta gagcttgacg gggaaagccg gcgaacgtgg cgagaaagga   1380
agggaagaaa gcgaaaggag cgggcgctag ggcgctggca agtgtagcgg tcacgctgcg   1440
cgtaaccacc acacccgccg cgcttaatgc gccgctacag ggcgcgtcag gtggcacttt   1500
tcggggaaat gtgcgcggaa cccctatttg tttatttttc taaatacatt caaatatgta   1560
tccgctcatg agacaataac cctgataaat gcttcaataa tattgaaaaa ggaagagtcc   1620
tgaggcggaa agaaccagct gtggaatgtg tgtcagttag ggtgtggaaa gtccccaggc   1680
tccccagcag gcagaagtat gcaaagcatg catctcaatt agtcagcaac caggtgtgga   1740
aagtccccag gctccccagc aggcagaagt atgcaaagca tgcatctcaa ttagtcagca   1800
accatagtcc cgcccctaac tccgcccatc ccgcccctaa ctccgcccag ttccgcccat   1860
tctccgcccc atggctgact aatttttttt atttatgcag aggccgaggc cgcctcggcc   1920
tctgagctat tccagaagta gtgaggaggc ttttttggag gcctaggctt ttgcaaagat   1980
cgatcaagag acaggatgag gatcgtttcg catgattgaa caagatggat tgcacgcagg   2040
ttctccggcc gcttgggtgg agaggctatt cggctatgac tgggcacaac agacaatcgg   2100
ctgctctgat gccgccgtgt tccggctgtc agcgcagggg cgcccggttc tttttgtcaa   2160
gaccgacctg tccggtgccc tgaatgaact gcaagacgag gcagcgcggc tatcgtggct   2220
ggccacgacg ggcgttcctt gcgcagctgt gctcgacgtt gtcactgaag cgggaaggga   2280
ctggctgcta ttgggcgaag tgccggggca ggatctcctg tcatctcacc ttgctcctgc   2340
cgagaaagta tccatcatgg ctgatgcaat gcggcggctg catacgcttg atccggctac   2400
ctgcccattc gaccaccaag cgaaacatcg catcgagcga gcacgtactc ggatggaagc   2460
```

```
cggtcttgtc gatcaggatg atctggacga agagcatcag gggctcgcgc cagccgaact   2520

gttcgccagg ctcaaggcga gcatgcccga cggcgaggat ctcgtcgtga cccatggcga   2580

tgcctgcttg ccgaatatca tggtggaaaa tggccgcttt tctggattca tcgactgtgg   2640

ccggctgggt gtggcggacc gctatcagga catagcgttg gctacccgtg atattgctga   2700

agagcttggc ggcgaatggg ctgaccgctt cctcgtgctt tacggtatcg ccgctcccga   2760

ttcgcagcgc atcgccttct atcgccttct tgacgagttc ttctgagcgg gactctgggg   2820

ttcgaaatga ccgaccaagc gacgcccaac ctgccatcac gagatttcga ttccaccgcc   2880

gccttctatg aaaggttggg cttcggaatc gttttccggg acgccggctg gatgatcctc   2940

cagcgcgggg atctcatgct ggagttcttc gcccacccta gggggaggct aactgaaaca   3000

cggaaggaga caataccgga aggaacccgc gctatgacgg caataaaaag acagaataaa   3060

acgcacggtg ttgggtcgtt tgttcataaa cgcggggttc ggtcccaggg ctggcactct   3120

gtcgataccc caccgagacc ccattggggc caatacgccc gcgtttcttc cttttcccca   3180

ccccaccccc caagttcggg tgaaggccca gggctcgcag ccaacgtcgg ggcggcaggc   3240

cctgccatag cctcaggtta ctcatatata ctttagattg atttaaaact tcatttttaa   3300

tttaaaagga tctaggtgaa gatccttttt gataatctca tgaccaaaat cccttaacgt   3360

gagttttcgt tccactgagc gtcagacccc gtagaaaaga tcaaaggatc ttcttgagat   3420

cctttttttc tgcgcgtaat ctgctgcttg caaacaaaaa aaccaccgct accagcggtg   3480

gtttgtttgc cggatcaaga gctaccaact ctttttccga aggtaactgg cttcagcaga   3540

gcgcagatac caaatactgt ccttctagtg tagccgtagt taggccacca cttcaagaac   3600

tctgtagcac cgcctacata cctcgctctg ctaatcctgt taccagtggc tgctgccagt   3660

ggcgataagt cgtgtcttac cgggttggac tcaagacgat agttaccgga taaggcgcag   3720

cggtcgggct gaacgggggg ttcgtgcaca cagcccagct tggagcgaac gacctacacc   3780

gaactgagat acctacagcg tgagctatga gaaagcgcca cgcttcccga agggagaaag   3840

gcggacaggt atccggtaag cggcagggtc ggaacaggag agcgcacgag ggagcttcca   3900

gggggaaacg cctggtatct ttatagtcct gtcgggtttc gccacctctg acttgagcgt   3960

cgatttttgt gatgctcgtc aggggggcgg agcctatgga aaaacgccag caacgcggcc   4020

tttttacggt tcctggcctt ttgctggcct tttgctcaca tgttctttcc tgcgttatcc   4080

cctgattctg tggataaccg tattaccgcc atgcattagt tattaatagt aatcaattac   4140

ggggtcatta gttcatagcc catatatgga gttccgcgtt acataactta cggtaaatgg   4200

cccgcctggc tgaccgccca acgacccccg cccattgacg tcaataatga cgtatgttcc   4260

catagtaacg ccaataggga ctttccattg acgtcaatgg gtggagtatt tacggtaaac   4320

tgcccacttg gcagtacatc aagtgtatca tatgccaagt acgcccccta ttgacgtcaa   4380

tgacggtaaa tggcccgcct ggcattatgc ccagtacatg accttatggg actttcctac   4440

ttggcagtac atctacgtat tagtcatcgc tattaccatg gtgatgcggt tttggcagta   4500

catcaatggg cgtggatagc ggtttgactc acggggattt ccaagtctcc accccattga   4560

cgtcaatggg agtttgtttt ggcaccaaaa tcaacgggac tttccaaaat gtcgtaacaa   4620

ctccgcccca ttgacgcaaa tgggcggtag gcgtgtacgg tgggaggtct atataagcag   4680

agctggttta gtgaaccgtc agatccgcta gcatt                              4715
```

<210> SEQ ID NO 2
<211> LENGTH: 4715

-continued

<212> TYPE: DNA
<213> ORGANISM: Artificial Sequence
<220> FEATURE:
<223> OTHER INFORMATION: Synthetic

<400> SEQUENCE: 2
ggatcctcag gtaccggaac tgcagcagag aattcaccac atccaaggaa agggaaactc 60
gagaacaaag cttggatcag cggccgcggg gaccatggtg agtctgatta aaccagaaat 120
gaagatcaag ctgcttatgg aaggcaatgt aaacgggcac cagtttgtta ttgagggaga 180
tggaaaaggc catccttttg agggaaaaca gagtatggac cttgtagtca aagaaggcgc 240
acctctccct tttgcctacg atatcttgac aacagcattc cattatggta acagggtttt 300
tgctaaatac ccagaccata taccagacta cttcaagcag tcgtttccca aagggttttc 360
ttgggagcga agcctgatgt tcgaggacgg gggcgtttgc atcgctacaa atgacataac 420
actgaaagga gacacttttt ttaacaaagt tcgatttgat ggcgtaaact ttcccccaaa 480
tggtcctgtt atgcagaaga agactctgaa atgggaggca tccactgaga aaatgtattt 540
gcgtgatgga gtgttgacgg gcgatattac aatggctctg ctgcttaaag gagatgtcca 600
ttaccgatgt gacttcagaa ctacttacaa atctaggcag gagggtgtca agttgccagg 660
atatcacttt gtcgatcact gcatcagcat attgaggcat gacaaagact acaacgaggt 720
taagctgtat gagcacgctg ttgcccattc tggattgccg gacaacgtca agtaatctag 780
agggggccgc gactctagat cataatcagc cataccacat ttgtagaggt tttacttgct 840
ttaaaaaacc tcccacacct ccccctgaac ctgaaacata aaatgaatgc aattgttgtt 900
gttaacttgt ttattgcagc ttataatggt tacaaataaa gcaatagcat cacaaatttc 960
acaaataaag catttttttc actgcattct agttgtggtt tgtccaaact catcaatgta 1020
tcttaaggcg taaattgtaa gcgttaatat tttgttaaaa ttcgcgttaa atttttgtta 1080
aatcagctca ttttttaacc aataggccga aatcggcaaa atcccttata aatcaaaaga 1140
atagaccgag atagggttga gtgttgttcc agtttggaac aagagtccac tattaaagaa 1200
cgtggactcc aacgtcaaag ggcgaaaaac cgtctatcag ggcgatggcc cactacgtga 1260
accatcaccc taatcaagtt ttttggggtc gaggtgccgt aaagcactaa atcggaaccc 1320
taaagggagc ccccgattta gagcttgacg gggaaagccg gcgaacgtgg cgagaaagga 1380
agggaagaaa gcgaaaggag cgggcgctag ggcgctggca agtgtagcgg tcacgctgcg 1440
cgtaaccacc acacccgccg cgcttaatgc gccgctacag ggcgcgtcag gtggcacttt 1500
tcggggaaat gtgcgcggaa cccctatttg tttatttttc taaatacatt caaatatgta 1560
tccgctcatg agacaataac cctgataaat gcttcaataa tattgaaaaa ggaagagtcc 1620
tgaggcggaa agaaccagct gtggaatgtg tgtcagttag ggtgtggaaa gtccccaggc 1680
tccccagcag gcagaagtat gcaaagcatg catctcaatt agtcagcaac caggtgtgga 1740
aagtccccag gctccccagc aggcagaagt atgcaaagca tgcatctcaa ttagtcagca 1800
accatagtcc cgcccctaac tccgcccatc ccgcccctaa ctccgcccag ttccgcccat 1860
tctccgcccc atggctgact aatttttttt atttatgcag aggccgaggc cgcctcggcc 1920
tctgagctat tccagaagta gtgaggaggc ttttttggag gcctaggctt ttgcaaagat 1980
cgatcaagag acaggatgag gatcgtttcg catgattgaa caagatggat tgcacgcagg 2040
ttctccggcc gcttgggtgg agaggctatt cggctatgac tgggcacaac agacaatcgg 2100
ctgctctgat gccgccgtgt tccggctgtc agcgcagggg cgcccggttc tttttgtcaa 2160
gaccgacctg tccggtgccc tgaatgaact gcaagacgag gcagcgcggc tatcgtggct 2220

-continued

```
ggccacgacg ggcgttcctt gcgcagctgt gctcgacgtt gtcactgaag cgggaaggga   2280
ctggctgcta ttgggcgaag tgccggggca ggatctcctg tcatctcacc ttgctcctgc   2340
cgagaaagta tccatcatgg ctgatgcaat gcggcggctg catacgcttg atccggctac   2400
ctgcccattc gaccaccaag cgaaacatcg catcgagcga gcacgtactc ggatggaagc   2460
cggtcttgtc gatcaggatg atctggacga agagcatcag gggctcgcgc cagccgaact   2520
gttcgccagg ctcaaggcga gcatgcccga cggcgaggat ctcgtcgtga cccatggcga   2580
tgcctgcttg ccgaatatca tggtggaaaa tggccgcttt tctggattca tcgactgtgg   2640
ccggctgggt gtggcggacc gctatcagga catagcgttg gctacccgtg atattgctga   2700
agagcttggc ggcgaatggg ctgaccgctt cctcgtgctt tacggtatcg ccgctcccga   2760
ttcgcagcgc atcgccttct atcgccttct tgacgagttc ttctgagcgg gactctgggg   2820
ttcgaaatga ccgaccaagc gacgcccaac ctgccatcac gagatttcga ttccaccgcc   2880
gccttctatg aaaggttggg cttcggaatc gttttccggg acgccggctg gatgatcctc   2940
cagcgcgggg atctcatgct ggagttcttc gcccacccta gggggaggct aactgaaaca   3000
cggaaggaga caataccgga aggaacccgc gctatgacgg caataaaaag acagaataaa   3060
acgcacggtg ttgggtcgtt tgttcataaa cgcggggttc ggtcccaggg ctggcactct   3120
gtcgataccc caccgagacc ccattggggc caatacgccc gcgtttcttc cttttcccca   3180
ccccaccccc caagttcggg tgaaggccca gggctcgcag ccaacgtcgg ggcggcaggc   3240
cctgccatag cctcaggtta ctcatatata ctttagattg atttaaaact tcatttttaa   3300
tttaaaagga tctaggtgaa gatccttttt gataatctca tgaccaaaat cccttaacgt   3360
gagttttcgt tccactgagc gtcagacccc gtagaaaaga tcaaaggatc ttcttgagat   3420
cctttttttc tgcgcgtaat ctgctgcttg caaacaaaaa aaccaccgct accagcggtg   3480
gtttgtttgc cggatcaaga gctaccaact ctttttccga aggtaactgg cttcagcaga   3540
gcgcagatac caaatactgt ccttctagtg tagccgtagt taggccacca cttcaagaac   3600
tctgtagcac cgcctacata cctcgctctg ctaatcctgt taccagtggc tgctgccagt   3660
ggcgataagt cgtgtcttac cgggttggac tcaagacgat agttaccgga taaggcgcag   3720
cggtcgggct gaacgggggg ttcgtgcaca cagcccagct tggagcgaac gacctacacc   3780
gaactgagat acctacagcg tgagctatga gaaagcgcca cgcttcccga agggagaaag   3840
gcggacaggt atccggtaag cggcagggtc ggaacaggag agcgcacgag ggagcttcca   3900
gggggaaacg cctggtatct ttatagtcct gtcgggtttc gccacctctg acttgagcgt   3960
cgatttttgt gatgctcgtc aggggggcgg agcctatgga aaaacgccag caacgcggcc   4020
tttttacggt tcctggcctt ttgctggcct tttgctcaca tgttctttcc tgcgttatcc   4080
cctgattctg tggataaccg tattaccgcc atgcattagt tattaatagt aatcaattac   4140
ggggtcatta gttcatagcc catatatgga gttccgcgtt acataactta cggtaaatgg   4200
cccgcctggc tgaccgccca acgacccccg cccattgacg tcaataatga cgtatgttcc   4260
catagtaacg ccaataggga ctttccattg acgtcaatgg gtggagtatt tacggtaaac   4320
tgcccacttg gcagtacatc aagtgtatca tatgccaagt acgcccccta ttgacgtcaa   4380
tgacggtaaa tggcccgcct ggcattatgc ccagtacatg accttatggg actttcctac   4440
ttggcagtac atctacgtat tagtcatcgc tattaccatg gtgatgcggt tttggcagta   4500
catcaatggg cgtggatagc ggtttgactc acggggattt ccaagtctcc accccattga   4560
cgtcaatggg agtttgtttt ggcaccaaaa tcaacgggac tttccaaaat gtcgtaacaa   4620
```

```
ctccgcccca ttgacgcaaa tgggcggtag gcgtgtacgg tgggaggtct atataagcag   4680

agctggttta gtgaaccgtc agatccgcta gcatt                              4715


<210> SEQ ID NO 3
<211> LENGTH: 4715
<212> TYPE: DNA
<213> ORGANISM: Artificial Sequence
<220> FEATURE:
<223> OTHER INFORMATION: Synthetic

<400> SEQUENCE: 3

ggatcctcag gtaccggaac tgcagcagag aattcaccac atccaaggaa agggaaactc     60

gagaacaaag cttggatcag cggccgcggg gaccatggtg agtctgatta aaccagaaat    120

gaagatcaag ctgcttatgg aaggcaatgt aaacgggcac cagtttgtta ttgagggaga    180

tggaaaaggc catccttttg agggaaaaca gagtatggac cttgtagtca aagaaggcgc    240

acctctccct tttgcctacg atatcttgac aacagcattc cattatggta acagggtttt    300

tgctaaatac ccagaccata taccagacta cttcaagcag tcgtttccca aagggttttc    360

ttgggagcga agcctgatgt tcgaggacgg gggcgtttgc atcgctacaa atgacataac    420

actgaaagga gacacttttt ttaacaaagt tcgatttgat ggcgtaaact ttcccccaaa    480

tggtcctgtt atgcagaaga agactctgaa atgggaggca tccactgaga aaatgtattt    540

gcgtgatgga gtgttgacgg gcgatattac aatggctctg ctgcttaaag gagatgtcca    600

ttaccgatgt gacttcagaa ctacttacaa atctaggcag gagggtgtca agttgccagg    660

atatcacttt gtcgatcact gcatcagcat attgaggcat gacaaagact acaacgaggt    720

taagctgtat gagcacgctg ttgcccattc tggattgccg gacaacgtca agtaatctag    780

agggggccgc gactctagat cataatcagc cataccacat ttgtagaggt tttacttgct    840

ttaaaaaacc tcccacacct ccccctgaac ctgaaacata aaatgaatgc aattgttgtt    900

gttaacttgt ttattgcagc ttataatggt tacaaataaa gcaatagcat cacaaatttc    960

acaaataaag catttttttc actgcattct agttgtggtt tgtccaaact catcaatgta   1020

tcttaaggcg taaattgtaa gcgttaatat tttgttaaaa ttcgcgttaa atttttgtta   1080

aatcagctca ttttttaacc aataggccga aatcggcaaa atcccttata aatcaaaaga   1140

atagaccgag atagggttga gtgttgttcc agtttggaac aagagtccac tattaaagaa   1200

cgtggactcc aacgtcaaag ggcgaaaaac cgtctatcag ggcgatggcc cactacgtga   1260

accatcaccc taatcaagtt ttttggggtc gaggtgccgt aaagcactaa atcggaaccc   1320

taaagggagc ccccgattta gagcttgacg gggaaagccg gcgaacgtgg cgagaaagga   1380

agggaagaaa gcgaaaggag cgggcgctag ggcgctggca agtgtagcgg tcacgctgcg   1440

cgtaaccacc acacccgccg cgcttaatgc gccgctacag ggcgcgtcag gtggcacttt   1500

tcggggaaat gtgcgcggaa cccctatttg tttatttttc taaatacatt caaatatgta   1560

tccgctcatg agacaataac cctgataaat gcttcaataa tattgaaaaa ggaagagtcc   1620

tgaggcggaa agaaccagct gtggaatgtg tgtcagttag ggtgtggaaa gtccccaggc   1680

tccccagcag gcagaagtat gcaaagcatg catctcaatt agtcagcaac caggtgtgga   1740

aagtccccag gctccccagc aggcagaagt atgcaaagca tgcatctcaa ttagtcagca   1800

accatagtcc cgcccctaac tccgcccatc ccgcccctaa ctccgcccag ttccgcccat   1860

tctccgcccc atggctgact aatttttttt atttatgcag aggccgaggc cgcctcggcc   1920

tctgagctat tccagaagta gtgaggaggc ttttttggag gcctaggctt ttgcaaagat   1980
```

-continued

```
cgatcaagag acaggatgag gatcgtttcg catgattgaa caagatggat tgcacgcagg   2040
ttctccggcc gcttgggtgg agaggctatt cggctatgac tgggcacaac agacaatcgg   2100
ctgctctgat gccgccgtgt tccggctgtc agcgcagggg cgcccggttc tttttgtcaa   2160
gaccgacctg tccggtgccc tgaatgaact gcaagacgag gcagcgcggc tatcgtggct   2220
ggccacgacg ggcgttcctt gcgcagctgt gctcgacgtt gtcactgaag cgggaaggga   2280
ctggctgcta ttgggcgaag tgccggggca ggatctcctg tcatctcacc ttgctcctgc   2340
cgagaaagta tccatcatgg ctgatgcaat gcggcggctg catacgcttg atccggctac   2400
ctgcccattc gaccaccaag cgaaacatcg catcgagcga gcacgtactc ggatggaagc   2460
cggtcttgtc gatcaggatg atctggacga agagcatcag gggctcgcgc cagccgaact   2520
gttcgccagg ctcaaggcga gcatgcccga cggcgaggat ctcgtcgtga cccatggcga   2580
tgcctgcttg ccgaatatca tggtggaaaa tggccgcttt tctggattca tcgactgtgg   2640
ccggctgggt gtggcggacc gctatcagga catagcgttg gctacccgtg atattgctga   2700
agagcttggc ggcgaatggg ctgaccgctt cctcgtgctt tacggtatcg ccgctcccga   2760
ttcgcagcgc atcgccttct atcgccttct tgacgagttc ttctgagcgg gactctgggg   2820
ttcgaaatga ccgaccaagc gacgcccaac ctgccatcac gagatttcga ttccaccgcc   2880
gccttctatg aaaggttggg cttcggaatc gttttccggg acgccggctg gatgatcctc   2940
cagcgcgggg atctcatgct ggagttcttc gcccacccta gggggaggct aactgaaaca   3000
cggaaggaga caataccgga aggaacccgc gctatgacgg caataaaaag acagaataaa   3060
acgcacggtg ttgggtcgtt tgttcataaa cgcggggttc ggtcccaggg ctggcactct   3120
gtcgataccc caccgagacc ccattggggc caatacgccc gcgtttcttc cttttcccca   3180
ccccaccccc caagttcggg tgaaggccca gggctcgcag ccaacgtcgg ggcggcaggc   3240
cctgccatag cctcaggtta ctcatatata ctttagattg atttaaaact tcatttttaa   3300
tttaaaagga tctaggtgaa gatccttttt gataatctca tgaccaaaat cccttaacgt   3360
gagttttcgt tccactgagc gtcagacccc gtagaaaaga tcaaaggatc ttcttgagat   3420
cctttttttc tgcgcgtaat ctgctgcttg caaacaaaaa aaccaccgct accagcggtg   3480
gtttgtttgc cggatcaaga gctaccaact ctttttccga aggtaactgg cttcagcaga   3540
gcgcagatac caaatactgt ccttctagtg tagccgtagt taggccacca cttcaagaac   3600
tctgtagcac cgcctacata cctcgctctg ctaatcctgt taccagtggc tgctgccagt   3660
ggcgataagt cgtgtcttac cgggttggac tcaagacgat agttaccgga taaggcgcag   3720
cggtcgggct gaacgggggg ttcgtgcaca cagcccagct tggagcgaac gacctacacc   3780
gaactgagat acctacagcg tgagctatga gaaagcgcca cgcttcccga agggagaaag   3840
gcggacaggt atccggtaag cggcagggtc ggaacaggag agcgcacgag ggagcttcca   3900
gggggaaacg cctggtatct ttatagtcct gtcgggtttc gccacctctg acttgagcgt   3960
cgatttttgt gatgctcgtc aggggggcgg agcctatgga aaaacgccag caacgcggcc   4020
tttttacggt tcctggcctt ttgctggcct tttgctcaca tgttctttcc tgcgttatcc   4080
cctgattctg tggataaccg tattaccgcc atgcattagt tattaatagt aatcaattac   4140
ggggtcatta gttcatagcc catatatgga gttccgcgtt acataactta cggtaaatgg   4200
cccgcctggc tgaccgccca acgacccccg cccattgacg tcaataatga cgtatgttcc   4260
catagtaacg ccaataggga ctttccattg acgtcaatgg gtggagtatt tacggtaaac   4320
tgcccacttg gcagtacatc aagtgtatca tatgccaagt acgcccccta ttgacgtcaa   4380
```

```
tgacggtaaa tggcccgcct ggcattatgc ccagtacatg accttatggg actttcctac   4440

ttggcagtac atctacgtat tagtcatcgc tattaccatg gtgatgcggt tttggcagta   4500

catcaatggg cgtggatagc ggtttgactc acggggattt ccaagtctcc accccattga   4560

cgtcaatggg agtttgtttt ggcaccaaaa tcaacgggac tttccaaaat gtcgtaacaa   4620

ctccgcccca ttgacgcaaa tgggcggtag gcgtgtacgg tgggaggtct atataagcag   4680

agctggttta gtgaaccgtc agatccgcta gcatt                              4715


<210> SEQ ID NO 4
<211> LENGTH: 51
<212> TYPE: DNA
<213> ORGANISM: Artificial Sequence
<220> FEATURE:
<223> OTHER INFORMATION: Synthetic

<400> SEQUENCE: 4

tcagcctggt ctaccaagca aactccagta cagccaggga acatgagaga c              51


<210> SEQ ID NO 5
<211> LENGTH: 51
<212> TYPE: DNA
<213> ORGANISM: Artificial Sequence
<220> FEATURE:
<223> OTHER INFORMATION: Synthetic

<400> SEQUENCE: 5

tgtctctcat gttccctggc tgtactggag tttgcttggt agaccaggct g              51


<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6

atgttcgagg cgcgcctggt c                                               21


<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7

agatccttct tcatcctcga                                                 20


<210> SEQ ID NO 8
<211> LENGTH: 15
<212> TYPE: DNA
<213> ORGANISM: Artificial Sequence
<220> FEATURE:
<223> OTHER INFORMATION: Synthetic

<400> SEQUENCE: 8

ttccttggat gtggt                                                      15


<210> SEQ ID NO 9
<211> LENGTH: 13
<212> TYPE: PRT
<213> ORGANISM: Artificial Sequence
<220> FEATURE:
<223> OTHER INFORMATION: Synthetic
```

<400> SEQUENCE: 9

Arg Arg Arg His Ile Val Arg Lys Arg Thr Leu Arg Arg
1               5                   10

<210> SEQ ID NO 10
<211> LENGTH: 16
<212> TYPE: DNA
<213> ORGANISM: Artificial Sequence
<220> FEATURE:
<223> OTHER INFORMATION: Synthetic

<400> SEQUENCE: 10
tttccttgga tgtggt 16

<210> SEQ ID NO 11
<211> LENGTH: 16
<212> TYPE: DNA
<213> ORGANISM: Artificial Sequence
<220> FEATURE:
<223> OTHER INFORMATION: Synthetic

<400> SEQUENCE: 11
accacatcca aggaaa 16

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ttgcttggta gaccaggctg 20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cagcctggtc taccaagcaa 20

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
ccccaccaca tccaaggaaa gggg 24

<210> SEQ ID NO 15
<211> LENGTH: 28
<212> TYPE: DNA
<213> ORGANISM: Artificial Sequence
<220> FEATURE:
<223> OTHER INFORMATION: Synthetic

<400> SEQUENCE: 15
ccccgagaga gagagagaga gagagggg 28

<210> SEQ ID NO 16

-continued

```
<211> LENGTH: 22
<212> TYPE: DNA
<213> ORGANISM: Artificial Sequence
<220> FEATURE:
<223> OTHER INFORMATION: Synthetic

<400> SEQUENCE: 16

tcgagtttcc ttggatgtgg tg                                          22


<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17

aattcaccac atccaaggaa ac                                          22


<210> SEQ ID NO 18
<211> LENGTH: 15
<212> TYPE: DNA
<213> ORGANISM: Artificial Sequence
<220> FEATURE:
<223> OTHER INFORMATION: Synthetic

<400> SEQUENCE: 18

aagatattcc atgac                                                  15


<210> SEQ ID NO 19
<211> LENGTH: 13
<212> TYPE: DNA
<213> ORGANISM: Artificial Sequence
<220> FEATURE:
<223> OTHER INFORMATION: Synthetic

<400> SEQUENCE: 19

cagttagggt tag                                                    13
```

MULTIFUNCTION NANOCONJUGATES FOR IMAGING APPLICATIONS AND TARGETED TREATMENT

CROSS REFERENCE TO RELATED APPLICATIONS

This application claims priority to provisional patent application Ser. No. 61/036,628, filed Mar. 14, 2008, which is herein incorporated by reference in its entirety.

GOVERNMENT SUPPORT

This invention was made with government support under Grand Nos. CA107467-01, EB002100-03 and U54CA119341 awarded by the National Institute of Health. The government has certain rights in the invention.

FIELD OF THE INVENTION

The present invention relates to nanoconjugates. In particular, the present invention provides nanoconjugates for diagnostic (e.g., imaging), research, and clinical (e.g., targeted treatment) applications.

BACKGROUND OF THE INVENTION

During their lifetime, organisms often acquire unwanted foreign or mutated DNA that may negatively affect their health. Traditional modes of diagnosis are often unable to detect the presence of deleterious DNA; additionally, common treatments for such diseases do not address the underlying cause of disease—changes at the level of the genome, and therefore do not discriminate well between target and healthy cells. This lowers the therapeutic efficacy of such conventional treatments. New types of early-detection imaging agents and sequence-specific gene therapies are needed to diagnose and remove unwanted DNA in diseased cells, without affecting healthy, neighboring cells. Imaging and elimination of unwanted genes and gene products have been major goals of molecular biology over the last few decades, and a sudden proliferation of different RNA interference techniques (Gonzalez-Alegre, Pharmacol. Ther. 2007, 114, 34-55; Natt, Curr Opin Mol. Ther. 2007, 9, 242-247; Scherer et al., Gene Ther. 2007, 14, 1057-1064) attest to that trend. As a result of recent advancements in nanotechnology, biologists now have access to materials with novel properties which emerge only at the nano scale, enabling innovative imaging and therapeutic approaches (Roco et al., The Office of Science and Technology. 2007; Rajh et al., J Phys Chem B. 2002, 106, 10543-10552; Rajh et al., Chemical Physics Letters. 2001, 344, 31-39).

Although DNA nanoconjugates may serve as possible vehicles to image and remove unwanted DNA, their targeting efficiency and intracellular retention may be lowered by cellular factors, such as degradation by intracellular nucleases. To address these potential problems and improve the stability of hybridization with target sequences, additional nanoconjugates are needed for diagnostic, clinical, and research applications.

SUMMARY OF THE INVENTION

The present invention relates to nanoconjugates. In particular, the present invention provides nanoconjugates for diagnostic (e.g., imaging), research, and clinical (e.g., targeted treatment) applications.

For example, in some embodiments, the present invention provides a multifunctional nanoconjugate comprising: a nanoparticle comprising a magnetic or superparamagnetic iron oxide core covered by a metal or metal oxide (e.g., $TiO_2$) nanoparticle shell; and at least one biological molecule (e.g., a nucleic acid, a peptide-nucleic acid (PNA), a peptide, a polypeptide and an antibody) conjugated to the nanoparticle core. In some embodiments, the nanoparticles are $TiO_2$ nanoparticles. In some embodiments, the nanoparticles are between 0.1 and 1000 nm (e.g., approximately 1000 nm, 500 nm, 100 nm, 20 nm, 10 nm 5 nm, or 1 nm) in diameter. In some embodiments, the nanoconjugates further comprise an optical or additional magnetic resonance imaging contrast agent (e.g., a fluorescent dye such as Alizarin Red S or a metal ligand molecule such as a Gadolinium chelating molecule). In some embodiments, the biological molecule specifically interacts with an in vivo target (e.g., a tumor, cancer marker (e.g., a cell surface marker or an oncogene within a tumor cell)). In some embodiments, the nanoconjugate further comprises a therapeutic agent (e.g., a chemotherapeutic agent).

In further embodiments, the present invention provides a method of targeting an vivo target (e.g., a tumor, cancer marker (e.g., a cell surface marker or an oncogene within a tumor cell)), comprising: contacting an organism with a nanoconjugate comprising a nanoparticle core comprising a magnetic nanocomponent coated by at least one layer of a metal; and at least one biological molecule (e.g., a nucleic acid, a peptide-nucleic acid (PNA), a peptide, a polypeptide, and an antibody) conjugated to the nanoparticle core under conditions such that the nanoconjugate interacts with the in vivo target. In some embodiments, the nanoparticles are $TiO_2$ nanoparticles. In some embodiments, the nanoconjugates further comprise an imaging contrast agent (e.g., a fluorescent dye such as Alizarin Red S or a metal ligand molecule such as a Gadolinium chelating molecule). In some embodiments, the method further comprises the step of visualizing the imaging agent in the organism (e.g., utilizes an imaging technique selected from the group consisting of X-ray imaging, computer tomography (CT) imaging, and magnetic resonance imaging (MRI)). In some embodiments, the method further comprises the step of destroying the in vivo target. In some embodiments, the destroying the oncogene comprises a technique such as neutron capture therapy by the imaging agent or generation of reactive oxygen species by the agent. In some embodiments, the nanoconjugate further comprises a therapeutic agent (e.g., chemotherapeutic agent) and wherein the destroying the target comprises the step of contacting the target with the therapeutic agent.

Plasmid cleavage resulting from excitation of alizarin red s-coated $TiO_2$ nanoparticles is due to release of reactive oxygen species. SC=supercoiled, N=nicked, L=linearized.

Figure 39:
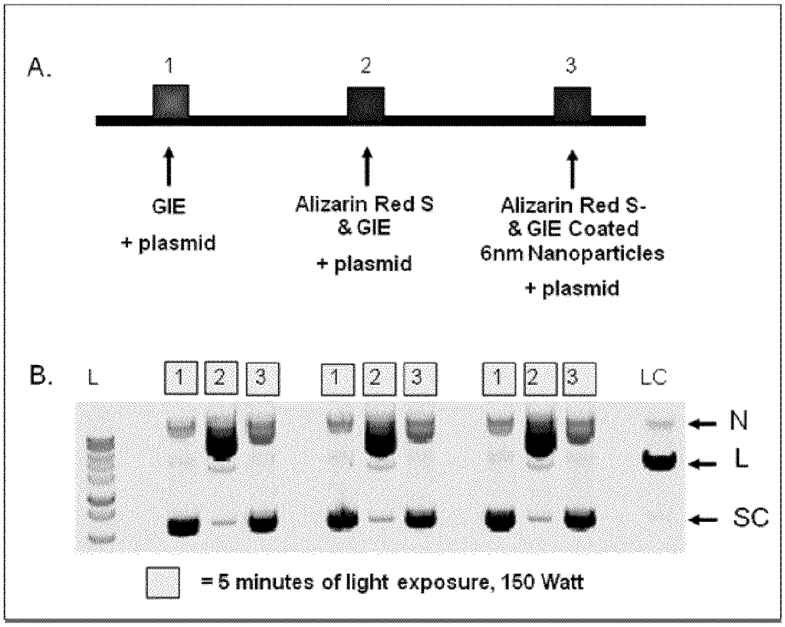

FIG. 39. A) Samples exposed to light. B) Further coating of alizarin red s-coated $TiO_2$ nanoparticles with glycidyl isopropyl ether (GIE) decreases plasmid cleavage. SC=supercoiled, N=nicked, L=linearized, LC=enzyme digested linear control.

Figure 40:
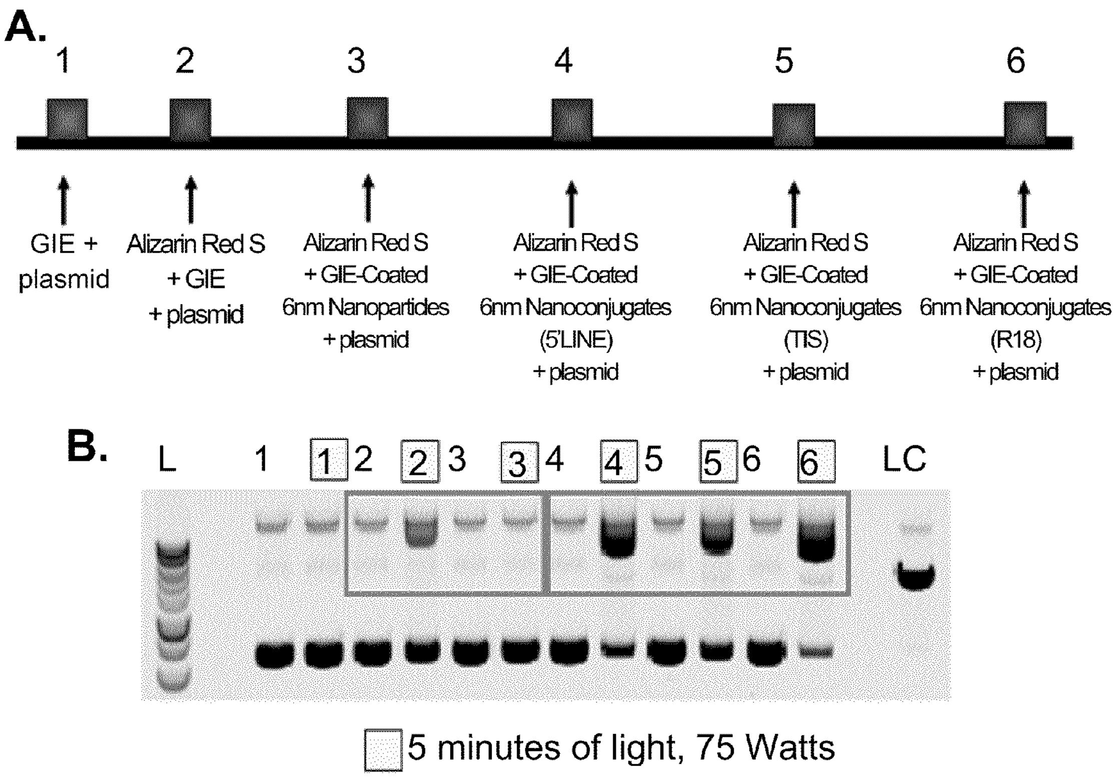

FIG. 40. Effect of conjugating PNAs to GIE-alizarin red-s coated $TiO_2$ nanoparticles (resulting in PNA-$TiO_2$ nanoconjugates) on plasmid cleavage. A) Samples exposed to either no light or light. B) Gel electrophoresis results showing plasmid cleavage resulting from excitation of GIE-alizarin red s-coated PNA-$TiO_2$ nanoconjugates with 4 PNAs per nanoconjugate (three different PNA sequences shown).

Figure 41:
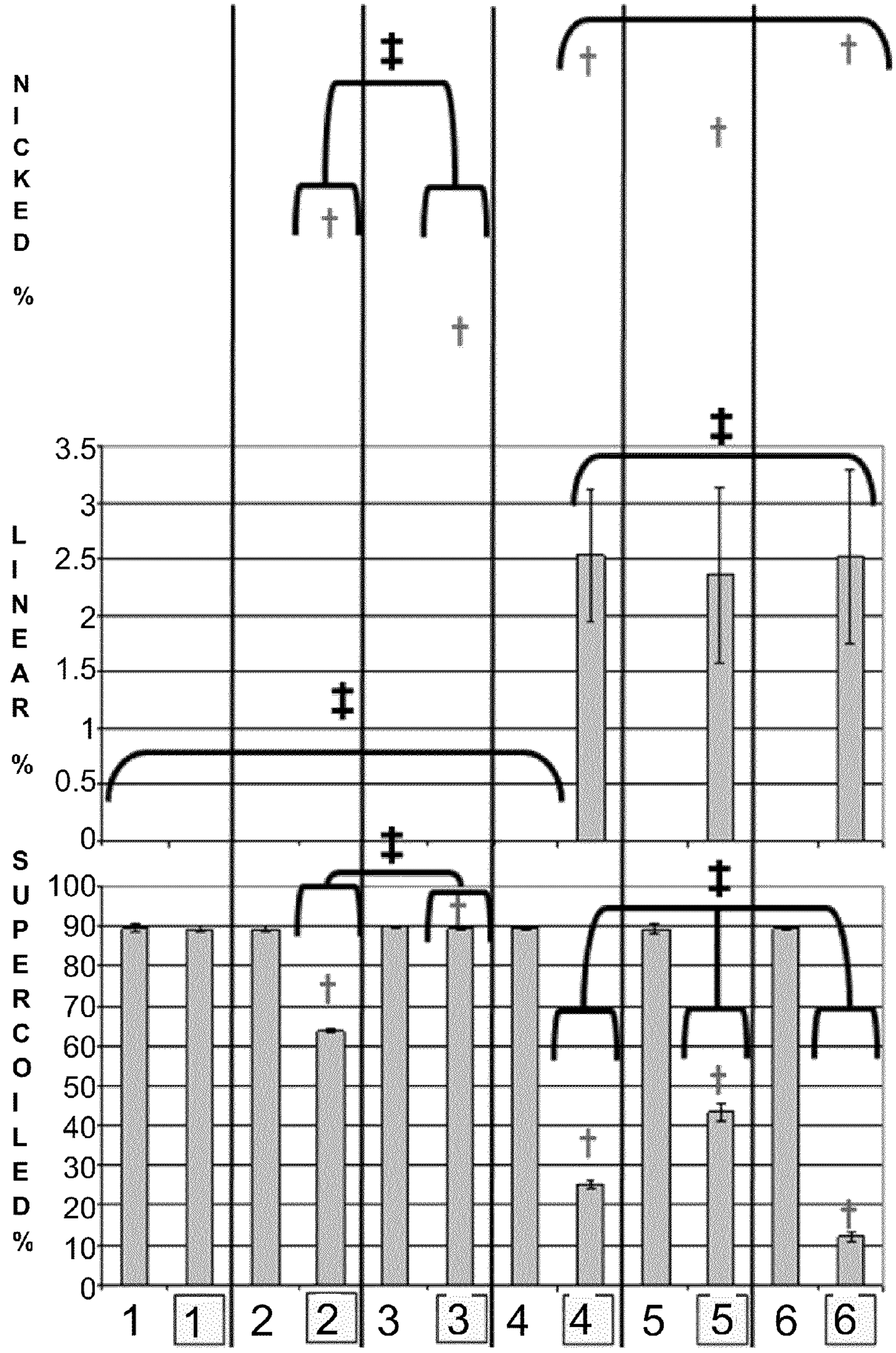

FIG. 41. Effect of conjugating PNAs to GIE-alizarin red-s coated $TiO_2$ nanoparticles (resulting in PNA-$TiO_2$ nanoconjugates) on plasmid cleavage. ‡=intergroup sig dif ($p<0.01$), †=specified sig dif ($p<0.01$). SC=supercoiled, N=nicked, L=linearized.

FIG. 42. Analysis of R18 complementary and partially complementary sequences in the pKaede-MN1 plasmid with insert. (SEQ ID NO: 1)

FIG. 43. Analysis of 5'LINE complementary and partially complementary sequences in the pKaede-MN1 plasmid with insert. (SEQ ID NO: 2)

FIG. 44. Analysis of TIS complementary and partially complementary sequences in the pKaede-MN1 plasmid with insert. (SEQ ID NO: 3)

Figure 45:
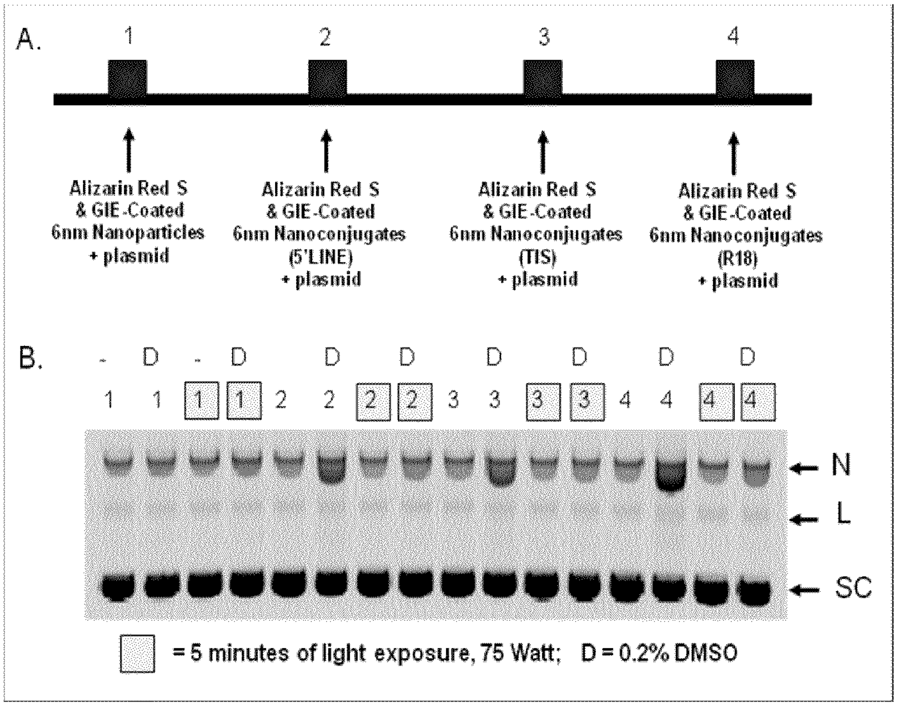

FIG. 45. A) Samples exposed to either no light or light and no DMSO or DMSO. B) Plasmid cleavage resulting from excitation of alizarin red s and GIE-coated PNA-$TiO_2$ nanoconjugates is due to release of reactive oxygen species. SC=supercoiled, N=nicked, L=linearized.

Figure 46:
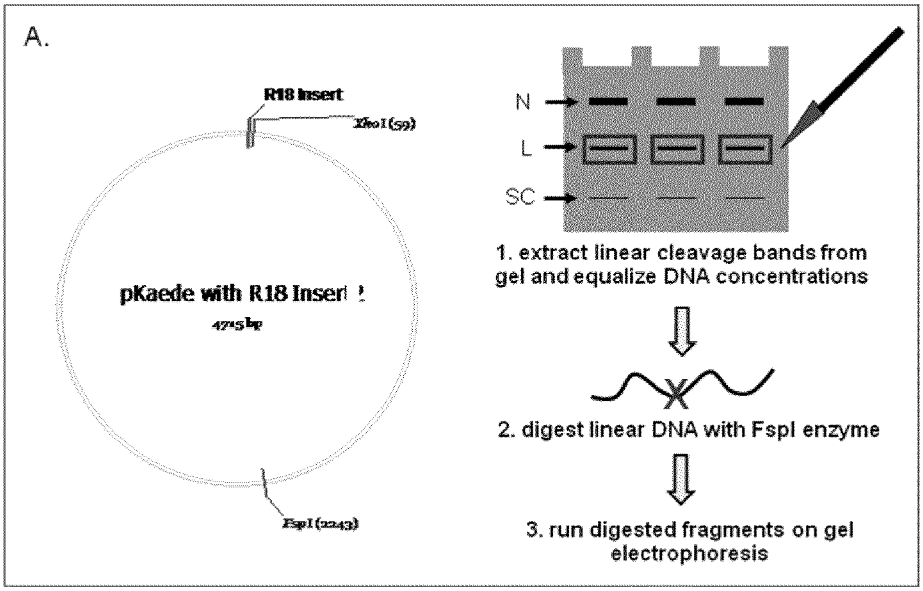

FIG. 46. A) (Left) Schematic of pKaede MN1 plasmid with R18 insert depicting predicted site of nanoconjugate hybridization and XhoI and FspI restriction enzyme cleavage sites. (Right) Summary of procedure to elucidate specificity of cleavage.

Figure 47:
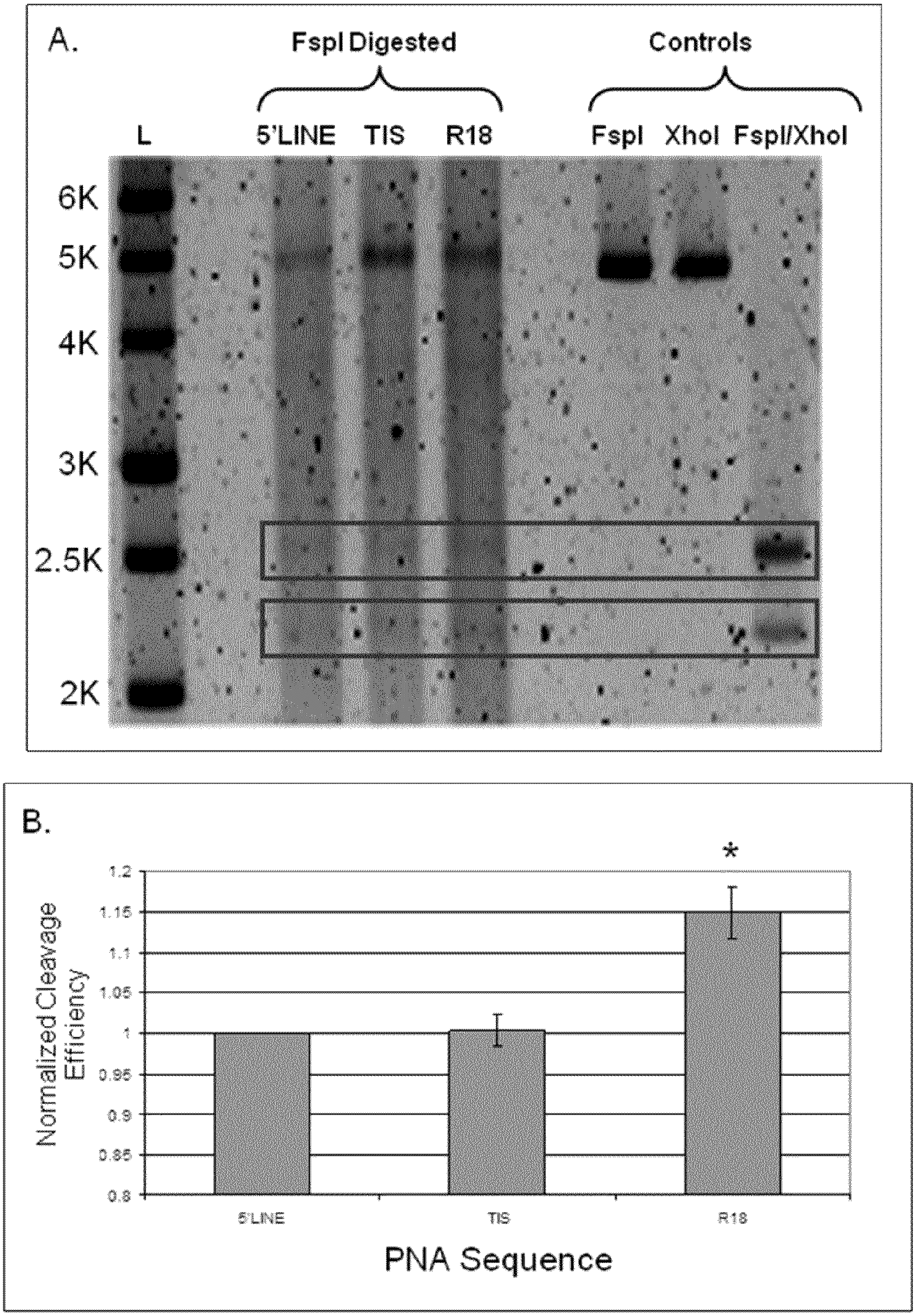

FIG. 47. Assay shown in FIG. 46. A) Gel electrophoresis indicating the effect of PNA sequence on cleavage products induced by excited GIE-alizarin red s-coated PNA-$TiO_2$ nanoconjugates. (three different PNA sequences shown) B) Quantitative summary of cleavage/digest results from three independent experiments. *=$p<0.01$ FIG. 48. Synthesis of the contrast agent used in Example 7. The first step of the reaction (i) was done in the presence of NaOH, in dimethylaminopyridine and N,N'-dimethylformamide overnight at 18-26° C. The second step of the reaction was done with gadolinium (iii) acetate at pH –5-5.5 at 18-26° C. for 24 hours, followed by the addition of disodium EDTA to remove excess $GD^{3+}$ ions (x=0.03, y=0.12, and z=0.85).

Figure 49:
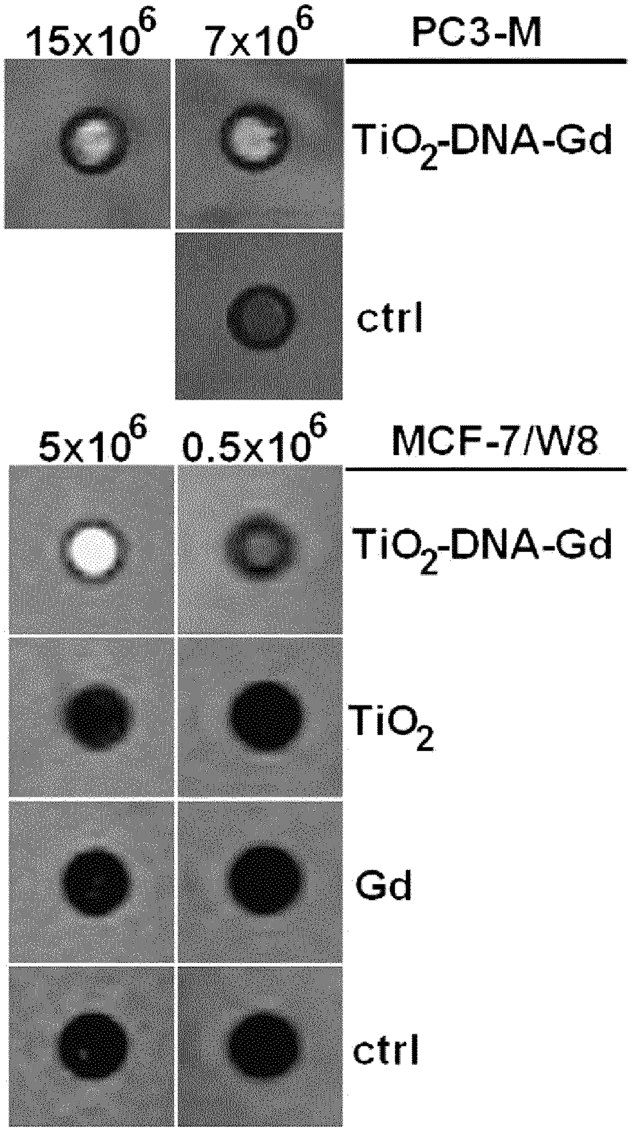

FIG. 49. A T1-weighted image of samples containing PC3-M (transfected by electroporation) and MCF-7 cells (transfected by SuperFect reagent) treated with $TiO_2$-DNA-Gd, $TiO_2$, Gd contrast agent, or nothing (control).

Figure 50:
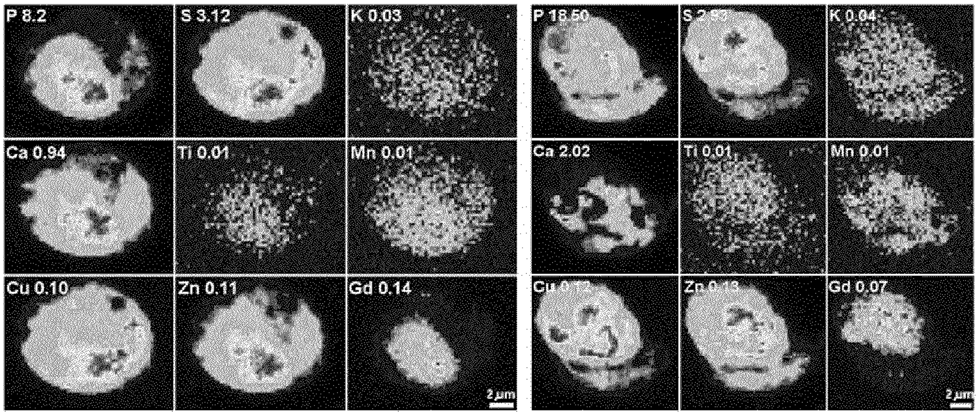

FIG. 50. X-ray fluorescence maps of two whole MCF-7/WS8 cells transfected with $TiO_2$-DNA oligonucleotide-Gd contrast agent nanoconjugates.

Figure 51:
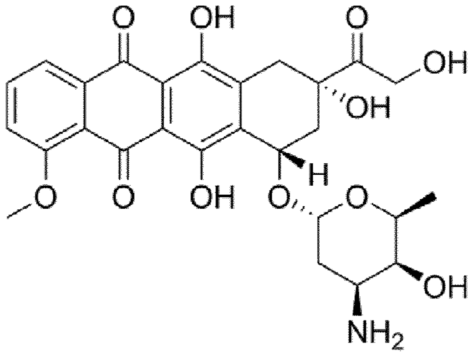

FIG. 51. Structure of Doxorubicin.

Figure 52:
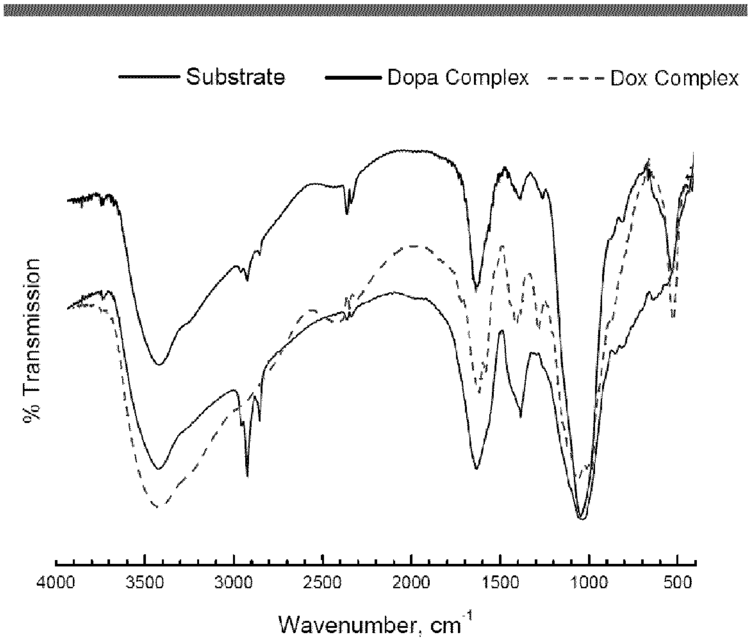

FIG. 52. Infrared spectrometry of nanoconjugates with doxorubicin.

Figure 53:
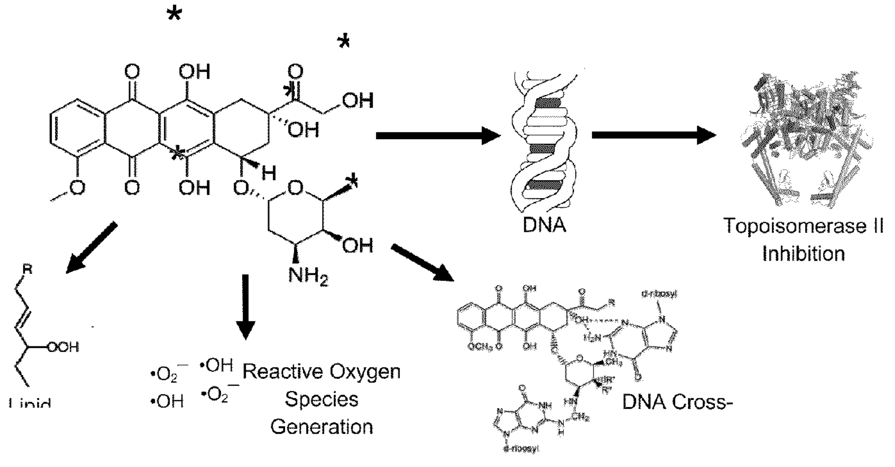

FIG. 53. Schematic of nanoconjugate destruction of nucleic acids.

Figure 54:
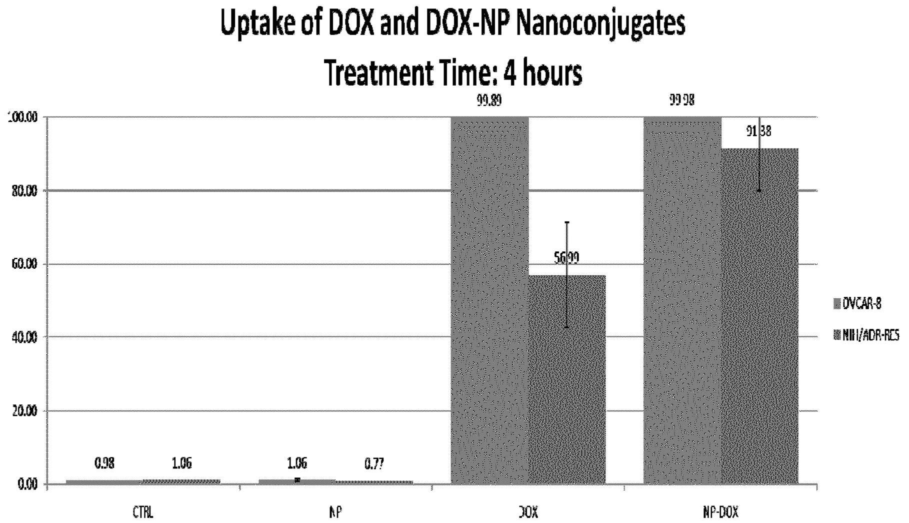

FIG. 54. Cellular uptake of nanoconjugates.

Figure 55:
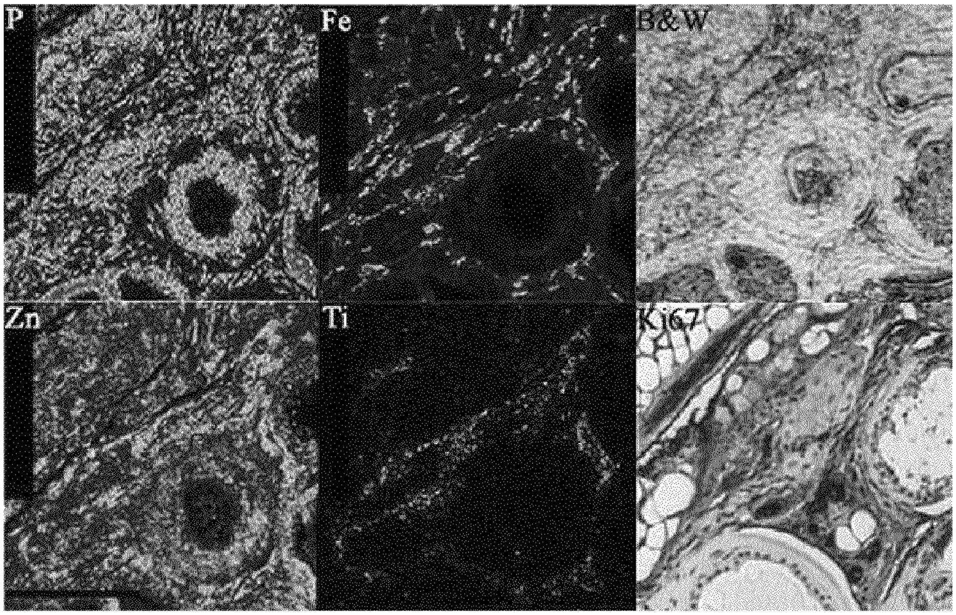

FIG. 55. Multifunctional images of prostate cancer after 8 nm of $Fe_3O_4@TiO_2$ with glucose being injected inside mice.

DEFINITIONS

As used herein, the term "agent" refers to a composition that possesses a biologically relevant activity or property. Biologically relevant activities are activities associated with biological reactions or events or that allow the detection, monitoring, or characterization of biological reactions or events. Biologically relevant activities include, but are not limited to, therapeutic activities (e.g., the ability to improve biological health or prevent the continued degeneration associated with an undesired biological condition), targeting activities (e.g., the ability to bind or associate with a biological molecule or complex), monitoring activities (e.g., the ability to monitor the progress of a biological event or to monitor changes in a biological composition), imaging activities (e.g., the ability to observe or otherwise detect biological compositions or reactions), and signature identifying activities (e.g., the ability to recognize certain cellular compositions or conditions and produce a detectable response indicative of the presence of the composition or condition). The agents of the present invention are not limited to these particular illustrative examples. Indeed any useful agent may be used including agents that deliver or destroy biological materials, cosmetic agents, and the like.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain by virtue of the well established genetic code. The DNA sequence thus codes for the amino acid sequence.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency or an oligonucleotide and/or mRNA based microarray. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.). Furthermore, when used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization, in *Nucleic Acid Hybridization* (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 5×SSPE, 0.1% SDS at 42 C when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length.

One skilled in the relevant art understands that stringency conditions may be altered for probes of other sizes (See e.g., Anderson and Young, Quantitative Filter Hybridization, in *Nucleic Acid Hybridization* (1985) and Sambrook et al., Molecular Cloning: A Laboratory Manual, Cold Spring Harbor Press, NY (1989)).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.* 2: 482 (1981)) by the homology alignment algorithm of Needleman and Wunsch (Needleman and Wunsch, *J. Mol. Biol.* 48:443 (1970)), by the search for similarity method of Pearson and Lipman (Pearson and Lipman, *Proc. Natl. Acad. Sci.* (*U.S.A.*) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acids include, by way of example, such nucleic acid in cells ordinarily expressing the gene where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

The term "recombinant DNA molecule" as used herein refers to a DNA molecule that is comprised of segments of DNA joined together by means of molecular biological techniques.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

As used herein, the term "purified" or "to purify" refers to the removal of contaminants from a sample. For example, antibodies are purified by removal of contaminating non-immunoglobulin proteins; they are also purified by the removal of immunoglobulin that does not bind the target protein. The removal of non-immunoglobulin proteins and/or the removal of immunoglobulins that do not bind the target protein results in an increase in the percent of target reactive immunoglobulins in the sample.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The present invention relates to nanoconjugates. In particular, the present invention provides nanoconjugates for diagnostic (e.g., imaging), research, and clinical (e.g., targeted treatment) applications.

Embodiments of the present invention provide multifunctional nanoconjugates for magnetic resonance imaging (MRI), computed tomography (CT) imaging, optical fluorescent imaging, and cell membranes targeting/penetration (e.g., cancer therapy). Compositions of embodiments of the present invention can be used either individually or simultaneously for all applications. No such multi-purpose agents currently exist based on the nanomaterial composition. Moreover, specific targeting and retention of the nanomaterial is achieved. The compositions and methods described herein therefore provide new combinations of diagnostic and therapeutic modalities and new diagnostic uses due to extended retention of the contrast agent.

I. Nanomaterials

Figure 1:
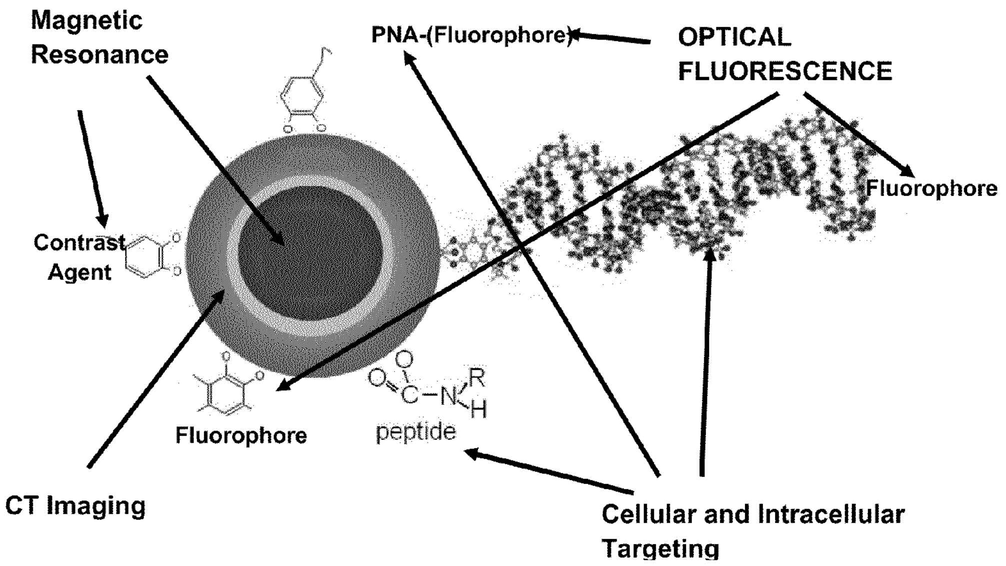
FIG. 1. Exemplary scheme of the multifunction nanoconjugates.

Embodiments of the present invention provide multifunctional nanoconjugates. Multifunctional nanoconjugates prepared in embodiments of the present invention are core-shell nanoparticles conjugated/coated with different (bio) molecules and different conjugation chemistries, for example, as shown in FIG. 1.

In some embodiments, the multi-layer structure of the nanoconjugate includes:

A nanomaterial which includes a magnetic nanocomponent coated by a single or multiple layer(s) of non-toxic metal oxide(s), with or without inclusion of quantum dot materials; completed by a bio-inert surface coating with or without addition of bioactive polymers or bio-molecules, depending on the different application purposes.

In some embodiments, the magnetic nanocomponent in the nanomaterials in a material that exhibits diamagnetism, ferrimagnetism, ferromagnetism, paramagnetism, superdiamagnetism, or superparamagnetism nanomaterials. In some embodiments, the magnetic nanocomponent introduces changes in $T_1$ and/or $T_2$ relaxation time to offer a high-contrast effect for MRI.

In some embodiments, the magnetic nanocomponent in the nanomaterial is a precursor for $\alpha$-$Fe_2O_3$, $\gamma$-$Fe_2O_3$ or related nanoalloy oxides with Fe after oxidization or for bcc-Fe or alloys-based Fe nanocomponents after reducing. The magnetic nanocomponent in the nanomaterials based on iron oxide can be extended to other iron oxide based nanomaterials, including, but not limited to, $MFe_2O_4$, $RFeO_3$, and MRFeOx (M=Ba, Bi, Co, Cr, Cu, Fe, Mg, Mn, Ni, Ti, Y, Zn) (R=rare earth metal elements) nanomaterials, and iron oxide coated various nanomaterials. In some embodiments, nanomaterials are $TiO_2$ nanoparticles.

The size of the completed nanomaterials in at least one dimension is preferably within 0.1-1000 nm. The shape of the nanomaterials may be regular (column, cube, cylinder, pillar, pyramid, rod, sphere, tube etc.) or irregular/random. The shape of the nanomaterials is controlled by adjusting the reaction dynamics and aging/ripening time.

II. Nanoconjugates

In some embodiments, nanomaterials are conjugated to materials to aid in targeting and imaging. In some embodiments, conjugates provide a bio-inert surface coating that provides nanomaterials with the ability to evade cellular uptake by cell types that are not targeted by bio-active (e.g., targeting) agent. In some embodiments, conjugates include a bio-active surface coating components to provide cell/tissue type specific targeting and/or extended retention of nanomaterial at the target site.

A. Contrast Agents

In some embodiments, the non-magnetic nanocomponent in the nanomaterials to be used as contrast agent for X-ray/CT, or MRI utilizes photoactive properties, absorbance for X-rays or paramagnetic properties for T1 magnetic resonance imaging. Exemplary contrast agents include, but are not limited to, Gadolium contrast agents, fluorescent agents (e.g., Alizarin Red S), and contrast agents described in U.S. Pat. No. 7,412,279 or 6,540,981, each of which is herein incorporated by reference in its entirety.

In some embodiments, nanoconjugates serve as a multimodal imaging agent and therapeutic agent; moreover, when excited by white light (Paunesku et al., Nat. Mater. 2003, 2, 343-346), these nanoconjugates have the ability to cleave DNA.

In some embodiments, the nanocomponent of the nanomaterials with function to provide contrast for imaging may be a monolayer (single component) or multiple layers (core-shell structures, core-corona-shell structures, or onion structures) of materials with photoactive properties: e.g., semiconductor metal oxides and/or quantum dots materials composed of II-VI members in the periodic table of elements. In some embodiments, the components of semiconductor metal oxides are of $M_xO_y$ composition, including but not limited to, $TiO_2$, ZnO, $ZrO_2$, $SiO_2$ etc. The components of quantum dots in the nanomaterials may be Group II-VI members of the periodic table of elements, for example ZnS, ZnSe, ZnTe, ZnPo, SiC, BN, AlN, and GaN etc.

B. Biological Molecules

In some embodiments, the nanoconjugates include biological materials (e.g., to serve as bio-active targeting agents). The bio-active surface coating components include, but are not limited to, peptides, lipids, carbohydrates, nucleic acids and their derivatives (PNAs, LNAs etc.). In some embodiments, bio-active components are attached to the nanoparticle surface via covalent bonds. These components of nanomaterial can provide cell type specific targeting. For example, nucleic acids (DNA, PNA oligonucleotides) coatings provide cell type specific targeting. Peptide coating allows targeting/penetration of cell membranes.

The bio-active surface coating components can be attached to the core-shell nanoparticles by direct covalent bonding, or via functional ligands which also serve as an “electronic link” between these two nanocomposites components (as referenced in U.S. Pat. No. 6,677,606 B1, herein incorporated by reference in its entirety). Such ligands preferably have groups with varying donor acceptor character, selective binding of desired bio-active molecules (e.g., intracellular or extracellular targets), and components for the binding to the surface of the nanoparticles. Examples of the binding ligands include, but are not limited to, bidentate enediols, such as dopamine.

In one embodiment of the present invention, the nucleic acid probe hybridizes to a nucleic acid target sequence on a subject nucleic acid and forms a stem-loop structure when not bound to the nucleic acid target sequence. In another embodiment, the nucleic acid probe hybridizes to a nucleic acid target sequence on a subject nucleic acid and has a linear or randomly coiled structure when not bound to the nucleic acid target sequence. In yet another embodiment, the nucleic acid probe comprises a modification of the nucleic acid backbone. The invention further provides that these methods may comprise the use of a nucleic acid probe that incorporates a resonance energy transfer moiety.

In certain other embodiments of the present invention, several nanoprobes (e.g., 4-6) are hybridized on the same target. This leads to an increased sensitivity and signal-to-noise ratio. In other embodiments, each magnetic nanoprobe comprises a hairpin probe and two magnetic nanoparticles at the end of the stem.

In some embodiments, the present invention provides nanoparticles with attached DNA oligonucleotides that assemble into a 3D mesh structure by allowing base pairing between oligonucleotides. A change of the ratio of DNA oligonucleotide molecules and nanoparticles regulates the size of the mesh as characterized by UV-visible light spectra, transmission electron microscopy and atomic force microscopy images.

In some embodiments, to prepare ssDNA-nanoconjugates, a connector (e.g., dopamine) between the nanoparticle and the DNA oligonucleotide is used. In some embodiments, in order to create nanoconjugate assemblies, the process of temperature sensitive DNA oligonucleotide hybridization is controlled to regulate the number of nanopaticles participating in the assembly.

In some embodiments, nanoconjugate superstructures are formed by generating nanoconjugates with complementary ssDNA sequences. The ratio of between DNA oligonucleotides and nanoparticles determines which superstructures are formed between nanoconjugates carrying complementary DNA sequences. A low oligonucleotide per nanoparticle loading results in formation of simple dumbbell structures with no more than several nanoparticles, while nanoparticles with high oligonucleotide loading assemble into complex 3D structures.

In some embodiments, nanoparticles comprise surface coatings (e.g., to improve uptake and retention, reduce toxicity, or improve targeting). For example, in some embodiments, nanoconjugates are coated with folic acid or glucose.

Nucleic acid-nanoparticle nanoconjugates hybridize to target DNA and enable sequence-specific detection through numerous imaging modalities. In some embodiments, multiplexing the imaging and therapeutic capacities of such nanoconjugates is used in simultaneous detection and removal of deleterious DNA sequences. In some embodiments, nanoconjugates are used to induce enhanced DNA damage in a sequence specific manner.

In some embodiments, nanoparticles are conjugated to PNAs. The present invention is not limited to a particular mechanism. Indeed, an understanding of the mechanism is not necessary to practice the present invention. Nonetheless, it is contemplated that replacing DNA with PNA or similar DNA analogs will lead to increased stability of the nucleic acid component of the nanoconjugate and will, therefore, prolong targeting life of the nanoconjugates and increase sequence selectivity. PNA/PNA binding affinity is extremely thermostable.

It is well established in the literature that PNAs have longer half-life in vivo and intracellularly compared to DNAs (McMahon et al., Antisense Nucleic Acid Drug Dev. 2002, 12, 65-70). However, the same body of research established that PNAs are not as soluble as DNAs and that some PNA sequences have proved difficult to synthesize in the past. The later issues have since been circumvented with the development of automated synthesis protocols (Mayfield et al., Anal. Biochem. 1999, 268, 401-404); while challenges of solubility and delivery of PNAs into cells were solved by new solubilization strategies For example, PNAs can be annealed to a negatively charged DNA oligonucleotide and complexed with cationic lipids for intracellular delivery (Braasch et al., Methods. 2001, 23, 97-107; Herbert et al., Proc. Natl. Acad. Sci. U.S.A. 1999, 96, 14276-14281). Alternative methods of intracellular delivery of PNAs include synthesis of a PNA with a nuclear localization signal (NLS) (Braun et al., J. Mol. Biol. 2002, 318, 237-243), electroporation (Karras et al., Biochemistry (Mosc). 2001, 40, 7853-7859; Shammas et al., Oncogene. 1999, 18, 6191-6200), and microinjection. The studies shown here, however, suggest that in the context of $PNA-TiO_2$ nanoconjugates, many different molecules can be attached to the nanoparticle part of the nanoconjugate (and in multiple copies) to increase cellular uptake and retention of nanoparticle conjugated PNAs.

In some embodiments, nanoconjugates comprise protein (e.g., peptide or antibody) targeting moieties. In some embodiments, protein targeting moieties are used to localize nanoconjugates to specific locations in the body (e.g., tumors). In other embodiments, peptides or proteins are used to facilite cellular uptake or retention of nanoconjugates an direct them to different cellular or subcellular locations inside cells.

C. Therapeutic Agents

In some embodiments, nanoconjugates comprise therapeutic agents. In some embodiments, the therapeutic agents are known chemotherapeutic agents. A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-$\alpha$) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In some embodiments, anticancer agents comprise agents that induce or stimulate apoptosis. Agents that induce apoptosis include, but are not limited to, radiation (e.g., X-rays, gamma rays, UV); tumor-derived growth factor ligands, receptors, and analogs; kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycoformycin)).

In still further embodiments, chemotherapeutic agents suitable for use in the compositions and methods of the present invention include, but are not limited to: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 3 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 3

| | | |
|---|---|---|
| Aldesleukin<br>(des-alanyl-1, serine-125 human interleukin-2) | Proleukin | Chiron Corp., Emeryville, CA |
| Alemtuzumab<br>(IgG1κ anti CD52 antibody) | Campath | Millennium and ILEX Partners, LP, Cambridge, MA |

TABLE 3-continued

| | | |
|---|---|---|
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N",N",-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl]benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy- | Cerubidine | Wyeth Ayerst, Madison, NJ |

TABLE 3-continued

| | | |
|---|---|---|
| (alpha)-L-lyxo-hexopyranoside hydrochloride) | | |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}\bullet(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal | Zevalin | Biogen IDEC, Inc., Cambridge MA |

TABLE 3-continued

| | | |
|---|---|---|
| antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | | |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene)dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S$•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |

TABLE 3-continued

| | | |
|---|---|---|
| Oxaliplatin (cis-[(1R,2R)-1,2-cyclohexanediamine-N,N'][oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)—N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine)butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4'':6,7]indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |

TABLE 3-continued

| | | |
|---|---|---|
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10}•H_2SO_4$) | Velban | Eli Lilly |
| Vincristine ($C_{46}H_{56}N_4O_{10}•H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCl-779, CDB-2914, cefixime, cetuximab, CGO070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflomithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hul4.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafamib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpimase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifamib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Eds. Hardman et al., 2001.

In addition, the oxygen-photosensitizing substances such as alizarin red s, purpurin etc. are often enediol bidentate ligands which readily bind to $TiO_2$ nanoparticle/nanoparticle shell surfaces. Since many photosensitizers of pharmaceutical interest for photodynamic therapy (PDT) are hydrophobic (See e.g., Siggel et al. J. Phys. Chem. 100 (12): 2070-2075, December 1996), they frequently utilize carriers which can provide enhanced solubility. This allows for the additional application of multifunctional nanoparticles for photodynamic cancer therapy.

III. Uses

The nanoconjugates described herein find use in a variety of research, imaging, diagnostic, and therapeutic applications. Examplary applications are described herein.

In some embodiments, nanoconjugates are utilized in imaging (e.g., in vivo imaging) applications. For example, as described herein, in some embodiments, nanoconjugates comprise contrast agent for imaging (e.g., X-Ray, computer tomography (CT) imaging, or MRI imaging). In some embodiments, nanoconjugates for imaging comprise targeting moieties (e.g., nucleic acids, PNAs, peptides, proteins, antibodies, etc.) that target the conjugates to a region of interest (e.g., tumor). In some embodiments, imaging nanoconjugates further find use in targeted therapeutic applications (see below discussion of therapeutic applications).

In some embodiments, nanoconjugates are used in therapeutic applications (e.g., cancer therapies). For example, in some embodiments, targeting moieties on nanoconjugates are used to target the nanoconjugate to a tumor subcellular location (e.g., an oncogene). In some embodiments, the nanoconjugate further comprises an imaging component to identify and visualize the tumor. In some embodiments, nucleic acid targeting moieties are used for sequence specific hybridization (e.g., to a tumor specific oncogene or other cancer marker molecule), while the nanoparticle component maintains its photocatalytic properties (Paunesku et al., 2003, supra; Rajh et al., Nano Lett. 2004, 4(6), 1017-1023). In some embodiments, when photo-activated, a charge separation occurs within the nanoparticle, resulting in the migration of an electropositive hole (h+) from the nanoparticle, through any linker, and onto the DNA (Rajh et al., Nano Lett. 2004, 4(6), 1017-1023 Liu et al., Chem. Phys. 2007, 339(1-3), 154), resulting in its scission. Thus, in some embodiments, nanoconjugates specifically target oncogenes that represent desirable therapeutic targets (e.g. ras, myc) (Weinstein et al., Nat Clin Pract Oncol 2006, 3(8), 448-457; Wang et al., Breast Cancer Res 2005, 7(2), R220-228; Felsher, Nat Rev Cancer 2003, 3(5), 375-380; Chin et al., Nature 1999, 400(6743), 468-472).

In some embodiments, photosensitive dyes (e.g., conjugated to or coating nanoconjugates) that release reactive oxygen species upon excitation by light are used to both image and destroy DNA (e.g., oncogenes). In some embodiments, the dyes can also be used for imaging (e.g., via fluorescence). One non-limiting example of a dye suitable for use in such methods is Alizarin red s. In some embodiments, nanoconjugates further comprise targeting moieties (e.g., nucleic acids or PNAs) that allow for sequence specific cleavage of DNA.

In some embodiments, tumor specific therapy is performed in conjunction with MRI imaging. For example, in some embodiments, $^{157}$Gd or other suitable agent coats nanoconjugates. The agent is brought into close proximity with the primary target (e.g., nuclear DNA) using a targeting moiety. Neutron capture therapy is then used to destroy tumor tissue. Neutron capture therapy leads to local production of high-linear energy transfer radiation, with subsequent production of Auger electrons. Because of target-dependent retention of nanoconjugate-associated agent, if neutron capture is performed, target cells are most affected by this treatment, whereas normal tissues suffer very limited radiation damage.

In some embodiments, nanoconjugates are used to target drugs (e.g., chemotherapy drugs or photosensitizers) to a particular site in the body or inside cells. For example, in some embodiments, nanoconjugates comprise a targeting moiety and a therapeutic agent. The therapeutic agent is specifically targeted to the area in need of treatment (e.g., tumor), thus increasing the concentration of drug at the tumor site and decreasing the concentration at healthy cells and consequently decreasing side effects.

In some embodiments, nanoconjugates are used in research (e.g., imaging in animal models, structural studies, DNA-protein binding interactions, protein capture, etc.) or drug screening applications.

EXPERIMENTAL

The following examples are provided in order to demonstrate and further illustrate certain preferred embodiments and aspects of the present invention and are not to be construed as limiting the scope thereof.

Example 1

Core Nanoparticle Preparation

Figure 2:
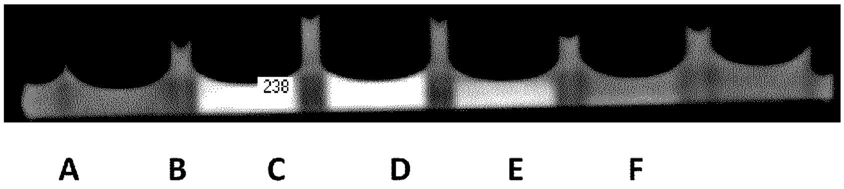
FIG. 2. CT images of Rutile type of 10*40 nm of needle-like $TiO_2$-nanomaterials (B, C, D). The A, E, and F columns are water as a reference.

Particles a-d were purchased from commercial sources to use as controls.

a) 6 nm of anatase type of $TiO_2$ as the nanomaterials with photoactive properties for CT. 10*40 nm of rutile type of $TiO_2$ as the nanomaterials with photoactive properties for CT. CT images of Rutile type of 10*40 nm of needle-like $TiO_2$-nanomaterials are shown in FIG. 2.

b) 10 nm of $ZrO_2$ with bridging ligand-dextrans as the nanomaterials with photoactive properties for CT.

c) 8 nm of ZnO with bridging ligand-liposome as the nanomaterials with photoactive properties for CT.

d) 6 nm of ZnS with bridging ligand-liposome as the nanomaterials with photoactive properties for CT.

e) Preparation of 3 nm of $\alpha$-$Fe_2O_3$ nanocrystal in aqueous solution and subsequent preparation of 30 nm of $\alpha$-$Fe_2O_3$@$TiO_2$ nanocrystal.

1) 3 g of anhydrous $FeCl_3$ crystal salt was dissolved in 1 M HCl solution and kept in a final volume of 100 mL, the concentration of $FeCl_3$ was 3%.

2) 10 mL of as prepared $FeCl_3$ of 3% in 1 M HCl solution was rapidly injected into the hot water (90 mL) with fiercely stirring and reacted for 12-20 min.

3) Half of reacted solution ($\alpha$-$Fe_2O_3$ nanocrystal) without glycidyl isopropyl ether (GIE) was coated and incubated at 50-70° C. for 24 hours. Half of reacted solution ($\alpha$-$Fe_2O_3$ nanocrystal) was coated using 100 μL of 98% GIE for 15-45 min and incubated at 50-70° C. for 24 hours.

Preparation of 30 nm of $\alpha$-$Fe_2O_3$@$TiO_2$ Nanocrystal in Aqueous Solution 1) The as prepared 3 nm of $\alpha$-$Fe_2O_3$ nanocrystal was filtered using filter paper to remove the precipitation as a mother-seed solution.

2) 25 mL as prepared 3 nm of $\alpha$-$Fe_2O_3$ nanocrystal was diluted into 100 mL of 0.1 M HCl solution after filtering and injecting slowly 7 mL of ~0.1 M $TiCl_4$ in 20% HCl solution with vigorous stirring. The reacting solution was cooled by ice-water mixture.

3) The reaction was kept 8 hours. Half of the reacted solution stored at 4° C. and the other solution using 100 μL of 98% GIE coated 15-45 min before being stored at 4° C.

f) Preparation of 2 nm of $CoFe_2O_4$ nanocrystal in aqueous solution and subsequent preparation of $CoFe_2O_4$@$TiO_2$ nanocrystal.

1) 20 mL of 100 mM $Co(NO_3)_2.6H_2O$ aqueous solution and 20 mL of 200 mM $Fe(NO_3)_3.9H_2O$ aqueous solution were mixed with 40 mL of pure water firstly.

2) 20 mL of 300 mM citric acid aqueous solution was quickly added into the as-mixed solution with stirring at room temperature. After reacting 1 hour, a burnt orange solution was obtained. All mixture solutions appeared clear and did not exhibit any phase separation.

3) One of half prepared solution coated was carried out by adding 0.657 mmol 98% of GIE for reacting 30-60 min.

4) Both of the uncoated and coated sample solutions were allowed to gel in static air at 30-50° C. in a water-oven for 24 hours.

Preparation of 6 nm of $CoFe_2O_4$@$TiO_2$ Nanocrystal in Aqueous Solution 1) 2.5 mL of ~0.1 M $TiCl_4$ in 20% HCl slowly mixed with 25 mL as-prepared 2 nm of $CoFe_2O_4$ nanocrystal without GIE coated with vigorous stirring in 22.5 mL of pure water. The total volume of the sample solution was 50 mL. The reacting solution was cooled by ice-water mixture.

2) The sample solution from burnt orange to bronze when the sample solutions were mixed. The reaction was kept 6 hours. Half of the reacted solution stored at 4° C. and the other solution using 43 μL of 98% GIE coated 30-60 min before being stored at 4° C.

6 nm of $CoFe_2O_4$@$TiO_2$ was synthesized and tested in vitro as the nanomaterial for contrast agents of both MRI and CT. These nanoparticles were tested for MR in cells in culture, and their uptake was tested in cultured cells. Also, 6 nm of $CoFe_2O_4$@$TiO_2$ was used as a contrast agent for both MRI and CT. The $CoFe_2O_4$@$TiO_2$ was injected into experimental animals with significant image-enhancing effects on the liver.

Figure 3:
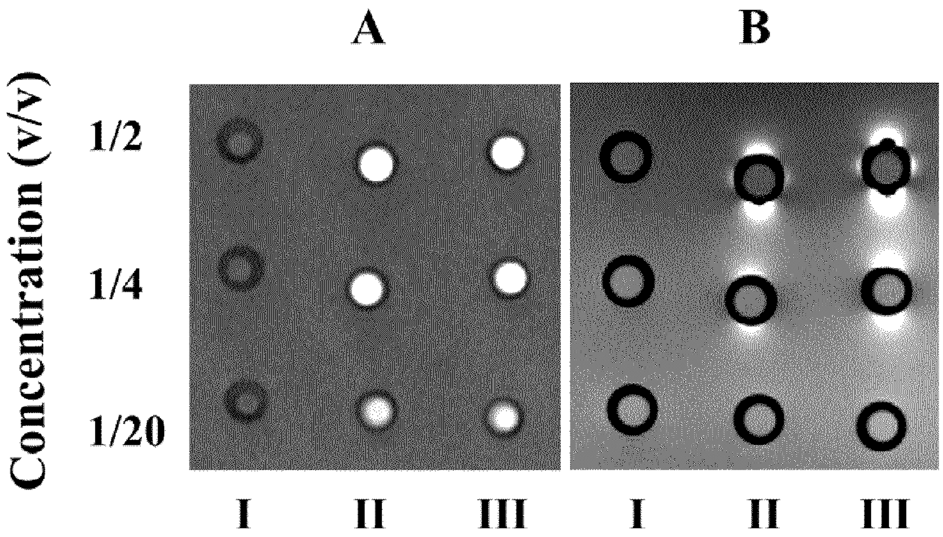
FIG. 3. MRI images of 6 nm of core-shell particulate $CoFe_2O_4$@$TiO_2$ (column II). $T_1$-weighted (A) and off-resonance-weighted (B) magnetic resonance images. The images were acquired at three different concentrations (½ (top row), ¼ (middle row), and 1/20 (bottom row); all concentrations are v/v) of stock solutions I ($TiO_2$), II ($CoFe_2O_4$@$TiO_2$), and III ($CoFe_2O_4$). In subfigure A, the solutions containing cobalt iron oxides (II and III) are hyper-intense due to $T_1$ enhancement, while the solution free of cobalt iron oxides, $TiO_2$ solutions (I), is iso-intense with the background. In subfigure B, note the presence of off-resonance effects mediated by the solutions containing cobalt iron oxides (II and III) at higher concentrations (½ and ¼) outside the tubes (in water), while the solutions containing the lowest amount of cobalt iron oxides (1/20) and free of cobalt iron oxides (I) do not show any off-resonance-weighted signal enhancements.
Figure 4:
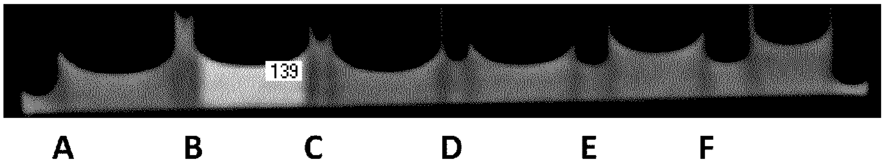
FIG. 4. MRI images of $T_1$-weighted 20 nm of core-corona-shell particulate $CoFe_2O_4$@Au@$TiO_2$ without GIE coating (Spot D) and with GIE coating (Spot E). The Spot A is water as a reference. 6 nm of particulate $TiO_2$ without GIE coating (Spot B) and with GIE coating (Spot C) are also as references.
Figure 5:
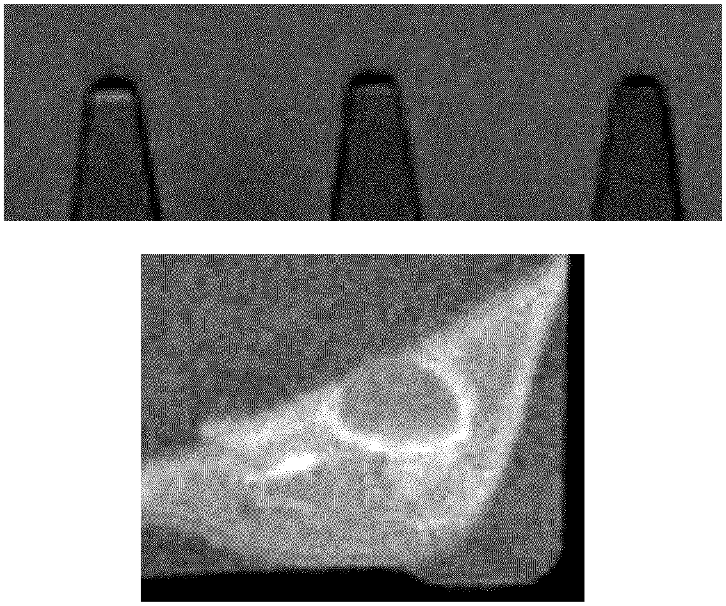
FIG. 5. Top panel: a) 5 million cells treated with $CoFe_2O_4$@$TiO_2$ nanoparticles; b) 1 million cells treated with nanoparticles; c) 1 million control cells. Bottom panel: MR image ex vivo of rabbit liver tumor adjacent to which 6 nm of core-shell particulate $CoFe_2O_4$@$TiO_2$ nanomaterials was injected.

6 nm of $CoFe_2O_4$@$TiO_2$ with bridging ligand-liposome as the nanomaterials with photoactive properties for CT. The signals for both CT and MRI within one nanomaterial ensemble simultaneously are shown in FIG. 3 and FIG. 4. MR image of the cultured cells and the liver ex-vivo treated with $CoFe_2O_4$@$TiO_2$ nanomaterial are presented in FIG. 5.

6 nm of $CoFe_2O_4$@$TiO_2$ as the magnetic nanocompositions for MRI. Glucose coated 6 nm $CoFe_2O_4$@$TiO_2$ as the magnetic nanocompositions was injected into experimental animals with significant image-enhancing effects on breast tumors in mice.

g) Preparation of 10 nm of $CoFe_2O_4$@Au core-shell nanocrystal materials in aqueous solution (1) 20 mL of 100 mM $Co(NO_3)_2.6H_2O$ aqueous solution and 20 mL of 200 mM $Fe(NO_3)_{3-9}H_2O$ aqueous solution were mixed with 40 mL of pure water firstly.

(2) 20 mL of 300 mM citric acid aqueous solution was quickly added into the as-mixed solution with stirring at room temperature. After reacting 1 hour, a burnt orange solution was obtained. All mixture solutions appeared clear and did not exhibit any phase separation.

(3) One of half prepared solution coated was carried out by adding 0.657 mmol 98% of GIE for reacting 30-60 min.

(4) Both of the uncoated and coated sample solutions allowed to gel in static air at 30-50° C. in a water-oven for 24 hours.

(5) 1 mL of 10 mM $HAuCl_4.3H_2O$ (Sigma, MW=393.83) aqueous solution was added to 1 mL as-prepared 2 nm of $CoFe_2O_4$ nanocrystal+96 mL double distilled water (18.2 MΩ) with vigorous stirring to mix.

(6) 1 mL of 30 mM citric acid (MW=192.12, Sigma-Aldrich, 99.5%) was rapidly injected into the mixed solution. The citric acid anions acted as protected agents on the surface of the as-prepared gold nanocrystals.

(7) mL of ~0.1 M freshly prepared aqueous sodium borohydride ($NaBH_4$) solution was added to the solution all at once with vigorous stirring.

(8) The final total volume was ~100 mL. 50 mL of the reacted solution stored at 4° C. and the other 50 mL solution using 1 μL of 98% GIE coated 15-30 min before being stored at 4° C.

Preparation of 18 nm of $CoFe_2O_4$@Au Core-Shell Nanocrystal Materials in Aqueous Solution (1) 20 mL of 100 mM $Co(NO_3)_2.6H_2O$ aqueous solution and 20 mL of 200 mM $Fe(NO_3)_{3-9}H_2O$ aqueous solution were mixed with 40 mL of pure water firstly.

(2) 20 mL of 300 mM citric acid aqueous solution was quickly added into the as-mixed solution with stirring at room temperature. After reacting 1 hour, a burnt orange solution was obtained. All mixture solutions appeared clear and did not exhibit any phase separation.

(3) One of half prepared solution coated was carried out by adding 0.657 mmol 98% of GIE for reacting 30-60 min.

(4) Both of the uncoated and coated sample solutions allowed to gel in static air at 30-50° C. in a water-bath for 24 hours.

(5) 1 mL of 10 mM $HAuCl_4.3H_2O$ (Sigma, MW=393.83) aqueous solution was added to 1 mL as-prepared 2 nm of $CoFe_2O_4$ nanocrystal (Assumed diameter will be 2 nm, 123 (Co+Fe) atoms in total and 77 (Co+Fe) atoms on the surface of the nanocrystal)+97 mL (in fact the water volume is about 97 mL+20 mL=117 mL to compensate the evaporation of the solution due to the heating) double distilled water (18.2 MΩ) with vigorous stirring to mix.

(6) 1 mL of 30 mM citric acid (MW=192.12, Sigma-Aldrich, 99.5%) was rapidly injected into the mixed solution. The overdosed citric acid anions acted as protected agents on the surface of the as-prepared gold nanocrystals. Usually, the ratio of the [$HAuCl_4$]/[Citric Acid] was 1:3.

(7) The mixed solution color changed from orange-yellow to purple red and finally wine red within 10 min at 60-75° C. with vigorous stirring.

(8) The final total volume was 120 mL. The reaction was kept 15-20 min at 65° C. with vigorous stirring. The reacted solution was about pH=3.5. ~100 mL of the reacted solution stored at 4° C. and the other 20 mL solution using 1 L of 98% GIE coated 15-30 min before being stored at 4° C.

h) Synthesis of $Fe_3O_4$@$TiO_2$ $Fe_3O_4$ nanocrystal (core seed nanoparticle): First [Fe(II)+Fe(III)]/[Citric Acid]=1:2; [Fe(II)]/[Fe(III)]=1:2; [Cl]/[Citric Acid]=3:16 aqueous solution was mixed with pure water; secondly, citric acid (Sigma-Aldrich, 99.5%) aqueous solution was quickly added into the as-mixed solution with stirring at room temperature. At that time sample solutions was allowed to gel in static air at 40-80° C. in a water-bath for 24 hours.

$Fe_3O_4$@$TiO_2$ nanoparticles (complete core-shell nanoparticle): Firstly ~0.1 M of $TiCl_4$ in 20% HCl was slowly mixed with the as-prepared $Fe_3O_4$ nanoparticle with vigorous stirring in pure water. The reacting solution was cooled by incubation in ice-water mixture for 6 hours. Completed nanoparticles were stored at 4° C.

6 nm of $Fe_3O_4$@$TiO_2$ was synthesized and tested in vitro as the nanomaterial for contrast agents of both MRI and CT. Their uptake was tested in cultured cells.

8 nm of $Fe_3O_4$@$TiO_2$ with glucose as the magnetic nanocompositions for MRI. Water soluble of 8 nm of $Fe_3O_4$@$TiO_2$ with glucose as the magnetic nanocompositions was injected into experimental animals with significant image-enhancing effects on prostate tumors (FIG. 55).

8 nm of $Fe_3O_4$@$TiO_2$ was synthesized and tested in vitro as the nanomaterial for contrast agents of both MRI and CT.

Chemotherapeutic drugs were added onto the surface of these nanoparticles in order to be able to use them for diagnostic MR imaging and therapy at the same time. Doxorubicine was attached to nanoparticles (Example 8) and the efficiency of doxorubicine for cell killing in vitro was increased.

i) Preparation of 5 nm of Au@$TiO_2$ Core-Shell Nanocrystal Materials in Aqueous Solution (1) 2-3 mL of 10 mM $HAuCl_4.3H_2O$ (Sigma, MW=393.83) aqueous solution was added to 394 mL of double distilled water (18.2 MΩ) with vigorous stirring to mix.

(2) 2-3 mL of 30 mM citric acid (MW=192.12, Sigma-Aldrich, 99.5%) was rapidly injected into the mixed solution at 95° C. with vigorous stirring. The citric acid anions acted as protected agents on the surface of the as-prepared gold nanocrystals.

(3) mL of ~0.1 M freshly prepared aqueous sodium borohydride ($NaBH_4$) solution was added to the solution all at once with vigorous stirring.

(4) The mixed solution color changed from transparent to gray black then purple red and finally wine red within 1 min after the addition of $NaBH_4$ solution.

(5) Half of the reacted solution stored at 4° C. and the other solution using 5 μL of 98% GIE coated 15-30 min before being stored at 4° C.

(6) 25 mL of as-prepared gold nanocrystal without GIE coated with vigorous stirring in 24.95 mL of pure water.

(7) 50 uL of ~0.1 M $TiCl_4$ in 20% HCl solution was firstly added to the mixed solution into the mixed gold nanocrystal solution with vigorous stirring. The total volume of the sample solution was 50 mL. The reacting solution was kept at room temperature.

(8) The sample solution was from red wine waned after the first drop of $TiCl_4$ in 20% HCl solution being added and became transparent when the sample solutions were mixed within 10 min. The reaction was kept 3 hours. Half of the reacted solution stored at 4° C. and the other solution using 1 μL of 98% GIE coated 30-60 min before being stored at 4° C.

j) Preparation of 8.5 nm of Au@$TiO_2$ Core-Shell Nanocrystal Materials in Aqueous Solution (1) 2-3 mL of 10 mM $HAuCl_4.3H_2O$ (Sigma, MW=393.83) aqueous solution was added to 394 mL of double distilled water (18.2 MΩ) with vigorous stirring to mix.

(2) 2-3 mL of 30 mM citric acid (MW=192.12, Sigma-Aldrich, 99.5%) was rapidly injected into the mixed solution at 95° C. with vigorous stirring. The overdosed citric acid anions acted as protected agents on the surface of the as-prepared gold nanocrystals. Usually, the ratio of the [$HAuCl_4$]/[Citric Acid] was 1:3.

(3) The mixed solution color changed from transparent to gray black then purple red and finally wine red within 6 min.

(4) The reaction was kept 10 min at 95° C. with vigorous stirring. The reacted solution was at pH=3.5-4.0. Half of the reacted solution was stored at 4° C. and the other solution was coated using 5 μL of 98% GIE 15-30 min before being stored at 4° C.

(5) 25 uL of ~0.1 M $TiCl_4$ in 20% HCl firstly diluted to 1.5 mL in 37% HCl+1.0 mL water solution (6) 25 mL as-prepared gold nanocrystal solution without GIE coated with vigorous stirring in 22.5 mL of pure water. Then slowly adding mixed $TiCl_4$ solution into the mixed gold nanocrystal solution along with vigorous stirring. The total volume of the sample solution was 50 mL. The reacting solution was kept at room temperature.

(7) The color of the sample solution was red wine. The color waned after the first drop was added and became transparent within 10 min of the sample solutions being mixed.

(8) The reaction was kept for 3 hours and the final pH value was at pH=0.5-1.0. Half of the reacted solution stored at 4° C. and the other solution was coated using 1 μL of 98% GIE 30-60 min before being stored at 4° C.

k) Preparation of 18.5 nm of $CoFe_2O_4$@Au@$TiO_2$ Core-Corona-Shell Nanocrystal Materials in Aqueous Solution 1). Preparing $CoFe_2O_4$ Magnetic Nanocrystals (2 nm)

(1) 60 mL of 100 mM $Co(NO_3)_2.6H_2O$ (3*0.582 g, MW=291.03, Sigma-Fluka, >98%) aqueous solution and 60 mL of 200 mM $Fe(NO_3)_3.9H_2O$ (3*1.616 g, MW=404.00, Sigma-Aldrich, >99.8%) aqueous solution were mixed with 120 mL of pure water.

(2) 60 mL of 300 mM citric acid (3.456 g, MW=192.12, Sigma-Aldrich, 99.5%) aqueous solution was quickly added into the as-mixed solution with stirring at room temperature. After reacting 1 hour, a burnt orange solution was obtained. All mixture solutions appeared clear and did not exhibit any phase separation at pH=~1.0-1.5.

(3) [Co(II)+Fe(III)]/[Citric Acid]=1:1; [Co(II]/[Fe(III)]=1:2; [$NO_3^-$]/[Citric Acid]=3:8.

(4) The final total volume was 300 mL. One-third of prepared solution coated was carried out by adding 1.314 mmol of 98% of GIE (169.4 uL) and reacting for 30-60 min.

(5) Both of the uncoated and coated sample solutions allowed to gel in static air at 50° C. in a water-bath for 24 hours.

2). Preparing $CoFe_2O_4$@Au Core-Shell Nanocrystals (18 nm)

(1) 1 mL of 10 mM $HAuCl_4.3H_2O$ (Sigma, MW=393.83) aqueous solution was added to 1 mL of the as-prepared $CoFe_2O_4$ nanocrystal+97 mL (in fact the water volume is about 97 mL+20 mL=117 mL to compensate the evaporation of the solution during the heating) double distilled water (18.2 MΩ) with vigorous stirring to mix.

(2) 1 mL of 30 mM citric acid (MW=192.12, Sigma-Aldrich, 99.5%) was rapidly injected into the mixed solution. The overdosed citric acid anions acted as protected agents on the surface of the as-prepared gold nanocrystals. Usually, the ratio of the [$HAuCl_4$]/[Citric Acid] was 1:3.

(3) The mixed solution color changed from orange-yellow to purple red and finally wine red within 10 min at 60-75° C. with vigorous stirring.

(4) The final total volume was ~120 mL. The reaction was kept 15-20 min at 65° C. with vigorous stirring. The reacted solution was about pH=3.5. ~100 mL of the reacted solution stored at 4° C. and the other 20 mL solution was coated using 1 μL of 98% GIE 15-30 min before being stored at 4° C.

3). Preparing $CoFe_2O_4$@Au@$TiO_2$ Core-Corona-Shell Nanocrystals (18.5 nm)

(1) 100 uL of ~0.1 M $TiCl_4$ in 20% HCl firstly diluted to 1.5 mL in 37% HCl+0.9 mL water solution.

(2) 75 mL as-prepared $CoFe_2O_4$@Au nanocrystal solution without GIE coated with vigorous stirring in 22.5 mL of pure water. Then slowly adding mixed $TiCl_4$ solution into the mixed $CoFe_2O_4$@Au nanocrystal solution with vigorous stirring. The total volume of the sample solution was 100 mL. The reaction solution was kept at room temperature.

(3) The sample solution from dim red wine waned after the first drop being added and became slight purple within 1 min and to transparent when the sample solutions were mixed within 15 min. The reaction was kept 3 hours and the final pH value was at pH=0.5-1.0. Half of the reacted solution was stored at 4° C. and the other solution was coated using 1 μL of 98% GIE 30-60 min before being stored at 4° C.

l) Preparation of 10 nm of $CoFe_2O_4$@Au@$TiO_2$ Core-Corona-Shell Nanocrystal Materials in Aqueous Solution 1). Preparing $CoFe_2O_4$ Magnetic Nanocrystals (2 nm)

(1) 60 mL of 100 mM $Co(NO_3)_2.6H_2O$ (3*0.582 g, MW=291.03, Sigma-Fluka, >98%) aqueous solution and 60 mL of 200 mM $Fe(NO_3)_{3-9}H_2O$ (3*1.616 g, MW=404.00, Sigma-Aldrich, >99.8%) aqueous solution were mixed with 120 mL of pure water firstly.

(2) 60 mL of 300 mM citric acid (3.456 g, MW=192.12, Sigma-Aldrich, 99.5%) aqueous solution was quickly added into the as-mixed solution with stirring at room temperature. After reacting 1 hour, a burnt orange solution was obtained. All mixture solutions appeared clear and did not exhibit any phase separation at pH=~1.0-1.5.

(3) [Co(II)+Fe(III)]/[Citric Acid]=1:1; [Co(II]/[Fe(III)]=1:2; [$NO_3^-$]/[Citric Acid]=3:8.

(4) The final total volume was 300 mL. One-third of half prepared solution coated was carried out by adding 1.314 mmol of 98% of GIE (169.4 uL) for reacting 30-60 min.

(5) Both of the uncoated and coated sample solutions allowed to gel in static air at 50° C. in a water-bath for 24 hours.

2). Preparing $CoFe_2O_4$@Au Core-Shell Nanocrystals (9 nm)

(1) 1 mL of 10 mM $HAuCl_4.3H_2O$ (Sigma, MW=393.83) aqueous solution was added to 1 mL as-prepared 2 nm of $CoFe_2O_4$ nanocrystal+96 mL double distilled water (18.2 MΩ) with vigorous stirring to mix.

(2) 1 mL of 30 mM citric acid (MW=192.12, Sigma-Aldrich, 99.5%) was rapidly injected into the mixed solution. The citric acid anions acted as protected agents on the surface of the as-prepared gold nanocrystals.

(3) mL of ~0.1 M freshly prepared aqueous sodium borohydride ($NaBH_4$) solution was added to the solution all at once with vigorous stirring.

(4) The final total volume was ~100 mL. 50 mL of the reacted solution was stored at 4° C. and the other 50 mL solution was coated using 1 μL of 98% GIE 15-30 min before being stored at 4° C.

3). Preparing $CoFe_2O_4$@Au@$TiO_2$ Core-Corona-Shell Nanocrystals (10 nm)

(1) 100 uL of ~0.1 M $TiCl_4$ in 20% HCl firstly diluted to 1.5 mL in 37% HCl+0.9 mL water solution.

(2) 25 mL as-prepared $CoFe_2O_4$@Au nanocrystal without GIE coated with vigorous stirring in pure water. Then mixed $TiCl_4$ solution was slowly added into the mixed $CoFe_2O_4$@Au nanocrystal solution with vigorous stirring. The total volume of the sample solution was 100 mL. The reaction solution was kept at room temperature.

(3) The sample solution from dim red wine waned after the first drop being added and became slight purple within 1 min and to transparent when the sample solutions were mixed within 15 min. The reaction was kept 3 hours and the final pH value was at pH=0.5-1.0. Half of the reacted solution was stored at 4° C. and the other solution was coated using 1 μL of 98% GIE 30-60 min before being stored at 4° C.

Figure 6:
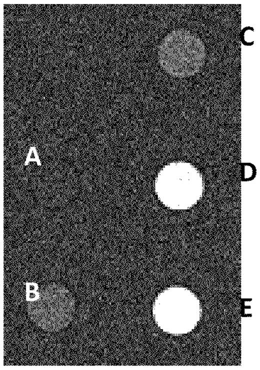
FIG. 6. MRI images of $T_1$-weighted 20 nm of core-corona-shell particulate $CoFe_2O_4$@Au@$TiO_2$ without GIE coating (Spot D) and with GIE coating (Spot E). The Spot A is water as a reference. 6 nm of particulate $TiO_2$ without GIE coating (Spot B) and with GIE coating (Spot C) are also as references.
Figure 7:
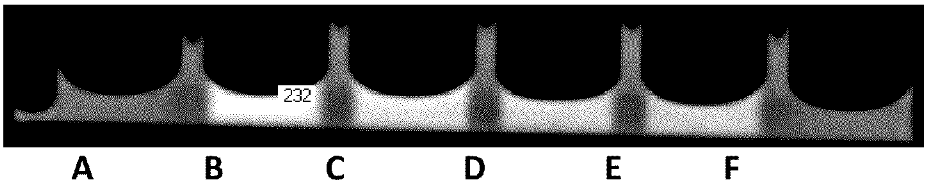
FIG. 7. CT images of 20 nm of core-corona-shell particulate $CoFe_2O_4$@Au@$TiO_2$ nanomaterials with GIE coating (B column) and without GIE coating (C column) and 6 nm of anatase type of particulate $TiO_2$ nanomaterials coated by GIE (D column) and without GIE coating (E column). The A and F columns are water as a reference.

$CoFe_2O_4$@Au@$TiO_2$ nanoparticles were synthesized and tested in vitro as the nanomaterial for contrast agents of both MRI and CT. Uptake of nanoparticles was tested in cells in culture. MRI images and CT images of core-corona-shell particulate $CoFe_2O_4$@Au@$TiO_2$ without GIE coating are shown in FIG. 6 and FIG. 7.

m) Preparation of 8 nm of $CoFe_2O_4$@Ag@$TiO_2$ Core-Corona-Shell Nanocrystal Materials in Aqueous Solution 1). Preparing $CoFe_2O_4$ Magnetic Nanocrystals (2 nm)

(1) 60 mL of 100 mM $Co(NO_3)_2.6H_2O$ (3*0.582 g, MW=291.03, Sigma-Fluka, >98%) aqueous solution and 60 mL of 200 mM $Fe(NO_3)_{3-9}H_2O$ (3*1.616 g, MW=404.00, Sigma-Aldrich, >99.8%) aqueous solution were mixed with 120 mL of pure water firstly.

(2) 60 mL of 300 mM citric acid (3.456 g, MW=192.12, Sigma-Aldrich, 99.5%) aqueous solution was quickly added into the as-mixed solution with stirring at room temperature. After reacting 1 hour, a burnt orange solution was obtained. All mixture solutions appeared clear and did not exhibit any phase separation at pH=~1.0-1.5.

(3) [Co(II)+Fe(III)]/[Citric Acid]=1:1; [Co(II)]/[Fe(III)]=1:2; [$NO_3^-$]/[Citric Acid]=3:8.

(4) The final total volume was 300 mL. One-third of half prepared solution coated was carried out by adding 1.314 mmol of 98% of GIE (169.4 uL) for reacting 30-60 min.

(5) Both of the uncoated and coated sample solutions allowed to gel in static air at 50° C. in a water-bath for 24 hours.

2). Preparing $CoFe_2O_4$ g Core-Shell Nanocrystals (6 nm)

(1) 1 mL of 10 mM $AgNO_3$ aqueous solution was added to 1 mL as-prepared $CoFe_2O_4$ nanocrystal+96 mL of double distilled water (18.2 MΩ) with vigorous stirring to mix.

(2) 1 mL of 30 mM citric acid (MW=192.12, Sigma-Aldrich, 99.5%) was rapidly injected into the mixed solution. 1 mL of ~0.1 M freshly prepared aqueous sodium borohydride ($NaBH_4$) solution was added to the solution all at once with vigorous stirring.

(3) The mixed solution color changed from orange-yellow to orange within 1 min after the addition of $NaBH_4$ aqueous solution.

(4) The final total volume was 100 mL. 50 mL of the reacted solution was stored at 4° C. and the other 20 mL solution was coated using 1 μL of 98% GIE 15-30 min before being stored at 4° C.

3). Preparing $CoFe_2O_4$@Ag@$TiO_2$ Core-Corona-Shell Nanocrystals (8 nm)

(1) 100 uL of ~0.1 M $TiCl_4$ in 20% HCl firstly diluted to 1.5 mL in 37% HCl+0.9 mL water solution.

(2) 25 mL as-prepared $CoFe_2O_4$@Ag nanocrystal without GIE coated with vigorous stirring in pure water. Then the mixed $TiCl_4$ solution slowly was added into the mixed $CoFe_2O_4$@Ag nanocrystal solution with vigorous stirring. The total volume of the sample solution was 100 mL. The reaction solution was kept at room temperature.

(3) The sample solution become transparent when the sample solutions were mixed within 10 min. The reaction was kept 30 min. Half of the reacted solution was stored at 4° C. and the other solution was coated using 1 μL of 98% GIE 30-60 min before being stored at 4° C.

n) Preparation of 12 nm of $CoFe_2O_4$@Ag@$TiO_2$ core-corona-shell nanocrystals in aqueous solution 1). Preparing $CoFe_2O_4$ Magnetic Nanocrystals (2 nm)

(1) 60 mL of 100 mM $Co(NO_3)_2.6H_2O$ (3*0.582 g, MW=291.03, Sigma-Fluka, >98%) aqueous solution and 60 mL of 200 mM $Fe(NO_3)_{3-9}H_2O$ (3*1.616 g, MW=404.00, Sigma-Aldrich, >99.8%) aqueous solution were mixed with 120 mL of pure water firstly.

(2) 60 mL of 300 mM citric acid (3.456 g, MW=192.12, Sigma-Aldrich, 99.5%) aqueous solution was quickly added into the as-mixed solution with stirring at room temperature. After reacting 1 hour, a burnt orange solution was obtained. All mixture solutions appeared clear and did not exhibit any phase separation at pH=~1.0-1.5.

(3) [Co(II)+Fe(III)]/[Citric Acid]=1:1; [Co(II])/[Fe(III)]=1:2; [$NO_3^-$]/[Citric Acid]=3:8.

(4) The final total volume was 300 mL. One-third of prepared solution coated was carried out by adding 1.314 mmol of 98% of GIE (169.4 uL) for reacting 30-60 min.

(5) Both of the uncoated and coated sample solutions allowed to gel in static air at 50° C. in a water-bath for 24 hours.

2). Preparing $CoFe_2O_4$@Ag Core-Shell Nanocrystals (10 nm)

(1) 5 mL of 10 mM $AgNO_3$ aqueous solution was added to 1 mL as-prepared $CoFe_2O_4$ nanocrystal+90 mL of double distilled water (18.2 MΩ) with vigorous stirring to mix.

(2) 3 mL of 30 mM citric acid (MW=192.12, Sigma-Aldrich, 99.5%) was rapidly injected into the mixed solution. 2 mL of ~0.1 M freshly prepared aqueous sodium borohydride ($NaBH_4$) solution was added to the solution all at once with vigorous stirring.

(3) The mixed solution color changed from orange-yellow to orange within 1 min after the addition of $NaBH_4$ aqueous solution.

(4) The final total volume was 100 mL. 50 mL of the reacted solution was stored at 4° C. and the other 20 mL solution was coated using 1 μL of 98% GIE 15-30 min before being stored at 4° C.

3). Preparing $CoFe_2O_4$@Ag@$TiO_2$ Core-Corona-Shell Nanocrystals (12 nm)

(1) 200 uL of ~0.1 M $TiCl_4$ in 20% HCl firstly diluted to 1.5 mL in 37% HCl+0.8 mL water solution.

(2) 25 mL of as-prepared $CoFe_2O_4$@Ag nanocrystal without GIE coated with vigorous stirring in pure water. Then the mixed $TiCl_4$ solution was slowly added into the mixed $CoFe_2O_4$@Ag nanocrystal solution with vigorous stirring. The total volume of the sample solution was 100 mL. The reaction solution was kept at room temperature.

(3) The sample solution was transparent when the sample solutions were mixed within 1-3 min. The reaction was kept 30 min. Half of the reacted solution was stored at 4° C. and the other solution was coated using 1 μL of 98% GIE 30-60 min before being stored at 4° C.

Example 2

Figure 8:
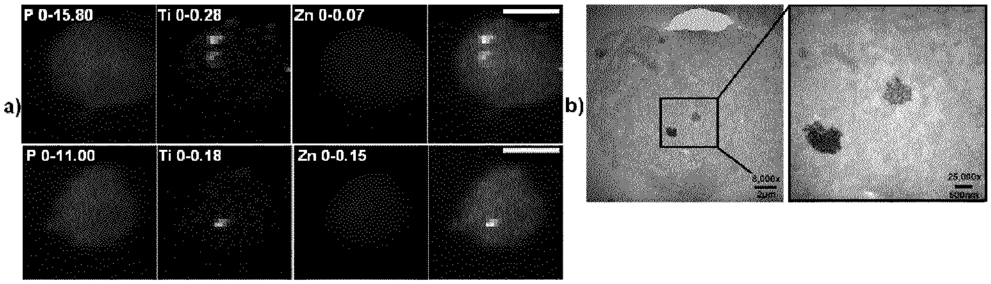
FIG. 8. XFM maps and TM images of MCF7/WS8 cells transfected with nucleolus-specific nanoconjugates. (a) MCF7/WS8 cells were electroporated and imaged by X-ray fluorescence microscopy. Elemental maps and map overlaps are shown for P, Ti, and Zn. Scanning was done at 2ID-E beamline at the APS. White size bars are 10 μm. Numbers following elemental sign show elemental concentration in μg per $cm^2$. (b) TEM image of 100 nm thin section of a MCF7/WS8 cells electroporated with nucleolus specific nanoconjugate; left panel, cell cross section; right panel, TEM detail with two nanoconjugate rich spots. Imaging was done at Northwestern University Cell Imaging Core Facility.

Nanoparticle Surface Conjugation/Coating Using Different (Bio) Molecules and Different Conjugation Chemistries a) Nucleic Acid Targeting of Intracellular Compartments 1) DNA oligonucleotide nanoconjugates (TiNCs) bind to appropriate target sequences in live mammalian cells; TiNCs specific for the nucleolus are retained in the nucleolus; those specific for mitochondria are retained in mitochondria, as shown in FIG. 8.

Figure 9:
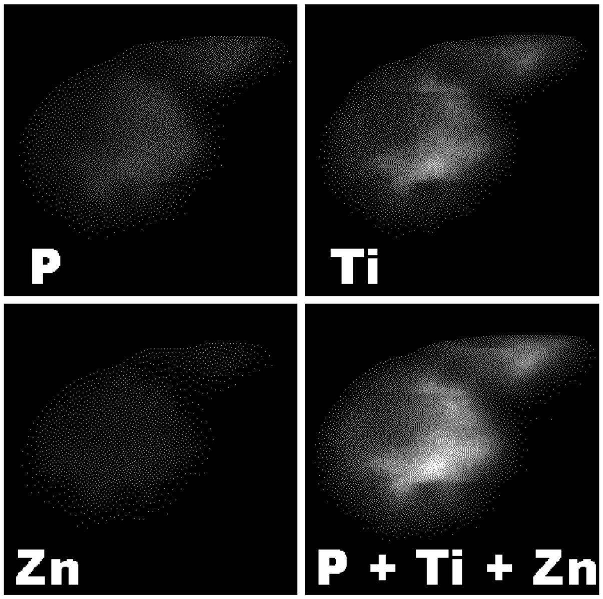
FIG. 9. K alpha X-ray fluorescence microscopy of PC12 cells.

2) $TiO_2$-DNA oligonucleotide nanoconjugates (TiNCs) bind to rDNA target sequences in live mammalian cell nucleoli, as shown in isolated nuclei in FIG. 9.

Figure 10:
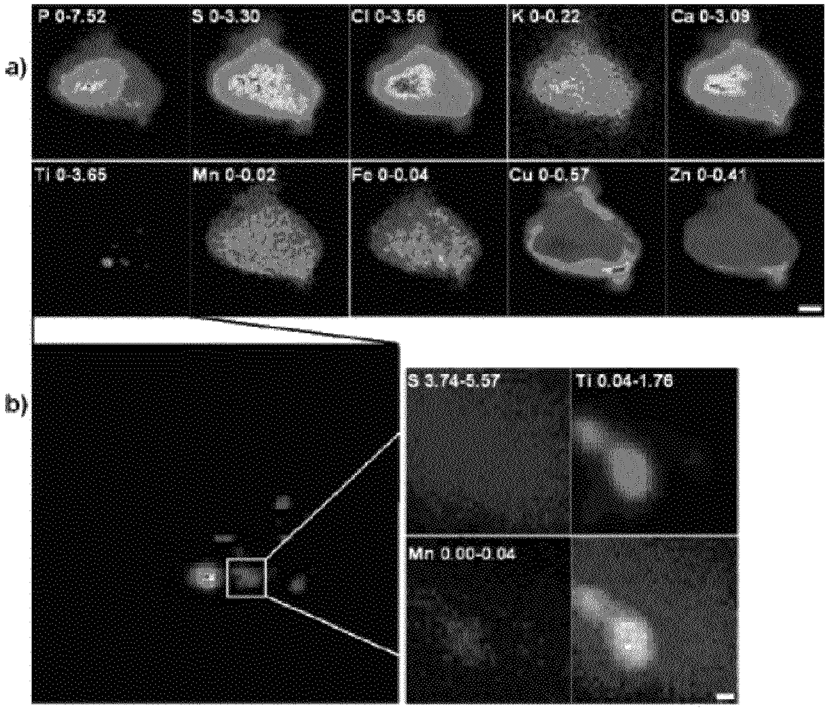
FIG. 10. XFM maps of whole PC12 cell transfected with mitochondria-specific nanoconjugates using natural uptake. (a) Elemental maps of P, S, Cl, K, Ca, Ti, Mn, Fe, Cu, and Zn in PC12 cell treated with nanoconjugates carrying ND2s oligonucleotide for 24 h and then "washed" for 24 h in nanoconjugatefree medium. (b) Enlarged Ti maps of the cells in (a) and a detailed XFM map of a mitochondria inside the cell. Left: enlarged Ti map of the whole cell from the right panel of FIG. 3*a*. Right: S, Ti, Mn and overlap maps for the mitochondria-shaped form from the left panel.
Figure 11:
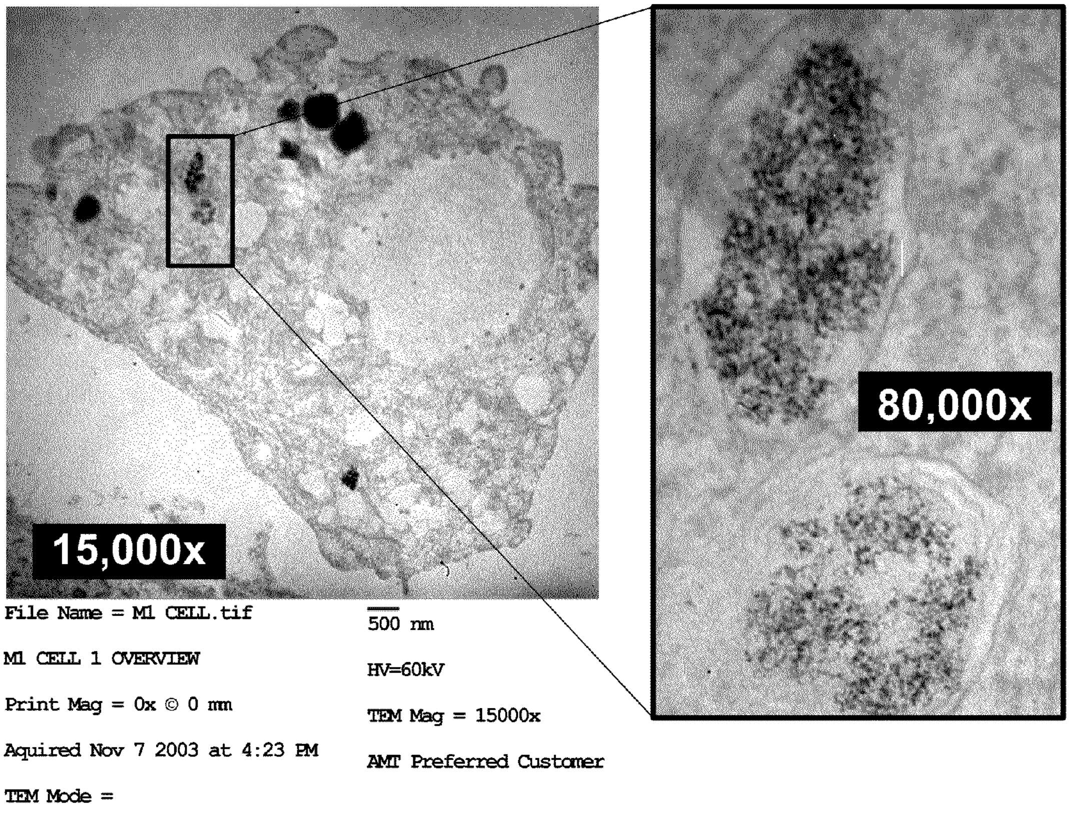
FIG. 11. TEM image of a 100 nm thin section of a PC12 cell electroporated with mitochondria-specific $TiO_2$-DNA. Left: cell with several mitochondria containing nanoconjugate. Right: detailed image of two adjacent mitochondria. The very dense nongranular material located in the cell vacuoles is osmium tetraoxide.

3) $TiO_2$-DNA oligonucleotide nanoconjugates (TiNCs) bind to appropriate target sequences in live mammalian cells; TiNCs specific for the nucleolus are retained in the nucleolus; those specific for mitochondria are retained in mitochondria, as shown in FIG. 10 and FIG. 11.

Figure 12:
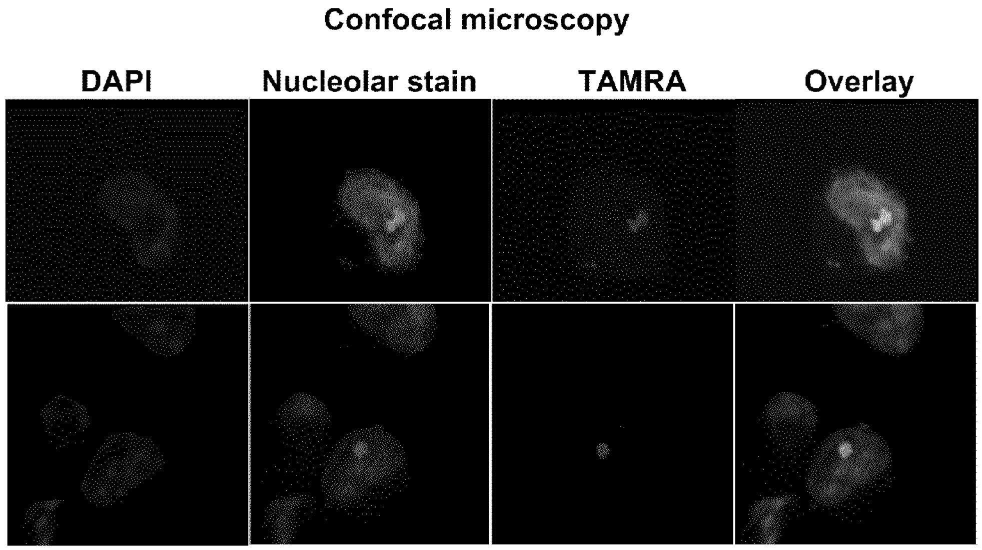
FIG. 12. Nanoconjugates with fluorescently labeled oligonucleotides bind to appropriate target sequences in live mammalian cells; in this case the nucleolus, on the background of stained nucleus.

4) Nanoconjugates with fluorescently labeled oligonucleotides, as shown in FIG. 12.

Figure 13:
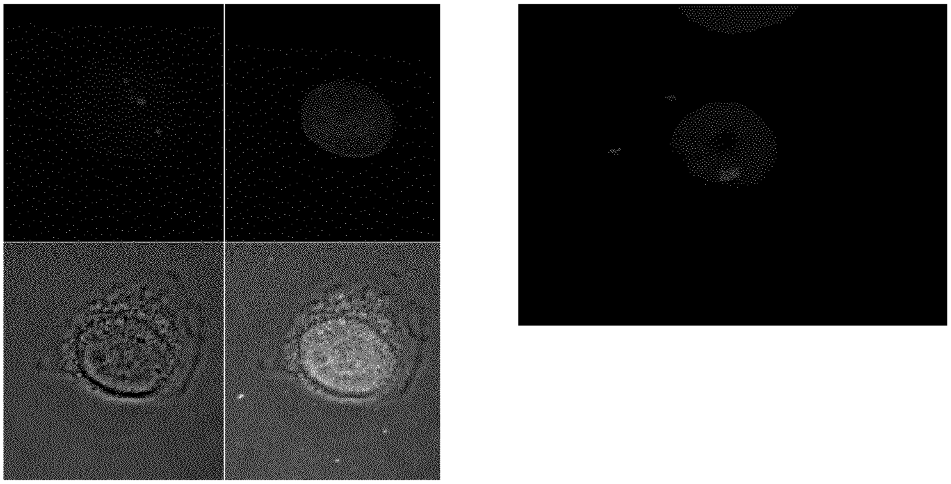
FIG. 13. DNA (left) and PNA (right) conjugated nanoparticles were also coated with fluorescent molecules. Nanoconjugates were bound to appropriate target sequences in live mammalian cells, in this case the nucleolus, and then fixed and nuclear DNA stained to show overlap.

5) Nanoconjugates with fluorescent dye, creating fluorescent nanoparticles, as shown in FIG. 13.

b) Peptide Targeting and Fluorescence Imaging in Cells

Figure 14:
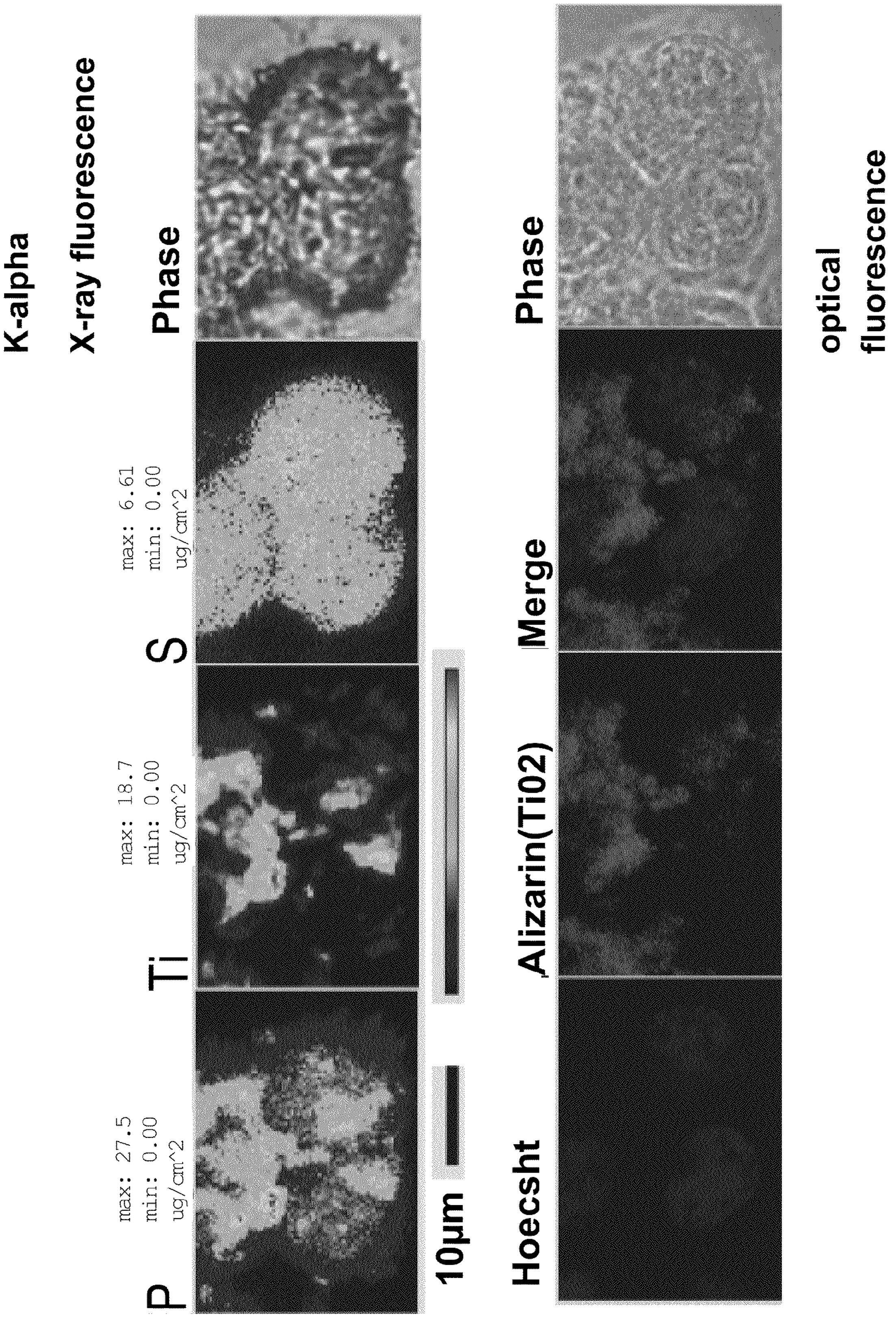
FIG. 14. X-ray fluorescence and optical fluorescence in individual cells treated with fluorescently labeled nanoconjugates coated with peptide directed against Epidermal Growth Factor Receptor (EGFR).

1) Peptide coated nanoconjugates facility cell uptake, as shown in FIG. 14.

Figure 15:
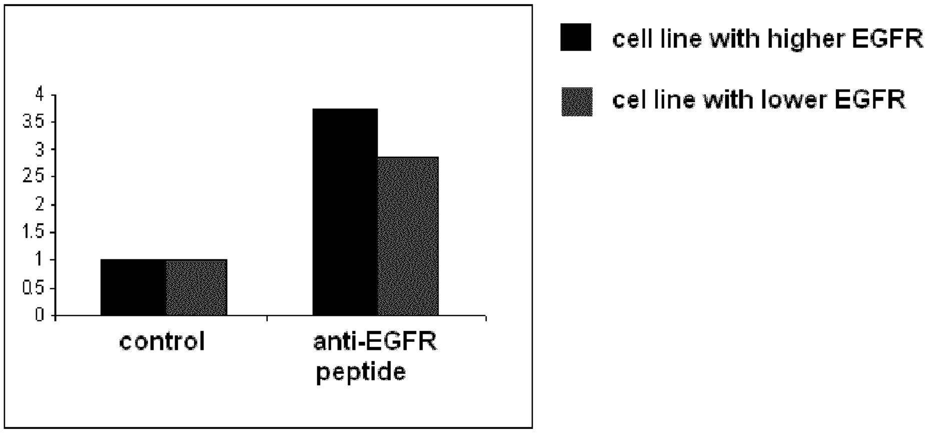
FIG. 15. Median fluorescence of cells treated with fluorescently labeled nanoconjugates coated with peptide directed against Epidermal Growth Factor Receptor (EGFR), determined by flow cytometry.
Figure 16:
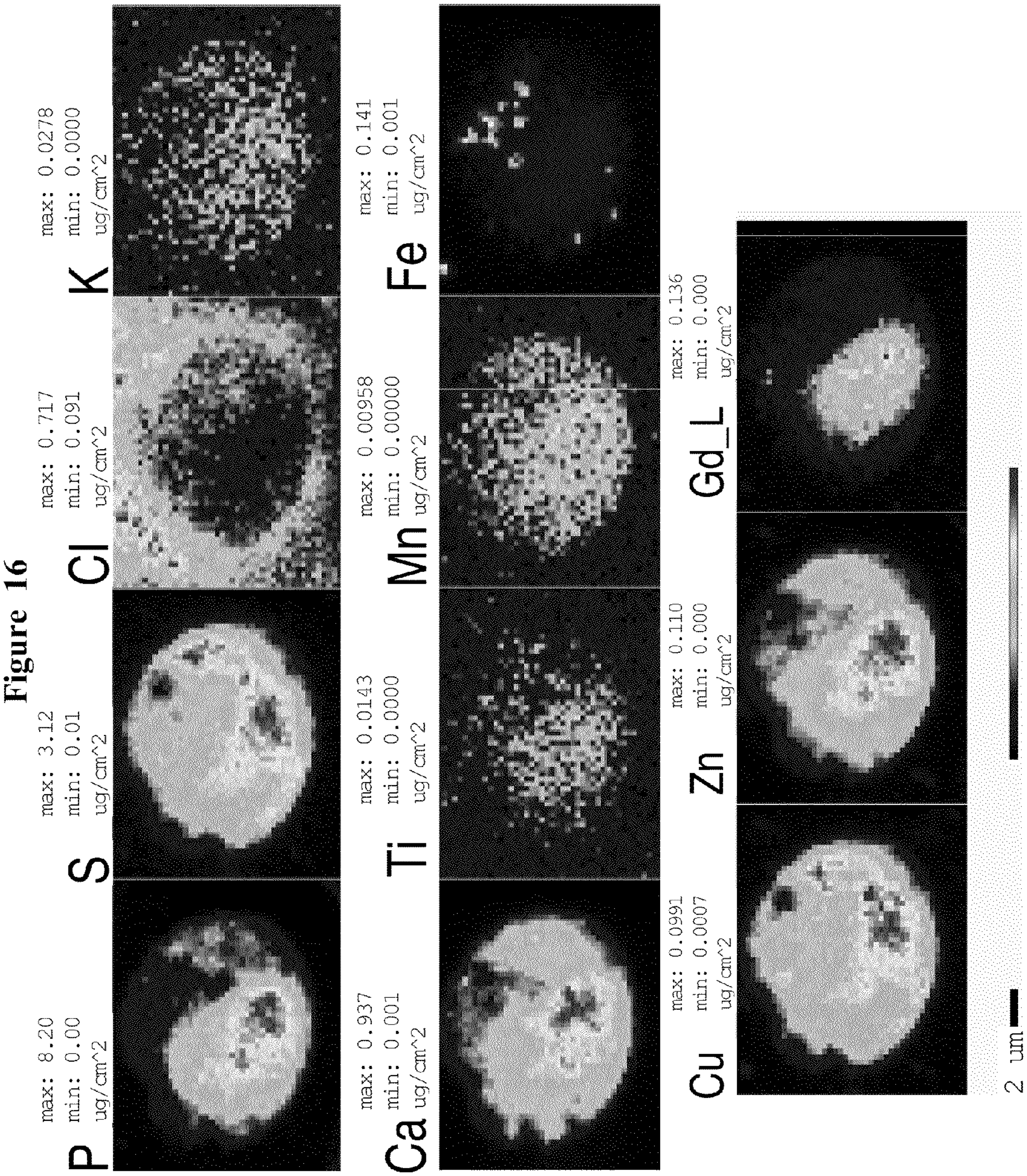
FIG. 16. Testing a Gd contrast agent attached to $TiO_2$ NP covalently; nanoparticles were functionalized with nucleus targeting oligonucleotide at ratio of 1 NP:30-600 Gd:10 oligos.

2) Peptide coated nanoconjugates targeting Epidermal Growth Factor Receptor (EGFR), as shown in FIG. 15.

c) Nucleic Acid Targeting, Gd Contrast Agent Functionalization and MR Imaging of Cells, as Shown in FIG. 16.

Example 3

PNA-$TiO_2$ Nanoconjugates

A. Materials and Methods

PNAs, DNA Oligonucleotides, Nanoconjugates, and Plasmids

All nucleic acid sequences used within this study are depicted in FIG. 17*a*. PNA containing a sequence of a segment of ribosomal 18S rDNA gene was synthesized with a dopamine conjugated via succinic acid to the N terminal end (Biosynthesis). PNA-$TiO_2$ nanoconjugates were synthesized by covalently linking 3 nm $TiO_2$ nanoparticles to the PNA in a 1:1 molar ratio as described previously for DNA oligonucleotides (Paunesku et al., Nat. Mater. 2003, 2, 343-346). Under these conditions some nanoparticles without PNA and some with more than one PNA molecule per nanoparticle can be expected to occur, in addition to one nanoparticle:one PNA nanoconjugate species. The DNA oligonucleotides used to prepare target oligonucleotide dsDNA "dsr18" and PNA complementary molecular beacon "r18ASMB1" (with 6-Carboxy-2',4,4',5',7,7'-hexachlorofluorescein as a fluorophore and Dabcyl as a quencher) were obtained from Sigma Genosys. A non-complementary dsDNA oligonucleotide "dsFM20" was prepared from "bFM20" and "aFM20AS" oligonucleotides and a non-complementary molecular beacon "MS5MB1" were obtained from the same source. All DNA oligonucleotides were kept as 100 mM stock solutions in TE buffer (10 mM TrisCl 1 mM EDTA pH=8) at −80° C.

A short peptide segment of epidermal growth factor receptor (pEGFR) (N term-SEQ ID NO:9 RRRHIVRKRTLRR-C term) (Sigma-Genosys) containing a nuclear localization signal (NLS) or Alizarin red s (Fluka) was conjugated to PNA-$TiO_2$ nanoconjugates to cover approximately 5% (9 molecules) and 10% (17 molecules) of the nanoparticle surface respectively. Three nanometer $TiO_2$ nanoparticles have approximately 173 Ti atoms on the surface, each providing a potential binding site for one peptide or Alizarin red s. Conjugation of these nanoparticle modifiers was confirmed by a shift in peak absorbance wavelength of the nanoconjugates compared to nanoparticles alone. In addition, Alizarin red s is a fluorescent molecule (excitation 530-560 nm, emission 580 nm) and can be monitored using a fluoroimager (Typhoon Trio Variable Mode Imager).

Nanoparticles of colloidal $TiO_2$ were prepared as has been described in detail elsewhere (Paunesku et al., supra). The size of nanoparticles used in these experiments was 3 nm, which renders them avid in binding with dopamine-modified PNAs. At neutral pH (6-8) $TiO_2$ nanoparticles can be precipitated by centrifugal forces greater than 0.2 g.

The plasmid pKaede-MN1 (Marine Biological Laboratory) was used to investigate the ability of nanoconjugates to invade plasmid DNA. The oligonucleotides r18Sclone and r18ASclone (FIG. 17*a*) formed a dsDNA insert that was cloned into EcoR1/Xho1 sites of this plasmid, producing the recombinant pKaede-MN1-R18.

Gel Electrophoresis

Hybridization reactions containing Alizarin red s, ssDNA (67.0 μM), and either PNAs or PNA-TiO2 nanoconjugates (33.5 μM) were heated to 95° C. for 2 min and cooled to room temperature over 3 hours. Reactions were separated on 8-16% polyacrylamide gels (acrylamide/bisacrylamide 19:1, EMD Chemicals Inc.) in 1×TBE buffer (Sigma) for 2-3 hours. Nanoparticles were visualized in wells of the gel, still contained within glass plates, by monitoring Alizarin red s fluorescence by a fluoroimager Typhoon Trio Variable Mode Imager. DNA bands were visualized on the same gel after its removal from the glass plates and staining with GelStar (Cambrex). PNAs do not absorb this dye, as well as several other DNA intercalating dyes (Wittung et al., Nucleic Acids Res. 1994, 22, 5371-5377), therefore they were visualized only in the context of hybrids with DNA.

Nucleic Acid Hybridization Monitoring Using a Real Time PCR Apparatus

Hybridization reactions were monitored using a 7300 Real Time PCR System (Applied Biosystems) and the following hybridization-dissociation protocol: 95° C. for 15 seconds, cooling to 4° C., incubation at 4° C. for 30 seconds, and gradual reheating to 95° C. over approximately 1¼ hours. HEX signal (for molecular beacons) or Power Sybr Green (Applied Biosystems) signal (for dsDNA) was recorded incrementally (approximately every 20 seconds) during the reheating phase. Hybridization and invasion reactions were also performed at 37-38° C. for 20 minutes, with HEX or Power Sybr Green signal being recorded incrementally throughout (approximately every 60 seconds). The average fluorescence measurement during this time was reported. All hybridization reactions involving molecular beacons (0.33 μM) contained nanoconjugates or free PNAs (0.66 μM) in the presence of 10 mM sodium phosphate buffer (NaH2PO4). Unless otherwise noted, experiments utilizing Power Sybr Green (Applied Biosystems) contained nanoconjugates or PNAs (1.0 μM) and complementary dsDNA oligonucleotides (0.5 μM). Fluorescence intensity values were calculated by automated Applied Biosystems software, as well as dissociation curves and derivative dissociation curves.

Plasmid Invasion

Nanoparticles and nanoconjugates used in plasmid invasion studies were partially coated with Alizarin red s (surface coverage was 10% or 17 molecules of Alizarin red s per nanoparticle). Plasmid precipitation was done by taking advantage of the fact that in neutral pH buffers 3 nm $TiO_2$ nanoparticles can be precipitated by centrifugation at 0.2 g. Nanoparticles or nanoconjugates (115 nM) were mixed with supercoiled plasmid DNA (57.5 nM) in sodium phosphate buffer with 137 mM sodium and incubated 2 hours at 37° C. to allow for dsDNA invasion. Centrifugation for 10 min at 0.2 g followed; the pellet was washed by the same buffer and re-precipitated. Following a second wash, samples were loaded onto a gel and subjected to electrophoresis. Due to large size of the plasmid DNA, force of electrophoresis separated plasmid molecules from nanoconjugates, allowing the plasmids to enter into the gel.

Statistical Analyses

Statistical significance of differences were determined through ANOVA analyses followed by Tukey Honest Significant Difference multiple comparisons tests using Systat 10.2 statistical analyses software (Systat Software Inc.). The bar graphs show means of three independent experiments with standard error (SE) and statistical significance; the latter indicated by * as described in each figure legend.

B. Results

Figure 17:
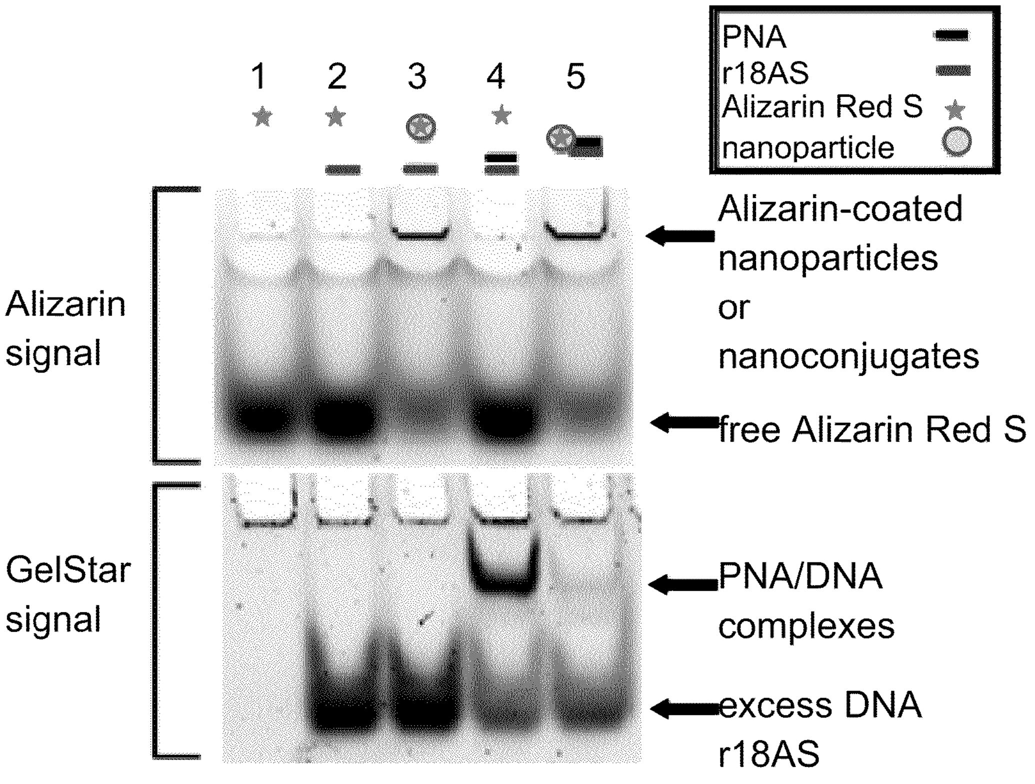
FIG. 17. PNA-$TiO_2$ nanoconjugates can be successfully conjugated and withstand incubation at 95° C. Lanes 1-4 contain control reactions; lane 1 is free Alizarin Red S, lane 2 is a mixture of Alizarin Red S and complementary oligonucleotide DNA, lane 3 is Alizarin Red S-conjugated nanoparticle (without PNA) and complementary oligonucleotide DNA, and lane 4 contains a mixture of PNA (PNA-r18S), complementary oligonucleotide (r18AS), and Alizarin Red S. The test sample (lane 5) contains a mix of Alizarin Red S coated $TiO_2$-PNA and twofold molar excess of complementary r18AS oligonucleotide DNA.

Conjugation of PNA-$TiO_2$ Nanoconjugates and Hybridization to Complementary DNA To demonstrate the conjugation efficiency of the PNA-$TiO_2$ nanoconjugates, the fact that $TiO_2$ nanoparticles do not enter into polyacrylamide gels during typical electrophoresis was utilized (Paunesku et al., supra). To image the nanoparticles, they were conjugated to the fluorescent agent Alizarin red s (Rajh et al., J Phys Chem B. 2002, 106, 10543-10552), whereas nucleic acids (ssDNA and ssDNA/PNA hybrids) were stained by GelStar dye after the electrophoresis. All nucleic acids used throughout this study are listed in Table 1. Hybridization reactions and controls were run on a polyacrylamide gel and imaged first for Alizarin red s, then stained with GelStar to visualize DNA (FIG. 17). In lane 4: with 1:2 molar ratio of PNA and complementary oligonucleotide, a PNA/DNA band can be visualized, while no such band is notable in lane 5: with 1:2 ratio of PNA-$TiO_2$ and complementary oligonucleotide. The vast majority of PNA in that lane is conjugated to the nanoparticle and therefore is not free to enter the gel. Hence, conjugated $TiO_2$-PNAs withstand incubation at 95° C.

Figure 18:
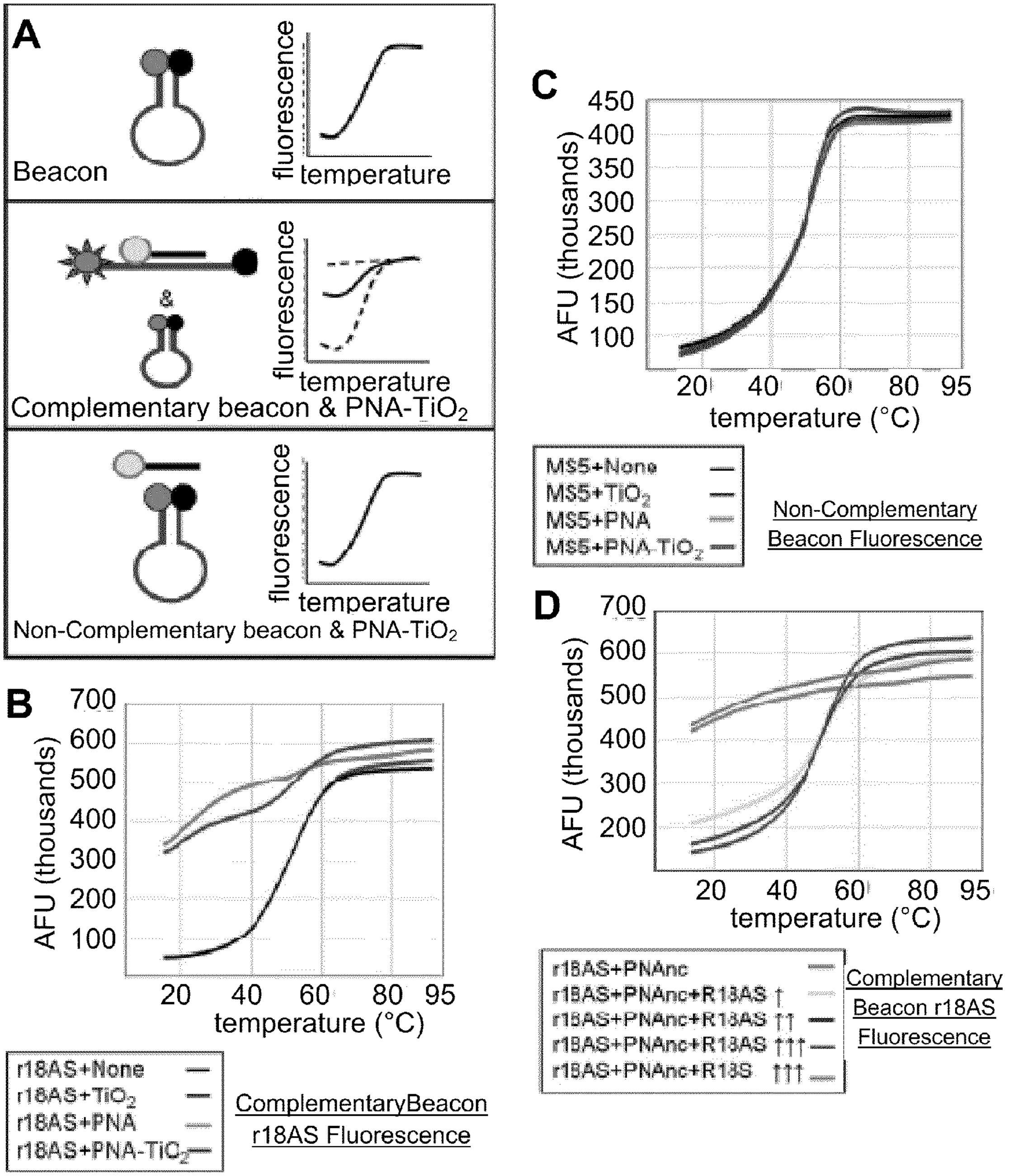
FIG. 18. $TiO_2$-PNA nanoconjugates can hybridize to complementary DNA. (A) Schematic representation depicts changes in fluorescence resulting from self-hybridization and melting of molecular beacons, changes in fluorescence caused by hybridization between molecular beacons and PNA-$TiO_2$ and self-hybridization and melting of molecular beacon, and changes in fluorescence when noncomplementary PNA-$TiO_2$ and molecular beacon are mixed. (B and C) Representative dissociation curves resulting from hybridization reactions containing test samples and complementary molecular beacon (B) or noncomplementary molecular beacon (C) are shown. (D) The addition of various amounts of excess unlabeled PNA-complementary DNA oligonucleotide (r18AS), as molecular beacon competitor, to samples containing PNA-$TiO_2$ or PNA and complementary molecular beacons gradually returns the shape of the fluorescence curve to that obtained with samples containing molecular beacons alone.

To investigate the ability of PNA-$TiO_2$ nanoconjugates to hybridize to complementary target DNA, we used molecular beacons containing either a complementary or non-complementary DNA sequence in its loop (FIG. 18*a*). Changes in molecular beacon fluorescence, due to hybridization to the nanoconjugate, were monitored using a standard dsDNA dissociation protocol (Applied Biosystems); anticipated results are shown schematically in FIG. 18*a*. When the molecular beacon exists alone (FIG. 18*a*, top panel) or does not contain a complementary target to the nanoconjugate (FIG. 18*a*, bottom panel), the molecular beacon exists primarily in the closed position at temperatures below the melting temperature of the stem and low fluorescence values are expected. In either of these cases, a sigmoid increase in fluorescence will occur when temperatures are raised above the melting temperature of the molecular beacon stem and the beacon transforms to the open position. Conversely, when the molecular beacon contains a complementary target, hybridization of the nanoconjugate will increase the presence the open species of molecular beacon and raise fluorescence values at lower temperatures (FIG. 18*a*, middle panel). The addition of free $TiO_2$ nanoparticles (FIG. 18*b*) had little effect on the shape of the curve produced by molecular beacon alone (FIG. 18*b*). The addition of PNA-$TiO_2$ nanoconjugates complementary to the molecular beacon resulted in a more than six-fold increase at initial fluorescence measurement at 14° C. (FIG. 18*b*, purple curve); as expected, this ratio is eventually lost at temperatures melting the molecular beacon stem. None of these alterations in fluorescence curves were observed when the same dissociation analyses were performed using a molecular beacon with a non-complementary target DNA sequence in the molecular beacon loop (FIG. 18*c*). The presence of increasing concentrations of competitor-non-labeled oligonucleotide complementary to PNA (with a sequence identical to the loop of the molecular beacon) sequesters PNA-$TiO_2$ nanoconjugates and reduces the observed changes in fluorescence due to hybridization between the molecular beacon and PNA-$TiO_2$ nanoconjugate (FIG. 18*d*).

Figure 19:
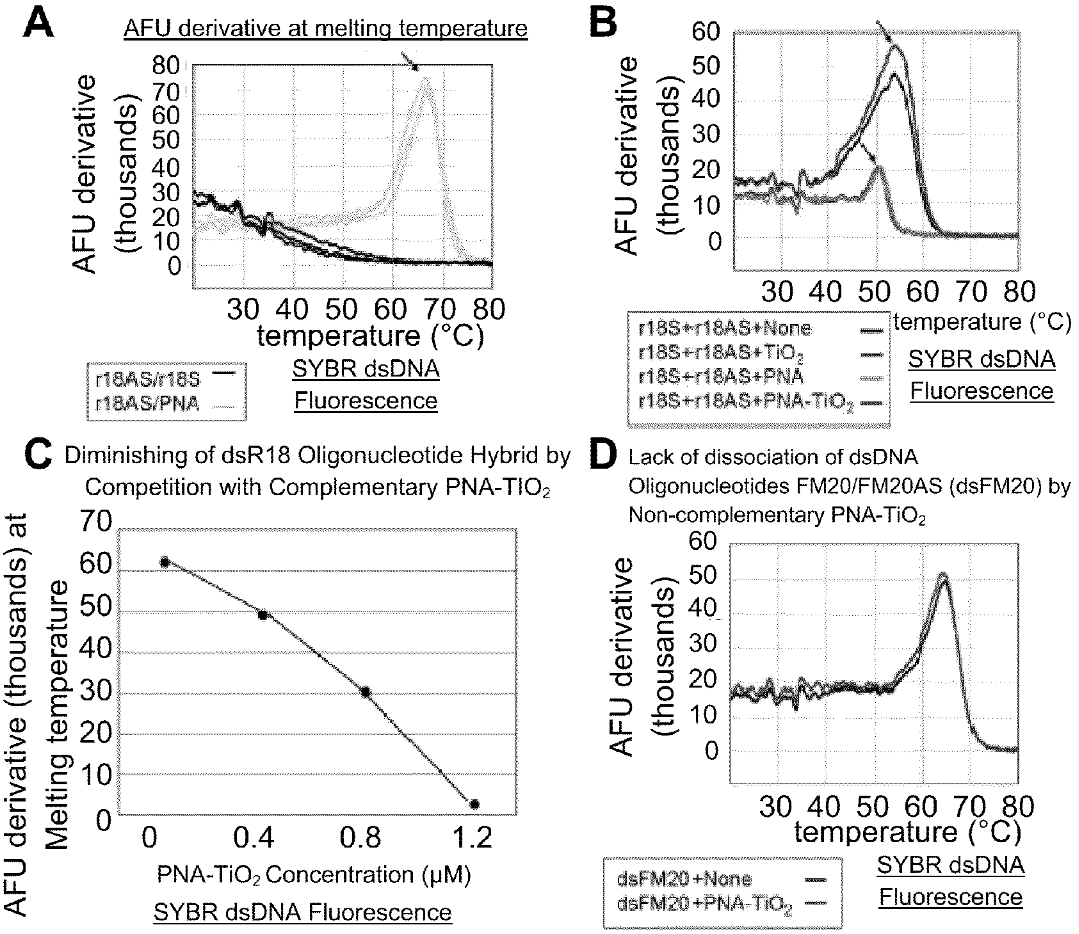
FIG. 19. PNA-$TiO_2$ nanoconjugates outcompete (replace) homologous DNA oligonucleotides in formation of the double-stranded hybrid (labeled R18 when made of two DNA oligonucleotides). (A) Derivative dissociation curves of fluorescence intensities show a well-defined melting temperature (Tm) peak (indicated by an arrow) for dsDNA hybrids but not PNA/DNA complexes (three replicates each). (B) Derivative dissociation curves show a lowering of the Tm peak height associated with competition between the homologous DNA strand of dsR18 and PNA or PNA-$TiO_2$ for the same target (complementary DNA oligonucleotide). Black arrows point to the AFU derivative at the Tm. (C) A graph showing inverse dependence of the peak height for the value of AFU derivative at the Tm peak related to the concentration of $TiO_2$-PNA nanoconjugates added to oligonucleotides creating dsR18 molecules is shown. (D) Representative derivative dissociation curves show no change in the Tm peak intensity when PNA-$TiO_2$ is combined with the noncomplementary dsDNA (hybrid of FM20 and FM20AS oligonucleotides, labeled dsFM20).

The hybridization abilities of PNA-$TiO_2$ nanoconjugates were further characterized by determining their capability to engage in strand exchange with dsDNA. A new method to differentiate between DNA:DNA and PNA:DNA complexes (FIG. 19) was developed based on a knowledge that DNA intercalating dyes show little or no binding to PNA:DNA complexes. Testing of the DNA-binding dye Power Sybr Green (Applied Biosystems) for monitoring DNA dissociation revealed that this DNA dye yields a fluorescent signal that is strong in the presence of dsDNA, but greatly reduced in the presence of PNA:DNA complexes (FIG. 19*a*). The ability of PNA-$TiO_2$ nanoconjugates to outcompete a homologous ssDNA sequence for a complementary ssDNA target was assayed, as determined by a decrease in the derivative of fluorescence intensity peak at the melting temperature of the DNA duplex. Samples containing oligonucleotide dsDNA yielded a characteristically sharp peak indicative of the increased rate of fluorescence loss at the melting temperature (FIG. 19). The addition of free glycidyl isopropyl ether coated nanoparticles had little effect on the fluorescence curve, although a small increase in the peak was observed (FIG. 19*b*). However, the addition of PNA-$TiO_2$ nanoconjugates resulted in over a 50% decrease in the fluorescence derivative peak at the melting temperature of the dsDNA, indicative of reduced dsDNA at this stage (FIG. 19*b*). The addition of free PNAs to an already assembled dsDNA oligonucleotide yielded similar results, affirming that PNA also competes during hybridization (FIG. 19*b*). The magnitude of this signal dampening effect was dependent upon the quantity of PNA-$TiO_2$ nanoconjugates added (FIG. 19*c*), and such reductions in fluorescence and the rate of fluorescence loss were not obtained when PNA-$TiO_2$ nanoconjugates were added to samples of heterologous oligonucleotide dsDNA oligonucleotides (FIG. 19*d*). This indicates that the changes in fluorescence were sequence-specific and caused by the PNA-$TiO_2$ nanoconjugate outcompeting the homologous DNA strand for hybridization with the complementary DNA strand.

TABLE 1

| Sequence name | SEQ. ID. NO.: | Sequence (beginning with N-term or 5' end) |
|---|---|---|
| PNA | 10 | TTTCCTTGGATGTGGT |
| r18S oligonucleotide (homologous to PNA sequence) | 10 | TTTCCTTGGATGTGGT |
| r18AS oligonucleotide (complementary to PNA sequence) | 11 | ACCACATCCAAGGAAA |
| FM20 oligonucleotide | 12 | TTGCTTGGTAGACCAGGCTG |
| FM20AS oligoncleotide | 13 | CAGCCTGGTCTACCAAGCAA |
| r18AS molecular beacon (homologous to r18AS, complementary to r18S and PNA) | 14 | [MHEX]CCCCACCAC ATCCAAGGAAG GGG[MDAB] |
| MS5 molecular beacon (noncomplementary beacon) | 15 | [MHEX]CCCCGAGAGAG AGAGAGAGA GAGAGGGG[MDAB] |
| Sense strand of r18S clone | 16 | TCGAGTTTCCTTGGATGTGGTG |
| Antisense strand of r18AS clone | 17 | AATTCACCACATCCAAGGAAAC |

Figure 20:
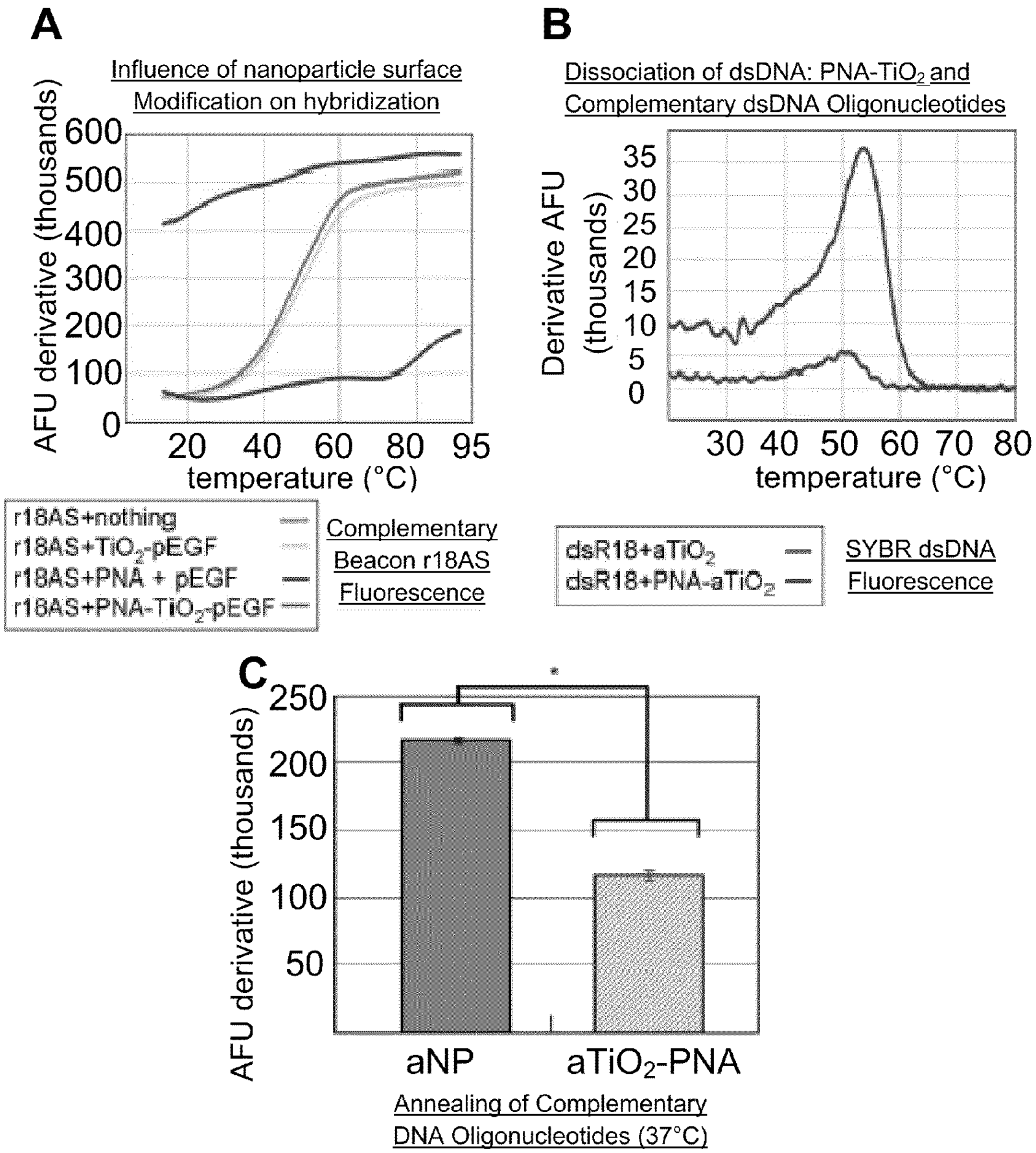
FIG. 20. PNA-$TiO_2$ nanoconjugates retain their hybridization abilities after additional modification of the nanoparticle. (A) PNA-$TiO_2$ nanoconjugates conjugated with pEGF maintain the ability to hybridize to target molecular beacon. (B) Alizarin Red S-coated PNA-$TiO_2$ nanoconjugates (PNA-a$TiO_2$) maintain the ability to outcompete homologous DNA oligonucleotide from an r18S/r18AS dsDNA hybrid (dsR18) oligonucleotide. (C) PNA-a$TiO_2$ nanoconjugates are able to engage in strand exchange with dsDNA at 37° C. under 137-mM sodium conditions, while Alizarin Red S-coated $TiO_2$ nanoparticles (aNP) are not.

Modifications of the Nanoparticle Surface $TiO_2$ nanoconjugates are capable of binding bidentate ligands enabling attachment of additional intracellular targeting agents and/or therapeutic payloads; moreover, carboxyl groups of peptides bind weakly to the nanoparticle surface. Therefore, it is useful to determine the effect of adding such a peptide on the ability of PNA-$TiO_2$ nanoconjugates to hybridize to target DNA. Hybridization-dissociation studies conducted with PNA-$TiO_2$ nanoconjugates coated with an epidermal growth factor peptide segment (pEGF) containing a nuclear localization sequence (NLS) indicate that peptide-modified nanoconjugates maintain the ability to hybridize to complementary molecular beacon (FIG. 19*a*). Peptide-coated nanoconjugates appear to have enhanced hybridization capabilities compared to their naked counterparts (compare fluorescence values at 14° C. in FIGS. 18*b* and 20*a*). These relative comparisons between figures are justified, since all experimental conditions are set against intra-experimental molecular beacon controls. This indicates that peptide coating is not only a useful tool to increase cellular uptake (Thurn et al., Nanoscale Research Letters. 2007, DOI 10.1007/s11671-007-9081-5), but it may also be improving interactions between the nanoconjugate and its molecular beacon target. When PNA alone in the presence of pEGF peptide were used, the molecular beacon showed an aberrant fluorescence curve, perhaps due to interference between the free peptides and reopening of the molecular beacon (FIG. 20*a*). Since no such inhibition was observed with the addition of peptide-coated nanoconjugates or nanoparticles (FIG. 20*a*), the ability of TiO2 to readily bind surface modifiers and alter their function is further accentuated.

Previous studies have shown that Alizarin red s bound to the surface of the nanoparticle permits visualization either in cells (Thurn et al., supra) or in vitro (FIG. 17). Hybridization-competition assays were done to determine whether Alizarin red s when bound to the nanoparticle affects hybridization of PNA bound to the same nanoparticle. Alizarin red s-coated PNA-$TiO_2$ nanoconjugates demonstrated an ability to out-compete homologous DNA in binding with the complementary DNA target as indicated by seven-fold decrease in the fluorescence derivative peak (FIG. 4*b*, compare blue and purple curves). Therefore, Alizarin red s coating did not adversely affect the hybridization behavior of nanoconjugates; in fact, coating the nanoconjugate enhanced the hybridization abilities by a factor of 2½ compared to naked nanoconjugates and naked PNAs (compare FIGS. 20*b* and 19*b*). Furthermore, alizarin-coated PNA-$TiO_2$ nanoconjugates proved able to engage in strand exchange in 137 mM conditions at 37° C. as indicated by a reduction in Sybr Power Green fluorescence in reactions containing dsDNA and nanoconjugates compared to only dsDNA (FIG. 20*c*, $p<0.05$).

Figure 21:
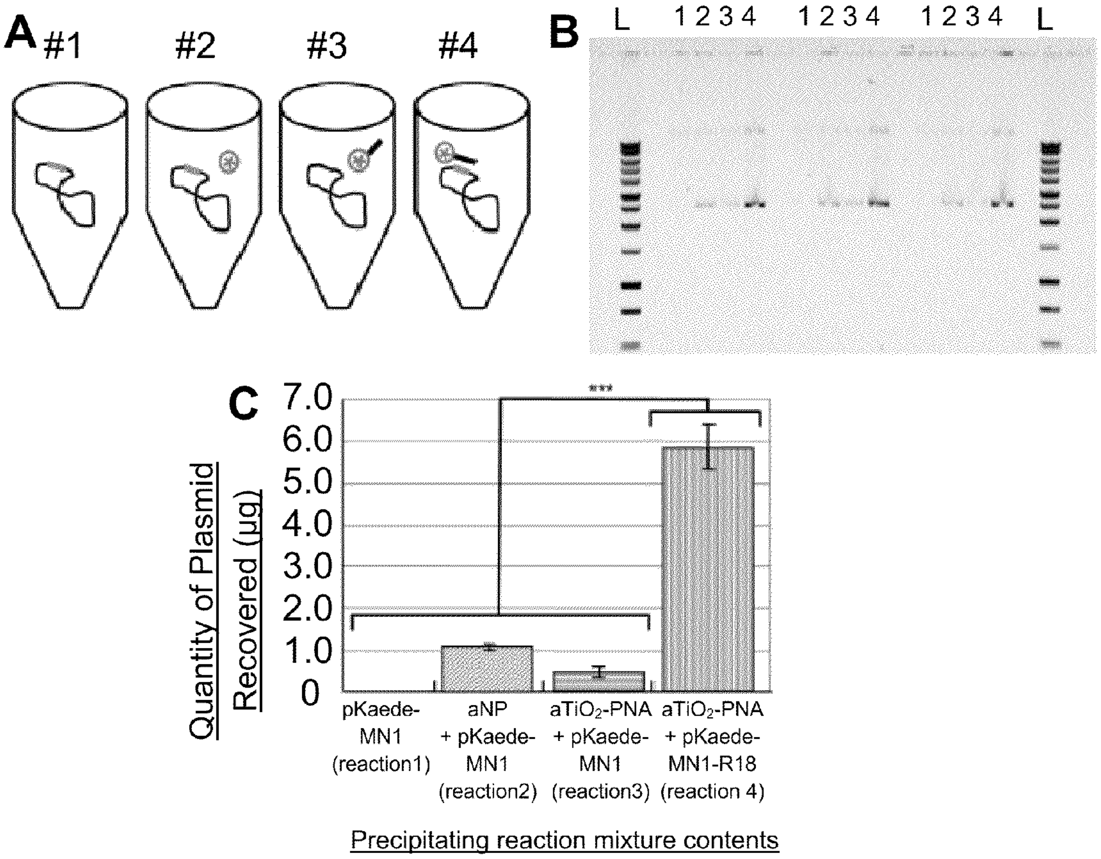
FIG. 21. (A) Schematic of the experimental design for sample preparation for each well type on the gel is shown. (B) Gel demonstrates the ability of PNA-$TiO_2$ nanoconjugates to invade target-containing plasmid DNA pKaede-MN1-R18 (wells containing reaction type 4), at 37° C. in 137 mM sodium, much more avidly than the "empty" pKaede-MN1 plasmid (wells containing reaction type 3), thereby allowing plasmid concentration by precipitation from a 100% aqueous solution.

Ability of PNA-$TiO_2$ Nanoconjugates to Invade Plasmid DNA Containing a Mixed Base Target Under Physiological-Like Temperature and Ionic Conditions The use of PNA-$TiO_2$ nanoconjugates in cellular and whole animals systems depends on their ability to hybridize to complementary DNA under physiological-like conditions, and the sodium concentration affects hybridization of DNA oligonucleotides and PNA strand invasion of duplex DNA. Additionally, targeting of PNAs to previously inaccessible mixed base sequences will allow for increased diversification of potential therapeutic targets. Testing of PNA nanoconjugate behavior under physiological-like temperature and ionic conditions showed that PNA-$TiO_2$ nanoconjugates hybridized well with molecular beacons under such varied conditions (Supplemental FIG. 17*a*-*b*). To affirm that PNA nanoconjugates are able to invade a supercoiled plasmid DNA containing a mixed base target under physiological-like salt and temperature conditions (137 mM sodium, 37.5° C.), we conducted the experiments presented in FIG. 21. For these studies we developed an assay based on the precipitation of $TiO_2$ nanoparticles from aqueous solutions of neutral pH (while plasmid DNA does not precipitate in 100% aqueous solutions) when centrifuged at 0.2 g. pKaede-MN1 (MLB) and pKaede-MN1-R18 plasmids were used, and the only difference between these plasmids was that the latter contains a mixed base sequence that is complementary to the sequence of PNA-$TiO_2$ nanoconjugate (schematically depicted in FIG. 21*a*). All reactions were incubated at 37.5° C. for two hours with periodic mixing followed by centrifugation at 0.2 g to pellet nanoparticles or nanoconjugates. Presence of plasmid DNA in the pellet was then analyzed on an agarose gel (FIG. 21*b*). Three independent experiments are seen on this gel.

As expected, virtually no plasmid was recovered when the plasmid was incubated alone in the aqueous solution (FIG. 21*b*, lanes labeled 1). When Alizarin red s-coated nanoparticles were incubated with the plasmid (FIG. 21*b*, lanes labeled 2) or when Alizarin red s-coated nanoconjugates were incubated with plasmid pKaede-MN1 devoid of a complementary insert R18 (FIG. 21*b*, lanes labeled 3) a small amount of plasmid precipitated. However, a significant quantity of plasmid material was recovered when PNA-a$TiO_2$ nanoconjugates were incubated with the plasmid pKaede-MN1-R18 containing a complementary sequence R18 (FIG. 21*b*, lanes labeled 4). The limited precipitation of the plasmid found in samples 2 and 3 can be explained by non-sequence specific interaction between surface of nanoparticles and polyphosphate of the DNA backbone; the affinity of $TiO_2$ surface sites for polyphosphates was previously established in the literature. Comparisons of these results indicate that recovery of the plasmid in reaction mixture containing TiO2-PNA and supercoiled plasmid with the target sequence was due to the invasion of the supercoiled plasmid DNA (reaction mixture 4) by nanoconjugates in a sequence-specific manner. Rate of plasmid recovery (FIG. 21*c*) indicates that 5.9 μg of the 19.5 μg plasmid sample (30% recovery rate) was achieved by precipitation of plasmid with the PNA target using TiO2-PNA.

Example 4

Labeling $TiO_2$ Nanoparticles with Dyes

A. Experimental

Nanoconjugate Preparation:

All reagents were purchased from Sigma Aldrich unless otherwise specified. $TiO_2$ nanoparticles with mean diameter of around 5-6 nm were synthesized at Northwestern University's Nanofabrication Core of NU-Center for Cancer Nanotechnology Excellence, applying low-temperature alkaline hydrolysis route, dialyzed, and stored in $Na_2HPO_4$ buffer (10 mM) at 4° C. Surface coating with glycidyl isopropyl ether was performed as described previously (Paunesku et al., Nat Mater 2003, 2(5), 343-346). Conjugation of single stranded 5' carboxyl deoxythymidine modified DNA oligonucleotides (ttccttggatgtggt) (The Midland Certified Reagent Co.) to dopamine, and subsequent conjugation to $TiO_2$ nanoparticles was performed as described previously (Paunesku et al., Nat Mater 2003, 2(5), 343-346; Paunesku et al., Nano Lett 2007, 7(3), 596-601; Rajh et al., Nano Lett. 2004, 4(6), 1017-1023). The oligonucleotides were also purchased with either tetramethylrhodamine (TAMRA) or Cy5 3' end modification.

Alizarin Red S Surface Coating and UV-VIS Absorbance Spectrum Analysis:

For determination of covalent surface modification, TiO2 nanoparticles (5 μM) were dialyzed and stored in Na2HPO4 buffer (10 mM) and mixed with Alizarin Red S (0.9 mM). The samples were then analyzed by the Nanodrop ND-1000 Spectrophotometer (Nanoprop Technologies Inc.) for absorbances ranging from 200-750 nm.

Cell Culture and Treatment with Nanoparticles/Nanoconjugates:

All cell culture reagents were purchased from Mediatech Inc. unless otherwise specified. PC-3M metastatic prostate cancer cells were a gift from Dr. Raymond Bergan, Northwestern University. MCF-7/WS8 cells were obtained from American Type Culture Collection (ATCC). Both cell lines were maintained at 37° C. with 5% CO2 in RPMI 1640 media supplemented with fetal bovine serum (10%), L-glutamine (2 mM), HEPES (10 mM), penicillin (100 I.U./ml), streptomycin (100 μg/ml). MCF-7 cells were further supplemented with non-essential amino acids (1×), amphoterecin B (0.25 μg/ml), and insulin (0.1 mg/ml) (Sigma-Aldrich). PC-3M cells were further supplemented with G418 sulfate (0.15 mg/ml). For treatment, cells were washed with phosphate buffered saline solution (PBS) and placed in serum free RPMI 1640 for 1-2 hours. Then cells were treated with $TiO_2$ nanoparticles (333 nM) coated with or without ARS (60 μM), and/or ODN (160 μM) for one hour. After treatment, cells were washed with PBS, and then in glycine (200 mM, pH 4) (Sigma Aldrich). After more washing in PBS, the cells were further prepared as described below, depending on the technique performed.

Flow Cytometry and Cell Sorting:

Cells to be analyzed by flow cytometry were grown until approximately 60% confluence. After treatment and washing, cells were trypsinized, collected in FBS supplemented medium, and brought to a single cell suspension. To determine cell viability, cell samples were treated with DAPI (5 μg/ml) (Molecular Probes, Invitrogen) prior to analysis. Samples were then taken to the Northwestern University Flow Cytometry Core Facility of the Robert H. Lurie Cancer Center to be analyzed or sorted on the DakoCytomation MoFlo Flow Cytometer (Dako). Excitation lasers of 350 nm and 543 nm were used to excite DAPI and TAMRA/ARS, respectively. Debris was excluded based on the forward and side scatter characteristics of the cell populations. Analysis of flow cytometry data was performed using the FCS Express V3 program (De Novo Software).

Confocal Microscopy:

For visualization by confocal microscopy, cells were cultured on glass coverslips. Cells at approximately 60% confluence were treated and washed as described above. The cells were then fixed in parformaldehyde (4%), and stained with Hoechst 33343 (Molecular Probes, Invitrogen). After washing the cells were placed in anti-fade mounting medium (Molecular Probes, Invitrogen) and visualized using the LSM 510 UV Meta Microscope (Carl Zeiss, Inc.) at the Northwestern University Cell Imaging Facilities using 405 nm, 488 nm, and 543 nm lasers with bandpass filters of 420-480 nm, 505-530 nm, 560-615 nm, respectively.

X-Ray Fluorescence Microscopy (XFM):

Cells transfected with $TiO_2$-DNA (TAMRA) nanoconjugates were sorted for the presence of TAMRA, seeded on formvar coated gold EM grids (Electron Microscopy Sciences) and allowed to adhere. The samples were then fixed in cold methanol (−20° C.), and stained with Hoechst 33342 dye. The samples were placed in anti-fade mounting medium between a glass coverslip and slide, and imaged by confocal microscopy. Next, the cells were washed in glycine and PBS, dehydrated in ethanol (100%), and allowed to air dry. Before XFM analysis, the presence of the cells was verified, and coordinates for their locations were obtained by the Leica DMXRE light microscope and a motorized x/y stage (Ludl Electronic Products). XFM was performed at the 2-ID-D beamline at the Advanced Photon Source at Argonne National Laboratories where an undulator source was used to create hard X-Rays with energies of 10 keV and focused using Fresnel zone plate optics. Emitted X-Ray fluorescence was detected using an energy dispersive germanium detector (LEGe Detector, Can berra). Elemental quantification and localizations were calculated using the MAPS program (Vogt, J. Phys. IV 2003, 104(635-638).

B. Results

Figure 22:
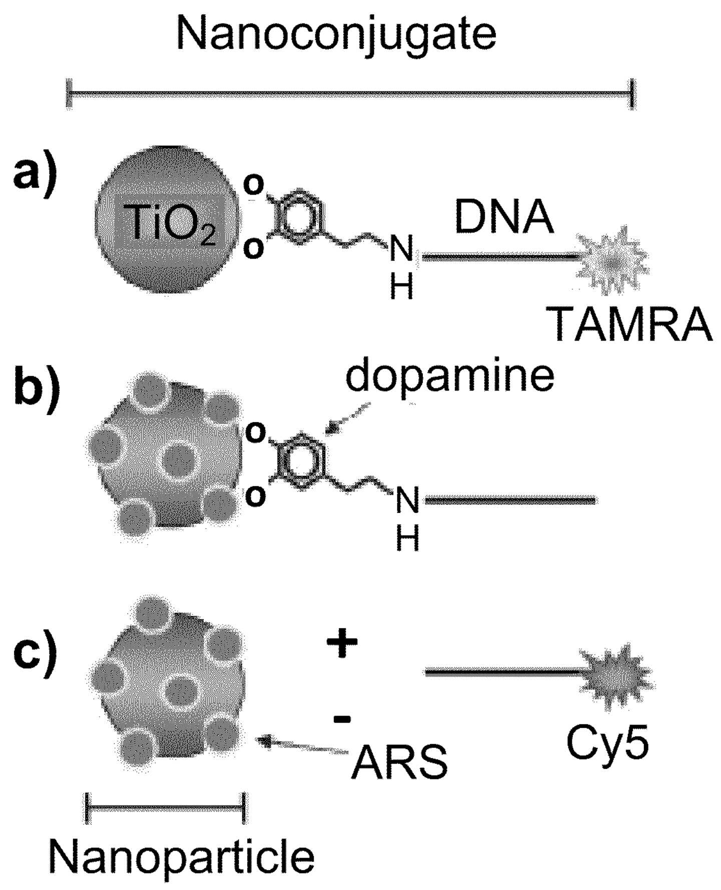
FIG. 22. Schematic representation of fluorescent labeling of $TiO_2$-DNA nanoconjugates. a. DNA oligonucleotides are 3' labeled with tetramethylrhodamine (TAMRA), while the 5' carboxyl dT terminal end is modified with dopamine which subsequently binds the surface defects of $TiO_2$ nanoparticles <20 nm. b. Direct covalent conjugation of Alizarin Red S (ARS) to the undercoordinated surface defects of $TiO_2$ nanoparticles creating an ARS labeled $TiO_2$-DNA nanocomposite. c. Direct ARS labeling of nanoparticle with the addition of free, unbound Cy5 labeled DNA oligonucleotides.

One of the limiting factors in $TiO_2$ nanoparticles studies is the lack of diversity in available intracellular detection techniques. Taking advantage of the surface chemistry of $TiO_2$ nanoparticles, the nanoparticle/nanoconjugates were fluorescently labeled by two separate approaches. At 20 nm or below, the metal oxide nanoparticle's surface geometry changes from a pentacoordinated to a hexacoordinated position (Rajh et al., J. Phys. Chem. B 1999, 103(18), 3515-3519). These undercoordinated "surface defects" have a high affinity for ortho-substituted enediol ligands (e.g. dopamine, alizarin, ascorbic acid) that restore the surface titanium atom's coordination back to its relaxed, octahedral form upon binding (Rajh et al., J. Phys. Chem. B 1999, 103(18), 3515-3519; Rajh, O. Poluektov, A. A. Dubinski, G. Wiederrecht, M. C. Thumauer, A. D. Trifunac, Chem. Phys. Lett. 2001, 344(1-2), 31). DNA oligonucleotides that had their 5' dT terminal ends carboxyl modified, were bound to dopamine as described earlier (Paunesku et al., Nat Mater 2003, 2(5), 343-346; Paunesku et al., Nano Lett 2007, 7(3), 596-601; Rajh et al., 2004, 4(6), 1017-1023). Their 3' terminal ends were labeled with either fluorescent tetramethylrhodamine (TAMRA) or Cy5. The 5' dopamine modified end was then used to covalently link the DNA oligonucleotide directly to the surface of the nanoparticle creating a stable $TiO_2$-dopamine-DNA nanoconjugate with a fluorescently labeled nucleic acid component (FIG. 22).

Figure 23:
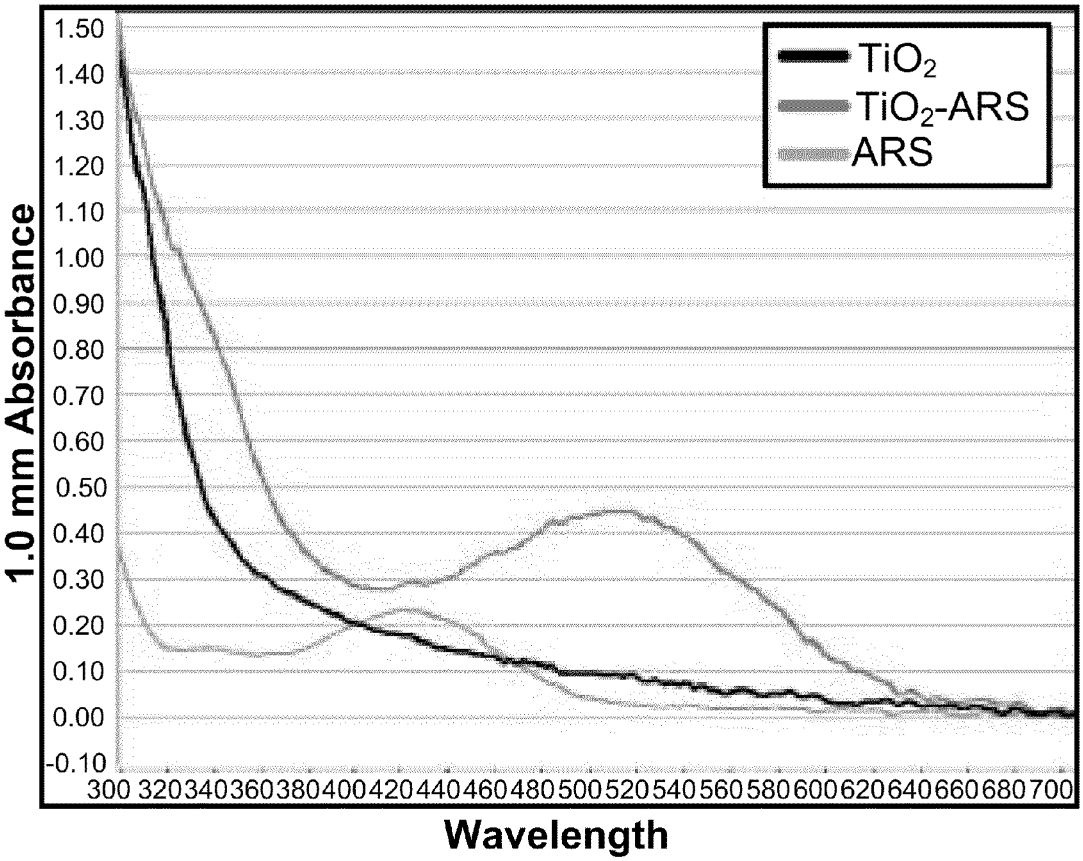
FIG. 23. UV-VIS absorbance spectrum of $TiO_2$, ARS, and ARS coated $TiO_2$ nanoparticles.

In order to establish a simple, inexpensive, and covalent process to fluorescently label the nanoparticle directly for intracellular detection, the surface of the metal-oxide nanoparticles was modified with Alizarin Red S (ARS). It was contemplated that binding of ARS to nanoparticles would render them highly fluorescent since locally high concentrations of ARS molecules increase their local concentration and light absorbance. ARS (a derivative of alizarin) is an ortho-substituted enediol ligand that has never been previously reported to be used as an intracellular label for $TiO_2$ nanoparticles. ARS has been used in optical microscopy for fluorescent labeling of calcium deposits. Since the same hydroxyl groups of ARS are significant in the binding to both calcium and $TiO_2$ (Puchtler et al., Cytochem. 1969, 17(2), 110-124), the nanoparticle bound ARS should be precluded from binding calcium. It has been reported that ARS is able to form complexes with proteins at low pH (3.6), although this was almost completely inhibited as pH values approached physiological conditions (Zhong et al., 2004, 62(1), 37). For direct surface binding to the nanoparticle, ARS was added to 5 nm $TiO_2$ nanoparticles. The nanoparticles' UV-VIS absorbance spectra were analyzed since surface modification of the nanoparticle will cause a change in absorbance. Results from FIG. 23 show that $TiO_2$ nanoparticles show absorption wavelengths smaller than 350 nm. Conjugation of 44% of the total surface titanium atoms with ARS ($TiO_2$-ARS) caused a red shift and creation of a unique absorption maximum at 510 nm. This fluorescence could be excited at relatively long wavelengths (absorption peak at 510 nm is very broad) which have higher tissue/cell penetrance than the UV wavelengths. The UV-VIS absorbance spectra of the TiO2-ARS complex was very similar to those published of $TiO_2$-Alizarin. This is not surprising since the two polycyclic aromatic molecules differ only in the addition of a sulfonate group on ARS (1,2 dihydroxyanthraquinone vs. 1,2 dihydroxyanthraquinone-3-sulfonate). ARS alone at the same concentration had an absorbance peak at 420 nm.

Figure 24:
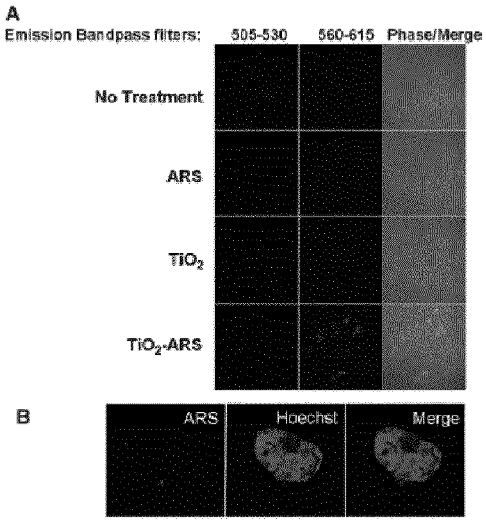
FIG. 24. Intracellular detection of ARS modified $TiO_2$ nanoparticles. A. PC-3M cells were either untreated, treated with 60 μM ARS, or treated with 333 nM of $TiO_2$ nanoparticles that were either unmodified ($TiO_2$) or ARS coated ($TiO_2$-ARS). B. Labeling intracellular $TiO_2$ nanoparticles in fixed cells.

To determine if the ARS modified nanoparticles in cells are detectable by fluorescent confocal microscopy, prostate cancer PC-3M and breast cancer MCF-7 cells were serum-starved and treated with ARS coated $TiO_2$ nanoparticles ($TiO_2$-ARS). As controls, cells were left untreated, treated with ARS alone, or treated with uncoated $TiO_2$. Absolute ARS and nanoparticle concentrations were the same in each case. The treated cells were then imaged using two separate excitation lasers: 488 nm and 543 nm. A previous study claimed to have detected $TiO_2$ nanoparticles directly using an excitation laser of 488 nm with emission filters between 505-550 nm (Suzuki et al., Environ Sci Technol 2007, 41(8), 3018-3024). FIG. 24A, third row shows the results when similar experimental and microscopy parameters are used. Cells were treated with the nanoparticles and were not washed with 200 mM glycine which lead to a significant accumulation of nanoparticles on the cell surface. In all other experiments described here gycine wash was performed in order to ensure that only those nanoparticles that were internalized remain associated with cells. Microscopy conditions were low power magnification with 488 nm excitation laser and a 505-530 nm bandpass filter for signal detection. Under these precise conditions bare $TiO_2$ did not exhibit a detectable fluorescent signal. The difference may perhaps be caused by different properties/sizes of nanoparticles (23 nm vs. 5 nm), different degree of nanoparticle accumulation within cells, or different degree of background fluorescence. Treatment of cells with $TiO_2$-ARS (fourth row) did, however, result in a strong fluorescent signal in the range of 560-615 nm when excited with a 543 nm laser. Thus ARS modified nanoparticles are fluorescent emitting at 560-615 nm wavelengths where little background fluorescence from can be expected. Importantly, cells treated with ARS alone did not produce a detectable fluorescent signal with either excitation laser. Non-specific retention of ARS did not occur within the cells under the conditions tested, and ARS was not able to form significant fluorescent intracellular complexes without conjugation to the $TiO_2$ nanoparticle.

In order to determine if post-treatment fluorescent labeling of nanoparticles already internalized into cells with ARS was possible, PC-3M cells were treated with unlabeled nanoparticles, fixed, and subsequently stained with an ARS solution in phosphate buffered saline solution (PBS). Results in FIG. 24B show a detectable intracellular ARS fluorescence within the cytoplasm. The fixed cells that were not previously treated with TiO2 did not exhibit a detectable fluorescent signal upon treatment with the ARS solution (FIG. 24A). This indicates that internalization of nanoparticles was not due to ARS coating, and that ARS was able to bind intracellular $TiO_2$ particles in fixed cells.

Figure 25:
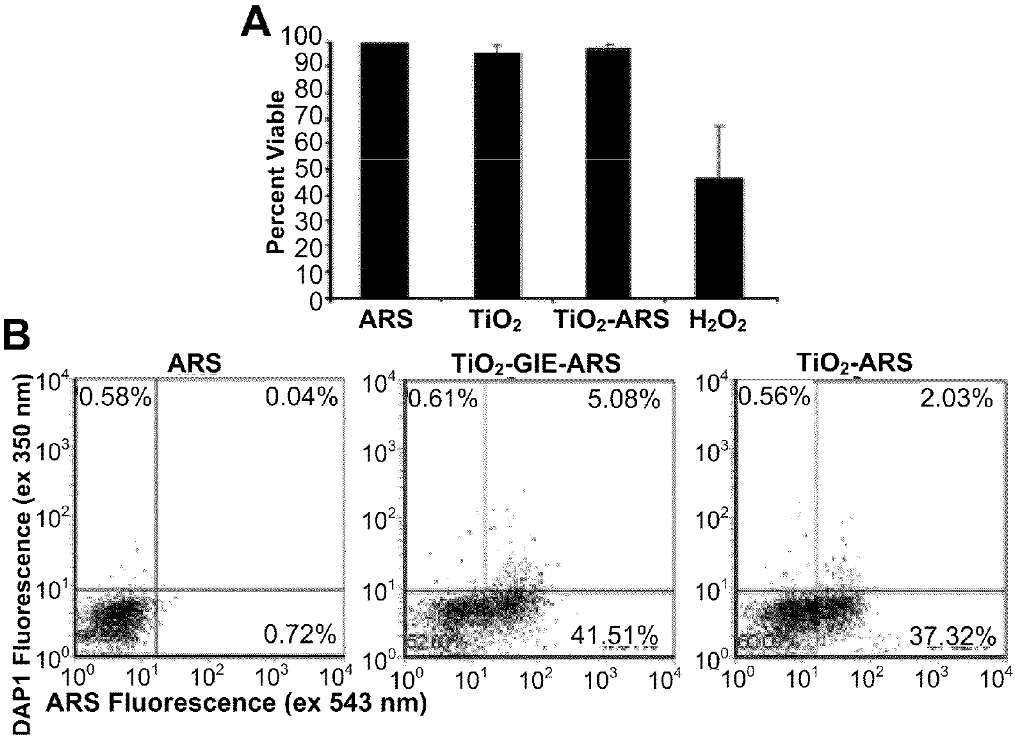
FIG. 25. $TiO_2$ nanoparticles uptake and effect on cell viability. A. PC-3M cells were treated with 60 μM ARS, 333 nM ARS labeled GIE coated nanoparticles ($TiO_2$-GIE), ARS labeled uncoated $TiO_2$ nanoparticles ($TiO_2$-ARS), or 20 mM hydrogen peroxide ($H_2O_2$) for 24 hours. B. A representative plot obtained from one of three independent experiments.

Glycidyl isopropyl ether (GIE) has previously been conjugated to the surface of $TiO_2$ nanoparticles ($TiO_2$-GIE) in order to reduce bio-reactivity of the nanoparticle within cells (Paunesku et al, 2003, supra; Paunesku et —, 2007, supra). The use of uncoated $TiO_2$ nanoparticles produces an abundance of reactive oxygen species upon excitation which can be used for cell killing without gene specific targeting (Zhang et al., World J Gastroenterol 2004, 10(21), 3191-3193; Seo et al., Small 2007, 3(5), 850-853). The viability of cells that have taken up GIE coated or uncoated TiO2 nanoparticles was determined. Viability assays require investigation of thousands of cells and is difficult in conjunction with TEM or XFM. Labeling the nanoparticles, however, allowed one to screen the treated cells simultaneously for nanoparticle uptake (by ARS fluorescence) and for viability (by use of fluorescent cell-impermeable dye). PC-3M cells were treated with GIE coated and uncoated $TiO_2$ nanoparticles labeled with ARS. As a control, 20 mM hydrogen peroxide ($H_2O_2$) was used as an inducer of cell death (Whittemore et al., Neuroscience 1995, 67(4), 921). Flow cytometry was then used to quantify both the extent of nanoparticle uptake within the cell population, and the cells' ability to exclude cell-impermeable DAPI as an indicator of cell viability. Results show that when treated with ARS alone, virtually the entire population of cells was viable and capable of dye exclusion (FIG. 25A). Both of the $TiO_2$ nanoparticles treated cells ($TiO_2$-GIE-ARS and $TiO_2$-ARS) showed no significant decrease in viability, with the number of dead cells averaging 5% and 2%, respectively (n=3). $H_2O_2$ treated cells, on the other hand, showed an approximately 54% reduction in viability. This indicates that neither $TiO_2$-ARS nor $TiO_2$-GIE-ARS nanoparticles had a significant effect on cell viability at the concentration used in the experiments described herein. These results were confirmed in MCF-7 cells.

While simultaneously detecting cell viability, samples were also analyzed for ARS fluorescence as an indicator of nanoparticle uptake. Extensive washing in low pH glycine was demonstrated to reduce oligonucleotide binding to the cell surface (Whittemore et al, supra). It was found that it also reduced the extent of nanoparticle binding to the cell membrane. This ensured that detectable ARS fluorescence came from nanoparticles located within cells and was not membrane-bound. Internalization of nanoparticles was shown by the number of cells excited to fluoresce using similar parameters to those performed during microscopy. FIG. 25B is a representative plot of several experiments performed (n=3), showing that cells treated with ARS alone exhibited very low auto-fluorescence (excitation with 543 nm laser, emission in 560-615 nm range). Cells treated with $TiO_2$-GIE-ARS showed an average nanoparticle uptake of 36% within the cell population, while $TiO_2$ nanoparticles lacking GIE had a similar nanoparticle internalization of 32%. This indicates that GIE did not significantly aid in the internalization of the nanoparticle, nor did it affect viability of cells. ARS could be used by both confocal microscopy and flow cytometry to detect intracellular $TiO_2$ nanoparticles.

To determine the subcellular localization of the separate components of the $TiO_2$-DNA nanoconjugates, cells were treated simultaneously with both $TiO_2$-ARS nanoparticles and free Cy5 labeled unbound DNA oligonucleotides. After treatment and washes, the cells were imaged by confocal microscopy. Results show that there was a strong accumulation of the ARS labeled nanoparticles within endosomal vesicles within the cytoplasm. The subcellular distribution was similar to that seen when the alizarin red s was used for post-treatment staining (FIG. 24*b*). This indicates that the uptake mechanism was not altered due to alizarin red s surface labeling. The free oligonucleotides, on the other hand, showed a strong localization within the nuclei, and more strikingly within the nucleoli. This was similar to the results previously obtained with free oligonucleotides (Laktionov et al., Nucleic Acids Res 1999, 27(11), 2315-2324; Nestle et al., J. Invest. Dermatol. 1994, 103(4), 569-575; Noonberg et al., J. Invest. Dermatol. 1993, 101(5), 727-731) and with complete nanoconjugates (Paunesku et al, 2003, supra; Paunesku et al, 2007, supra). These results demonstrated that the separate components of the nanoconjugates (the nanoparticle and DNA oligonucleotide) accumulated in separate subcellular organelles and did not co-localize within the same cell if not covalently bound together. This indicates that the separate components enter the cell via unique internalization mechanisms, or are distinctly trafficked within the cell.

Since the functionality and targeting of the nanoconjugates are greatly dependent on their integrity, confocal microscopy was combined with X-Ray Fluorescent Microscopy (XFM) to track both components independently within the same cell. Confocal microscopy was used to detect the DNA oligonucleotide component, while XFM was used to directly detect titanium (and thereby the nanoparticles). XFM was performed at the 2-ID-D beamline at the Advanced Photon Source at Argonne National Laboratories. XFM mapped the location and concentration of elements ranging from phosphorus to zinc on the periodic table (including titanium) using raster scanning with step sizes of 0.3 μm.

Confocal microscopy revealed several small accumulations of the TAMRA labeled DNA oligonucleotides within the cytoplasm and a stronger signal aligned with the nucleus. XFM analysis revealed a distribution of titanium that was very similar to that of TAMRA. The phosphorus map also revealed a strong co-localization with titanium and TAMRA. This is probably an artifact due to the fixing, staining, and mounting techniques involved in sample preparation. Titanium concentration, however, was determined only by the presence of nanoparticles. The number of nanoparticles located within the specified regions of interest (ROI) was quantified. ROI 1 corresponds to a detectable XFM titanium signal ($3.1\times10^4$ nanoparticles) although the TAMRA signal of this nanoparticle accumulation was only very weakly visible. Each nanoparticle was modified by approximately 2 TAMRA labeled oligonucleotides so that the optically fluorescent signal corresponds to $6.2\times10^4$ TAMRA molecules. The strongest titanium signal came from ROI 3 and showed the presence of approximately $1.3\times10^6$ nanoparticles. Confocal microscopy also showed a clearly detectable TAMRA signal within the same relative subcellular area. There are several titanium distributions obtained by XFM that were not imaged by confocal microscopy. This is likely due to the fact that the hard X-rays used in XFM are able to penetrate the entire cell, while confocal microscopy imaged optical cell slices of 0.13 μm thickness. To verify this, multiple planes of cells treated with ARS labeled $TiO_2$-DNA nanoconjugates were visualized by confocal microscopy and subsequently imaged by XFM. Results showed that accumulations of the ARS labeled $TiO_2$-DNA nanoconjugates were not visible in one plane of microscopy, but were visible in different planes. At the same time, however, both of the aggregates were shown to overlap with titanium. As few as $7.9\times10^4$ nanoparticles were detectable by fluorescence microscopy when 44% of the total surface of the $TiO_2$ nanoparticle was coated with ARS. The overall similarity in the distributions of both TAMRA labeled DNA oligonucleotide and titanium nanoparticle indicates that the integrity of the $TiO_2$-DNA nanoconjugates remains intact at the time point examined (12 hours).

Example 5

Assembling Titanium Dioxide Nanoparticles by DNA Molecule Hybridization and Loading DNA Interacting Proteins A. Experimental (1) Conjugation of DNA Oligonucleotides to $TiO_2$ Nanoparticles The preparation of colloidal $TiO_2$ was conducted as described (Paunesku et al, Nature Mater. 2003, 2, 343-346). Briefly, synthesis was done in aqueous solution by adding $TiCl_4$ dropwise to cooled water. Nanoparticles of 3-6 nm were prepared. Previous work has shown $TiO_2$ spheres of this size are anatase crystals; their conjugation with dopamine is stable for years, therefore stability of nanoparticle-oligonucleotide nanoconjugates matches stability of free DNA oligonucleotides which is about one month at 4° C. (Paunesku et al, Nature Mater. 2003, 2, 343-346; Rajh et al J. Phys. Chem. B 2002, 106, 10543-10552). DNA oligonucleotides used in these experiments were “T2” 5' carboxy dTCAGCCTGGTCTACCAAGCAAACTCCAGTACAGCCAGGGAACATGAGAGAC 3' (SEQ ID NO:4) and “T5” 5' carboxy-dT-GTCTCTCATGTTCCCTGGCTGTACTGGAGTTTGCTTGGTAGACCAGGCTG 3' (SEQ ID NO:5). These oligonucleotides (Midlands Scientific, TX) were synthesized to be complementary to each other; together they hybridize into double-stranded DNA. Synthesis was carried out so that both oligonucleotides have a 5' terminal carboxyl group; oligonucleotide stocks are stored frozen at −80° C. as a 100 μM stock solution in 10 mM $Na_2HPO_4$ phosphate buffer (10 mM phosphate; 20 mM sodium) at pH 6.5. A condensation reaction through intermediate N-hydroxyl-succinimide ester was used to bind the carboxyl group of the oligonucleotide to the amino group of dopamine by an amide bond (Boncheva et al Langmuir 1999, 15, 4317-4320). Briefly, the DNA terminal carboxyl group of oligonucleotides is bound to O—N-succinimidyl-N,N,N',N'-tetramethyluronium tetrafluoroborate (TSTU) in the presence of N,N-diisopropylethyl amine (i-PRTEN) in N,N-Dimethylformamide (DMF). In the second step, the succinimidyl group is replaced with dopamine through its terminal amino group in the presence of dioxane. This solution was thoroughly dialyzed against water to remove free dopamine unbound to oligonucleotides. In the final step, dopamine end-labeled oligonucleotides are bound to $TiO_2$ particles modified by glycidyl isopropyl ether (GIE) (Paunesku et al, Nature Mater. 2003, 2, 343-346). The stability of the dopamine-surface $TiO_2$ complex is stronger than the stability of the complex formed between the $TiO_2$ surface and glycidyl isopropyl ether, and therefore dopamine easily replaces GIE at the nanoparticle surface (Rajh et al J. Phys. Chem. B 2002, 106, 10543-10552). At the conclusion of this procedure nanoconjugates are stored in 10 mM $Na_2HPO_4$ phosphate buffer pH=6.5. The amide bond between dopamine and oligonucleotide is stable, and the stability of the bond between dopamine and the surface of the $TiO_2$ nanoparticle is also great. Thus, oligonucleotide-modified nanoparticles behave similar to 'free' oligonucleotides, and they are stable for up to one month when stored in the refrigerator at 4° C.

Because dopamine modified oligonucleotides readily bind nanoparticle surface, methods developed during the course of the present invention allowed accomplishment of different DNA oligonucleotide loading per nanoparticle by using different mixing ratios of nanoparticles and oligonucleotide DNA molecules. Rapid mixing of the two components of the nanoconjugate lead to a reaction where average number of oligonucleotides per nanoparticle is controlled by DNA:nanoparticle stoichiometry. Two different ratios of DNA oligonucleotide: nanoparticle were used to achieve high DNA or low DNA oligonucleotide loading per nanoparticle. For high DNA loading per nanoparticle 50 μL of 100 μM T2 or T5 oligonucleotide was mixed with 200 μL of 10 μM of nanoparticle; for low DNA loading per nanoparticle 50 μL of 20 μM T2 or T5 oligonucleotide was mixed with 200 μL of 10 μM of nanoparticle.

(2) Annealing of Complementary DNA-$TiO_2$ Nanoconjugates.

For the creation of double-stranded $TiO_2$-dsDNA-$TiO_2$ nanoparticle dumbbells and $[—TiO_2\text{-dsDNA-}]_n$ superstructures, $TiO_2$-T2 and $TiO_2$-T5 nanoconjugates were mixed in equal molar ratios and incubated for 3 min at 95° C. followed by gradual cooling to room temperature overnight. Because these nanoconjugates were suspended in 10 mM disodium phosphate buffer, presence of sodium (20 mM final concentration) aided the hybridization. Generally, hybridization reactions often require higher concentrations of sodium; nevertheless, oligonucleotides used were 50 mers and their hybrids were very stable in 20 mM sodium, with about 65° C. melting temperature. In those cases when nanoparticle superstructures were to be embedded in agarose, pre-melted 2% agarose in 10 mM disodium phosphate buffer pH=6.5 was added to the nanoparticles V:V at 95° C. As agarose solidified, it embedded the $[—TiO_2\text{-dsDNA-}]_n$ superstructures in 3D space. All of these reactions were carried out in total volumes of 200 to 400 μL.

For PCNA protein loading onto the nanoconjugates, nanoconjugates with double strand DNA were prepared by annealing between $TiO_2$-T2 nanoconjugate and free T5 oligonucleotide. Purified PCNA protein was mixed with $TiO_2$-dsDNA in a molar ratio in excess of 3:1 because PCNA protein loads onto DNA by forming trimers (Tom et al J. Biol. Chem. 2000, 275, 10498-10505).

(3) Proliferating Cell Nuclear Antigen (PCNA) Protein Cloning and Isolation

PCNA gene cDNA was synthesized by reverse transcription and polymerase chain reaction (RT-PCR) using PCNA specific primers (sense 5'atgttcgaggcgcgcctggtc (SEQ ID NO:6) and antisense 5' agatccttcttcatcctcga (SEQ ID NO:7). Once cloned and verified by sequencing, this coding DNA was re-cloned into a plasmid pEF6/V5-His (Invitrogen) wherein additional coding sequence was added at the C or N terminus of the PCNA coding sequence, introducing a V5 epitope and six consecutive histidine amino acids at either end of the PCNA protein coding sequence. These additional histidines allowed the cloned protein to be purified on a nickel-containing column, using Ni column kit (Quiagen). Epitope V5 of the PCNA protein is used for immunohistochemistry differentiation between native and cloned protein. The human breast cancer cell line MCF-7/WS8 (American Type Culture Collection) was grown in 5% $CO_2$ in RPMI1640 media supplemented with 10% fetal bovine serum, with the addition of antibiotic and antimycotic. Recombinant PCNA gene was introduced into the cells complexed with the SuperFect Reagent (Qiagen). Three days after transfection recombinant PCNA protein was isolated and a nickel-containing bead column (Dynal) was used for protein purification. A standard Western blot was used to confirm the size of the purified protein (data not shown).

(4) PCNA Protein Function Verification

MCF-7/WS8 human breast cancer cells were grown on glass coverslips until they reached ~40% confluency, and then they were transfected with a recombinant PCNA gene construct. After 24 hours, transfected cells were rinsed in phosphate buffered saline (PBS), fixed in ice-cold methanol for 5 minutes, and rinsed again with PBS containing 0.01% Tween and 0.5% bovine serum albumin (BSA) prior to staining with antibodies. Transfected cells were stained with an antibody against the V5 epitope (anti-V5 mouse antibody, Invitrogen), present in the recombinant PCNA protein, and a secondary antibody (rabbit anti-mouse antibody labeled with rhodamine, Rockland); while control cells were stained for endogenous PCNA (mouse anti-PCNA FITC-conjugated antibody, Chemicon International). All cells were rinsed three times with a PBS-Tween-BSA solution, mounted on slides using a PPD mounting media (1 mg/mL P-phenylenediamine, 10 mM Tris buffer at pH 8.5 and 50% glycerol, all components obtained from Sigma), and imaged by confocal fluorescence microscopy to determine if the recombinant PCNA displayed during synthesis phase (S phase) of the cell cycle shows the same subcellular localization patterns as endogenous (non-recombinant) PCNA.

(5) Sample Preparation for Transmission Electron Microscopy (TEM)

For each TEM sample 6 μL of nanoconjugates, hybridized nanoconjugates or nanoconjugate superstructures were stained with 5 μL of 1.5% uranyl acetate solution and deposited on gold grids with carbon film coating for support. Uranyl acetate staining was done in order to stain DNA and allow imaging of the DNA components of the nanoconjugates under the electron beam (Zobel et al, J. Biophys. Biochem. Cytol. 1961, 11, 336-346). These samples were rinsed in double distilled water three times, excess water was removed by filter paper and the samples were dried for 1-3 hours before storage.

The samples embedded in agarose were processed as it is usually done with cultured cells prepared for TEM (Strausbauch et al, J. Electron Microsc. Tech. 1985, 2, 261-262). Nanoconjugates with complementary DNA sequences were first allowed to hybridize in solution as it was cooling from 90° C. to 50° C. At that temperature, melted agarose at 50° C. was added to these samples and their cooling continued until they reached room temperature. During cooling the agarose was gradually solidifying thus capturing the hybridized nanoconjugate network in 3D space; from being free floating in suspension, the network became embedded in agarose substrate. Subsequently, the agarose block with 3D mesh structure suspended in it in 3D was cut into 1-2 mm cubes, dehydrated in a series of solvents commonly used for preparation of cells and tissues as TEM samples; in the end, final solvent was replaced by epon resin. Finally, liquid resin solution permeating the agarose was solidified by baking. Once embedded in resin these samples were sectioned at roughly 200 nm, stained by uranyl acetate and imaged at the Cell Imaging Facility. Uranyl acetate does not stain the agarose but it does stain DNA, as known from the studies of agarose embedded cultured cell samples imaging by TEM (upon staining, cell nuclei are very visible while agarose matrix remains entirely transparent).

(6) Sample Preparation for Atomic Force Microscopy

The freshly cut mica was used as an imaging substrate. Usually, 5 μL of 5 mM of $MgCl_2$ solution was deposited on the newly cleaved mica surface to create a positive charged interface to immobilize the negatively charged $TiO_2$-DNA nanoconjugates. After 5-10 minutes, the modified surface was rinsed with double distilled water and pure ethanol three times each to remove the unbound $Mg^{2+}$ and other inorganic and organic impurities.

For preparation of nanoconjugates with PCNA protein loaded onto them, low DNA loading nanoconjugates $TiO_2$-T2 and free complementary oligonucleotides T5 to anneal $TiO_2$-dsDNA nanoconjugates were used. A drop of 20 μL of these nanoconjugates were mixed with purified recombinant PCNA protein from 10 million MCF-7/W8 cells transfected with the recombinant PCNA gene in a buffer containing 30 mM HEPES (pH 7.6), 5% glycerol, 40 mM KCl, and 8 mM $CaCl_2$ thus modifying a procedure published by others (Tom et al J. Biol. Chem. 2000, 275, 10498-10505). After application of the sample onto mica, extensive washes were performed.

2) Equipment (1) UV-Visible Light Spectrometry

The optical properties of $TiO_2$ nanoparticles, $TiO_2$-T2 and $TiO_2$-T5 ($TiO_2$-ssDNA) nanoconjugates and hybridized $TiO_2$-T2-T5-$TiO_2$ ($TiO_2$-dsDNA-$TiO_2$ and [—$TiO_2$-dsDNA-$]_n$) nanoconjugate solutions and superstructures were monitored by NanoDrop (ND-1000) spectrophotometer (NanoDrop Technologies, Wilmington, Del., USA). Each time 2 μL of sample solution was used for measurement.

(2) Transmission Electron Microscopy (TEM)

A JEOL 1220 transmission electron microscope at Cell Imaging Facility at Northwestern University, equipped with a megapixel-resolution Kodak digital camera and operated at 60 kV, was used for measurements.

(3) AFM Imaging

AFM images were acquired using a Digital Instruments Multimode atomic force microscope (Veeco Instruments, Santa Barbara, Calif.) equipped with a NanoScope IIIa controller and an E-scanner, at NUANCE center of Northwestern University. Imaging was performed in tapping mode in air. Single-crystalline ultrasharp silicon tips were used (Veeco Instruments) for imaging. These AFM silicon probe tips have 20-50 nm diameter; therefore the images of structures smaller than 20 nm are difficult to distinguish and appear deformed compared to the original structures (Hansma et al Nucl. Acids Res. 1996, 24, 713-720; Wu et al Anal. Biochem. 2004, 325, 293-300; Niemeyer et al ChemPhysChem. 2001, 2, 374-388). All images are presented after flattening.

(4) Confocal Fluorescent Microscopy

An LSM 510 laser scanning confocal microscope (Zeiss) at the Northwestern University Cell Imaging Facility was used. Excitation lasers and emission filters for fluorophores were set as follows: for rhodamine 543 nm and 560-615 nm and for FITC 488 nm and 505-530 nm. An optical slice of approximately 1 μm was taken through the midsection of the cell nucleus.

B. Results and Discussion

Figure 26:
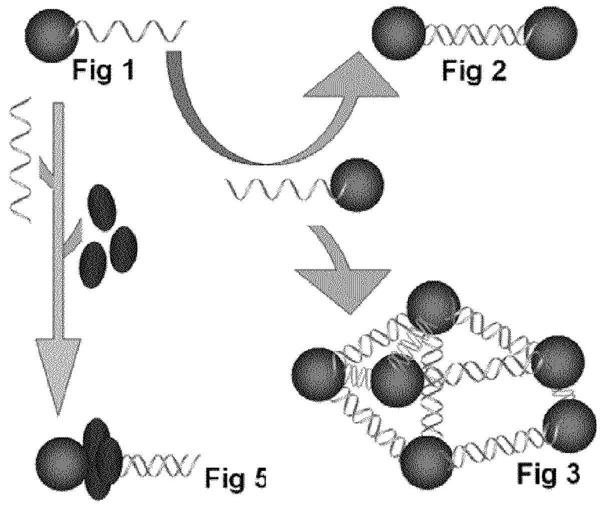
FIG. 26. A schematic presentation of preparation of $TiO_2$ nanoconjugate assemblies.

A method developed during the course of the present invention for assembling $TiO_2$ nanoparticles to form either 2D structures such as dumbbells or 3D net superstructures is shown in FIG. 26.

First, the 5' terminal carboxyl groups of DNA oligonucleotides T2 and T5 (for their sequences see Materials Section) were each conjugated with dopamine molecules to form two dopamine-single stranded DNA complexes. Secondly, these oligonucleotides were conjugated separately with $TiO_2$ nanoparticles to form $TiO_2$-ssDNA nanoconjugates via bidentate complexes between the —OH groups of dopamine and undercoordinated Ti—O molecules on the surface of $TiO_2$ nanoparticles. Two different ratios of DNA:nanoparticle were used; 2:1 for nanoconjugates with low oligonucleotide loading and 10:1 for nanoconjugates with high oligonucleotide loading. Thirdly, solutions containing complementary-sequence nanoconjugates $TiO_2$-T2 and $TiO_2$-T5 were mixed in equal volumes and nanoconjugates were annealed to each other, since T2 and T5 are complementary oligonucleotides and form dsDNA. When high loading of DNA per nanoparticle was used 3D network superstructures (predominant formula of these structures is [$TiO_2$-dsDNA-$]_n$) were formed through DNA base pairing interactions. When low DNA loading per nanoparticle was used, nanoconjugates assemble the $TiO_2$ nanoparticles into dumbbells (predominant formula of these structures is $TiO_2$-dsDNA-$TiO_2$) or three point rods. Theoretical length of 50 nucleotides long DNA molecule that is formed by hybridization of T2 and T5 oligonucleotides is about 17 nm.

Figure 27:
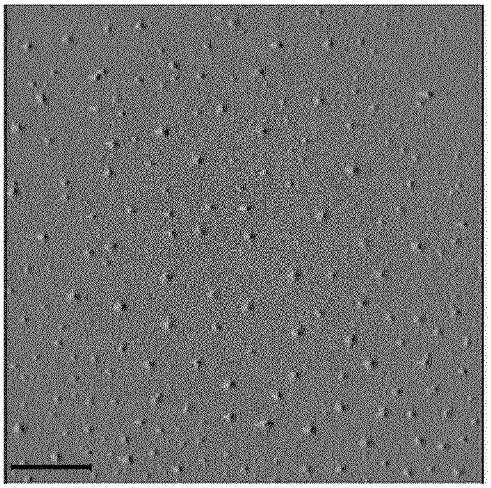
FIG. 27. AFM topographical image of $TiO_2$-ssDNA (prepared with T2 ssDNA oligonucleotide) nanoconjugates.
Figure 28:
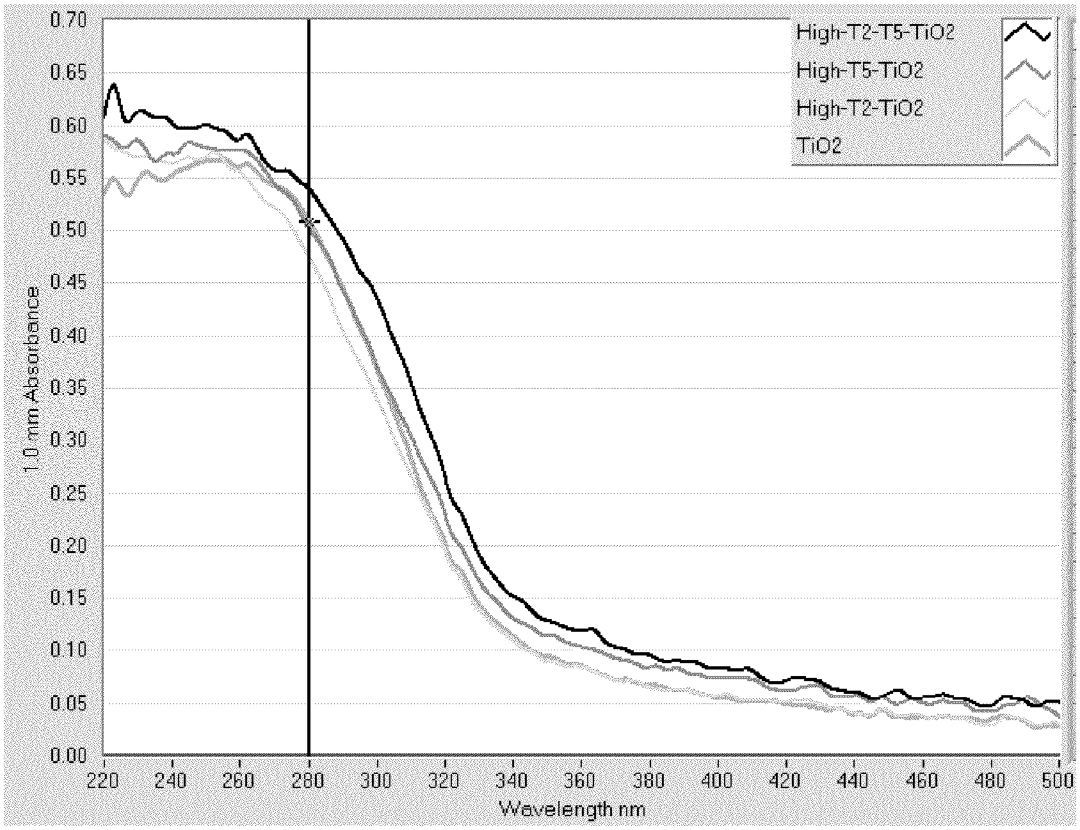
FIG. 28. UV-vis spectra of nanoparticles, nanocomposites and nanocomposite assembly.

Nanoparticles and nanoconjugates that do not form mismatch structures do not aggregate as shown by AFM analysis (FIG. 27) and the UV-vis spectra absorbance (FIG. 28). In FIG. 27, a large area of mica shows well dispersed nanoconjugates, with occasionally easily distinguishable attached DNA molecules. These were $TiO_2$-T2 ($TiO_2$-ssDNA) nanoconjugates with low DNA loading. The UV-visible spectra of $TiO_2$ nanoparticles, $TiO_2$-oligonucleotide nanoconjugates, and hybridized nanoconjugates superstructure [—$TiO_2$-dsDNA-$]_n$ are shown in FIG. 28. Free nanoparticle and one type of nanoconjugates ($TiO_2$-T2 oligonucleotide) showed almost identical UV-vis spectra. Another type of nanoconjugate ($TiO_2$-T5 oligonucleotide) showed a minor red shift, suggesting nanoparticle "aggregation" which is caused by the propensity of this $TiO_2$-ssDNA to form relatively stable mismatch dimmers (hence it forms low quantity of $TiO_2$-dsDNA-$TiO_2$). Finally, the nanoconjugate assembly formed after annealing of complementary nanoconjugates shows a much more obvious red shift caused by "aggregation" of nanoconjugates into an semi-ordered [—$TiO_2$-dsDNA-$]_n$ structure, where [—$TiO_2$-dsDNA-$]_n$ is formed through hybridization of fully complementary DNA oligonucleotides attached to the nanoparticles. It is well known that aggregation of nanoparticles/nanocrystals into quasi-two-dimensional or -three-dimensional superstructures causes a red shift of the absorbance peak because of an appearance of a longitudinal component in the spectra in the assembled nanoconjugates (Wang et al Nano Lett 2004, 4, 95-101; Cao et al J. Am. Chem. Soc. 2001, 123, 7961-7962). It was found that in these samples such "aggregation" depends on DNA oligonucleotide hybridization.

Figure 29:
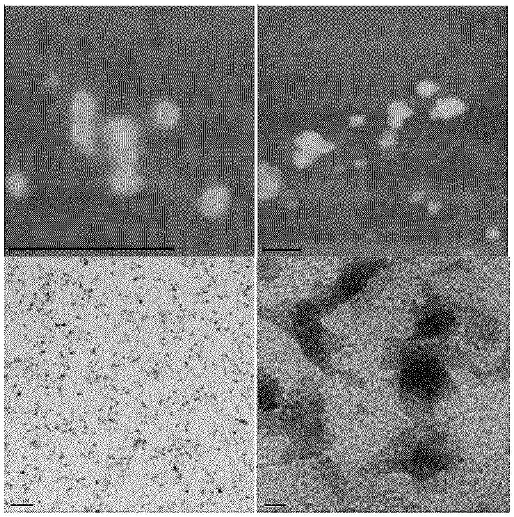
FIG. 29. Topographic AFM images (top row) of $TiO_2$-dsDNA-$TiO_2$ nanoconjugate 2D assemblies $TiO_2$-dsDNA-$TiO_2$ formed from nanoconjugates with low DNA loading (DNA:$TiO_2$=2:1). Scale bars for AFM images are 100 nm; and 200 and 10 nm for TEM images (left to right).
Figure 30:
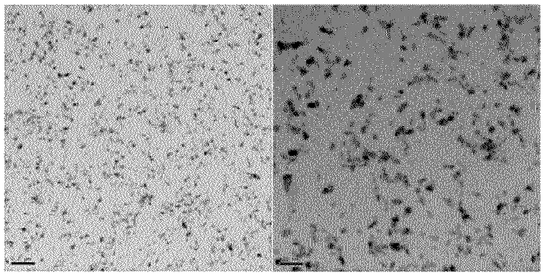
FIG. 30. TEM of $TiO_2$-dsDNA-$TiO_2$, 200 and 100 nm scale (Left to Right).

FIG. 29 shows the mini-assemblies made of nanoconjugates with low DNA loading. These structures are predominantly dumbbells or three point rods and their formula is best described as $TiO_2$-dsDNA-$TiO_2$. Images in FIG. 29 are two AFM topological images and two TEM images with lower and higher magnification. TEM samples were stained by uranyl acetate which stains DNA and lends it sufficient contrast to render it visible in TEM. Limited assembly sizes are visible in both AFM and TEM images and in the additional TEM images (FIG. 30). These assembles are formed through hybridization of DNA oligonucleotides; since there are only a few DNA molecules per each nanoparticle, these assemblies are limited in size.

Figure 31:
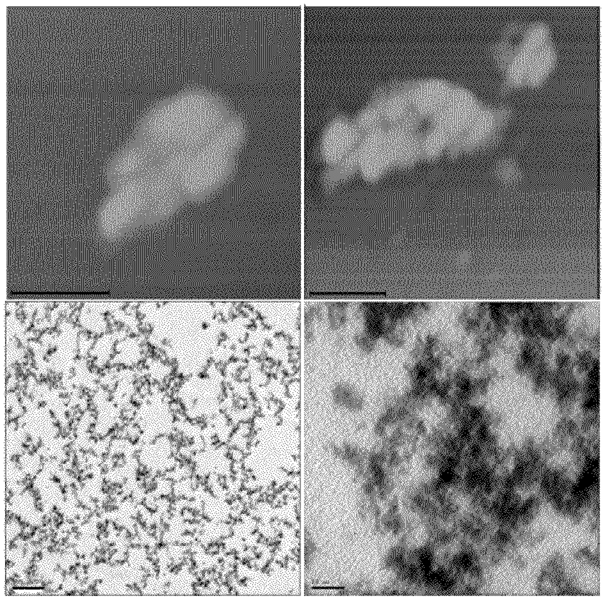
FIG. 31. AFM (top row) topographical images and TEM (bottom row) images of uranyl acetate stained nanoconjugate superstructures $[TiO_2\text{-dsDNA-}]_n$ formed by hybridization of nanoconjugates with high DNA loading (DNA:$TiO_2$=10:1).
Figure 32:
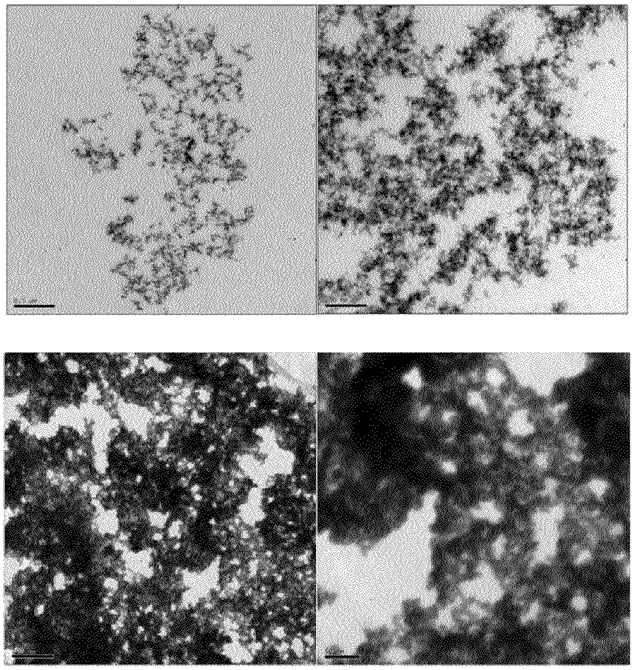
FIG. 32. Top row, TEM of —[$TiO_2$-dsDNA]- in agarose, scale bar: 500 nm (Left) and 100 nm (Right). Bottom row, TEM of —[$TiO_2$-dsDNA]- without agarose, scale bar: 200 nm (Left) and 50 nm (Right).

In FIG. 31, two topologic AFM images and two TEM images with lower and higher magnification show the complexes composed of $TiO_2$ nanoconjugates with high DNA loading (~10 DNA molecules per each $TiO_2$ nanoparticle). Because these nanoconjugates have high oligonucleotide loading each nanoparticle formed many hybridization connections with many other nanoconjugates, thus assembling into a large-scale $TiO_2$ nanoconjugate superstructure, a 3D network which can best be explained by the formula $[TiO_2$-dsDNA-$]_n$. In the TEM images samples were "frozen" in agarose and subsequently dehydrated and embedded in resin in such a way as to preserve the structure of the nanoconjugate network in 3D. This approach was borrowed from the cell embedding procedures for TEM which help preserve the 3D subcellular structures during dehydration and embedding. DNA of the nanoconjugates was stained by uranyl acetate during preparation of TEM samples, and is now visible as the lighter gray fronds of material, while nanoparticles look spherical. In AFM images, such assemblies appear as large nanoparticle aggregates, very different than the nanoconjugates not assembled into networks by hybridization (FIG. 27). Additional TEM images of this type of large nanoconjugate network are shown in FIG. 32 (both with resin embedding and sectioning and with drying of the network without embedding).

The PCNA coding sequence was cloned into a protein expression plasmid that functions in eukaryotic cells. This created a recombinant protein sequence that could be expressed in eukaryotic cells. Therefore this enabled firstly to prove correct DNA binding behavior of this recombinant PCNA protein; and secondly, to isolate the recombinant protein in order to use it in vitro for loading onto nanoconjugate dsDNA.

Figure 33:
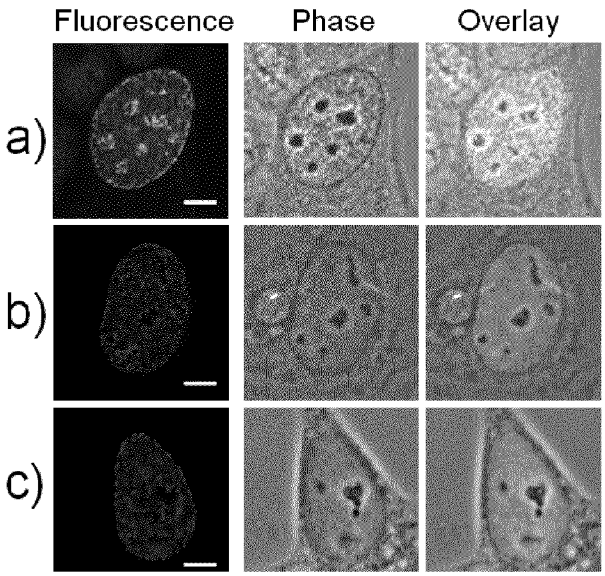
FIG. 33. Confocal fluorescence imaging of individual MCF7/W8 cells stained with antibodies for native proliferating cell nuclear antigen (PCNA) and two different recombinant PCNA proteins. (a) Native PCNA protein pattern showing early middle S phase PCNA staining pattern; (b) Recombinant PCNA protein extended at C terminus shows middle S phase PCNA staining pattern; (c) Recombinant PCNA protein extended at N terminus, shows middle S phase PCNA staining pattern. Scale bar is 5 μm.
Figure 34:
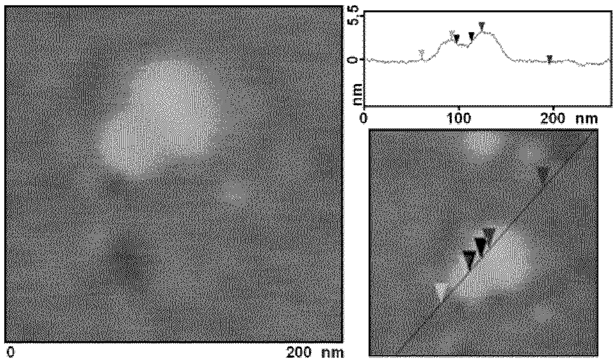
FIG. 34. Topographic AFM image (and accompanying height graph) of a $TiO_2$-dsDNA nanoconjugate loaded with a trimer of recombinant PCNA, assembled on the nanoconjugate according to the procedure of Tom et al (J. Biol. Chem. 2000, 275, 10498-10505).

The protein PCNA is distributed in a diffuse pattern in the nuclei of cells in G1 stage of the cell cycle, while its distribution during the synthesis (S) phase of the cell cycle is punctuate. Specifically, in mid-S phase of the cell cycle PCNA distribution (in addition to remaining punctuate throughout the nucleus) becomes perinuclear and perinucleolar. This mid-S phase PCNA distribution is the defining mark of cells at this stage of DNA synthesis (Celis et al PNAS 1985, 82, 3262-3266). Both of the recombinant PCNA proteins that were cloned showed this pattern of intracellular distribution (FIG. 33). Recombinant PCNA was found (i) in the nucleus only, with no protein in the cytoplasm; (ii) showing punctuate (not diffuse) mid-S phase perinuclear and perinucleolar pattern, which demonstrates that the mutant protein follows the distribution pattern of the wild type/endogenous PCNA protein. This signifies that the recombinant PCNA is both translocated from the cytoplasm to the nucleus and loaded onto DNA inside the nucleus (punctuate pattern) just as the native protein. Overexpressed proteins very often completely fill the nucleus and cytoplasm of the cell in a diffuse manner, making comparisons between distributions of mutants and endogenous proteins impossible. The fact that these recombinant PCNA proteins display the characteristic perinuclear and perinucleolar distributions associated with middle synthesis phase (rather than that completely filling the entire nucleus and cytoplasm of the cell) attests to their functionality. As a next step, monomeric PCNA proteins were assembled into trimers on dsDNA of $TiO_2$-dsDNA nanoconjugates and imaged the nanoconjugate-PCNA trimer complexes by AFM (FIG. 34). PCNA protein loading onto DNA was done under experimental conditions used by others to load and arrest the PCNA protein trimers on fork shaped DNA oligonucleotides (Tom et al J. Biol. Chem. 2000, 275, 10498-10505). Under experimental conditions established by Tom et al (Tom et al J. Biol. Chem. 2000, 275, 10498-10505) and used in this experiment, PCNA trimers cannot traverse triple DNA helix (about 3 nm width); likewise they are unable to pass over the nanoparticle (5-10 nm), and tethering of nanoparticles to DNA prevented PCNA trimers from slipping off the DNA. Sample of $TiO_2$-dsDNA-$PCNA_3$ was applied onto mica, extensively washed and imaged by AFM. AFM was performed in air, and dry PCNA trimers (70 kD ring around DNA) on dsDNA on the nanoconjugate appeared about 2.5 nm high. Therefore, dsDNA associated with nanoparticles presents an acceptable substrate for DNA binding proteins.

Example 6

Tunable Photodynamic Cleavage of Target DNA Using Modified Alizarin Red S-Peptide Nucleic Acid-$TiO_2$ Nanoconjugates Nucleic acid-nanoparticle nanoconjugates have been intensely studied over the past decade for their unique properties and benefits in biomedical diagnostics, imaging, and therapy (Mirkin et al Nature 1996, 382, 607-306; Endres et al J. Am. Chem. Soc. 2007, 129, 15760-15761). Typically consisting of 2-100 nm-sized nanoparticles with multiple single-strand nucleic acids covalently conjugated to the nanoparticle surface, these nanoconjugates hybridize to target DNA with higher affinity than their naked nucleic acid counterparts and are able to invade otherwise inaccessible mixed-base supercoiled dsDNA targets with a high level of sequence specificity (Jin et al J. Am. Chem. Soc. 2003, 125, 1643-1654; Lytton-Jean et al J. Am. Chem. Soc. 2005, 127, 12754-12755; Brown et al Anal. Biochem. 2008, 383, 226-235). These characteristics make nanoconjugates an ideal tool in cancer research for imaging and therapy of specific gene targets (Thurn et al Nanoscale Res. Lett. 2007, DOI 10.1007/s 11671-007-9081-5). The ability to create core-shell nanoparticles and conjugate multiple different ligands to the nanoparticle surface allows for nanoconjugates to serve as multi-modal imaging agents (Endres et al J. Am. Chem. Soc. 2007, 129, 15760-15761; Devaraj et al Bioconjug. Chem. 2009, Devaraj et al Bioconjug. Chem. 2009, 20, 397-401; Example 4 presented herein; Paunesku et al Nanomed. 2008, 4, 201-207), and the tunable physical characteristics of the nanoparticle permits various manners of therapeutic delivery in cancer treatment (Lal et al Ac. Chem. Res. 2008, 41, 1842-1851; Schneider et al Nano Lett. 2009 DOI: 10.1021/nl802990w. This example characterizes the mechanisms of a rationally designed peptide-nucleic acid (PNA)-$TiO_2$ nanoconjugate functionalized with a photosensitive dye to multiplex as both an imaging agent and therapeutic device for detection and removal of a specified DNA sequence.

Six nm $TiO_2$ nanoparticles were prepared and either left uncoated or coated with the fluorescent dye alizarin red s as described in Examples 4 and 5 presented supra. Alizarin red s is a photosensitive dye that releases reactive oxygen species upon excitation by light (Liu et al J. Mol. Catalysis. A: Chem.

2000, 153, 221-229), and this molecule can also conjugate to the surface of $TiO_2$ nanoparticles less than 20 nm, creating a red shift in light absorbance and allowing intracellular (Example 4) and in vitro (Brown et al Anal. Biochem. 2008, 383, 226-235) tracking of the nanoparticle through fluorescence. It is well established that reactive oxygen species can cause DNA damage in vitro (Ashikaga et al Mutat. Res. 2000, 466, 1-7; Arsac et al J. Oleo Sci. 2007, 56, 595-601; Sugden et al Toxicol. In Vitro 2004, 18, 741-748), in situ (Sparrow et al Invest. Opthalmol. Vis. Sci. 2002, 43, 1222-1227), and in vivo (Sugden Biotech. Histochem. 2004, 79, 71-90).

Figure 35:
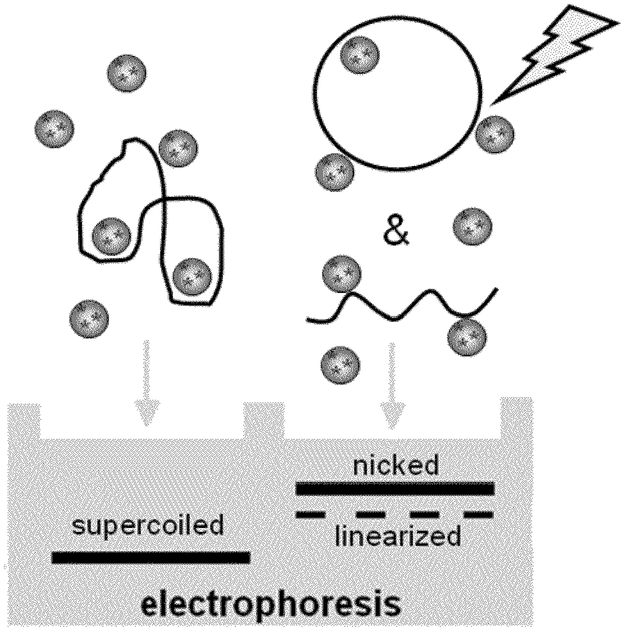
FIG. 35. Assay for detecting cleavage of plasmid DNA induced by excited alizarin red s-coated $TiO_2$ nanoconjugates (1.25% agarose gel with GelStar).
Figure 36:
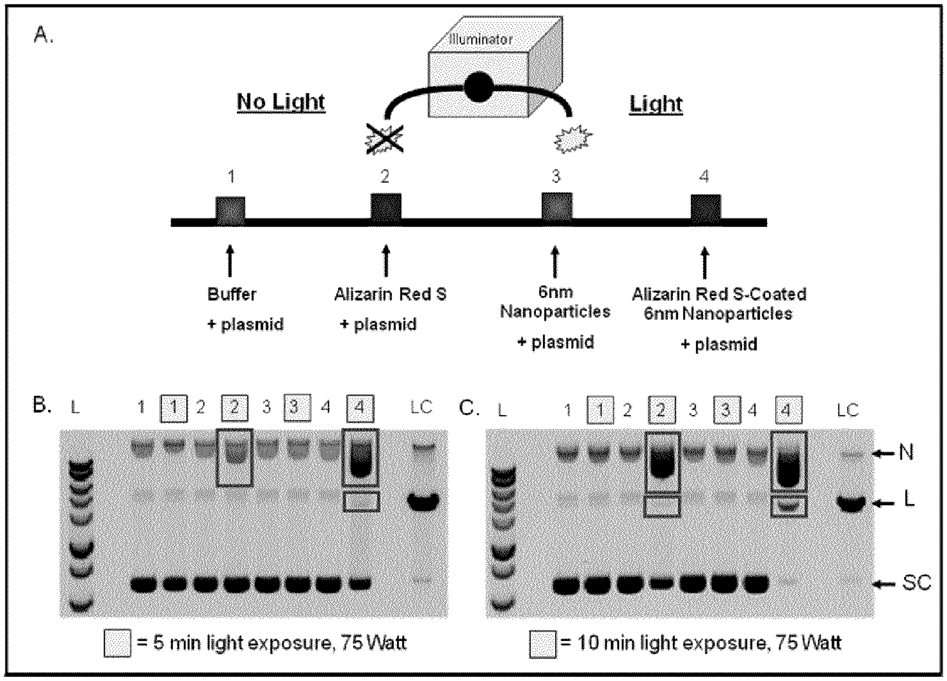
FIG. 36. Assay as shown in FIG. 35. A) Samples exposed to either no light or light. B-C) Excitation of the alizarin red s-coated $TiO_2$ nanoparticles results in increased plasmid cleavage.
Figure 37:
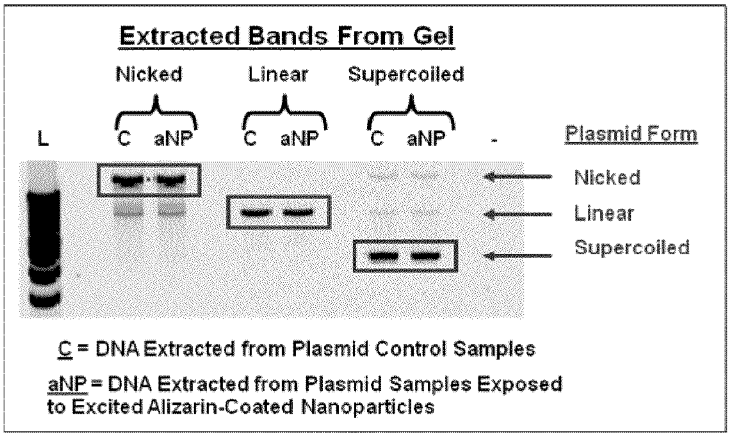
FIG. 37. Assays as shown in FIG. 35. E) Gel extraction and electrophoresis confirms plasmid configurations. SC=supercoiled, N=nicked, L=linearized, LC=enzyme digested linear control.

To determine the effect that conjugating alizarin red s to the nanoparticle surface has on DNA scission, a standard molecular biology technique (gel electrophoresis) was utilized to distinguish plasmid DNA that was either supercoiled (undamaged), nicked (possessing a single strand break), or linearized (possessing a double strand break) based upon differences in mobility rates (Arsac et al J. Oleo. Sci. 2007, 56, 595-601; Sugden et al Toxicol. In Vitro 2004, 18, 741-748) (FIG. 35). Reactions containing plasmid DNA and either buffer, alizarin red s, $TiO_2$ nanoparticles, or alizarin red s-coated $TiO_2$ nanoparticles were incubated at 37° C. for 10 minutes and either kept in the dark or illuminated with a 75 watt halogen bulb for 5-10 minutes (FIG. 36). Samples were then run via electrophoresis at 50 volts for 4 hours on a 1.25% agarose gel and scanned on a Typhoon Trio multi-mode imager to visualize the different resulting configurations of plasmid DNA (FIG. 36). In samples containing buffer or $TiO_2$ nanoparticles, electrophoresis revealed that plasmid DNA was primarily in the supercoiled form, with smaller portions found in various nicked configurations, and light did not have an effect on this ratio (FIG. 36B, lanes 1 and 3). In samples containing the photosensitive dye alizarin red s, light exposure resulted in an increase in the presence of nicked plasmid, indicating accumulation of single strand breaks in the plasmid DNA (FIG. 36B, lane 2). However, when samples contained alizarin red s-coated nanoparticles, light excitation resulted in a dramatically higher increase in nicked plasmid DNA and the appearance of linearized plasmid DNA where double stranded breaks had occurred (FIG. 36B, lane 4). The quantity of nicked and linearized plasmid obtained was depended upon the time of light exposure (FIG. 36C). To confirm the identities of plasmid configurations resulting from excitation of alizarin red s-coated $TiO_2$ nanoparticles, supercoiled, nicked, and linearized plasmid DNA bands were excised and purified from the agarose gel. The purified DNA was then rerun via electrophoresis and compared to undigested and enzyme digested controls to confirm the configurations (FIG. 37). Although a small amount of plasmid degradation occurred through the process of excising and purifying the DNA (supercoiled lanes), the results confirmed the configurations of nicked and linearized plasmid DNA products resulting from excitation of alizarin red s-coated $TiO_2$ nanoparticles (nicked and linear lanes). Additionally, the reappearance of the double "phantom" band (running just above the linearized fragment) in only the nicked samples of this experiment verified that this product was indeed a subtype of nicked configuration (nicked lanes).

Figure 38:
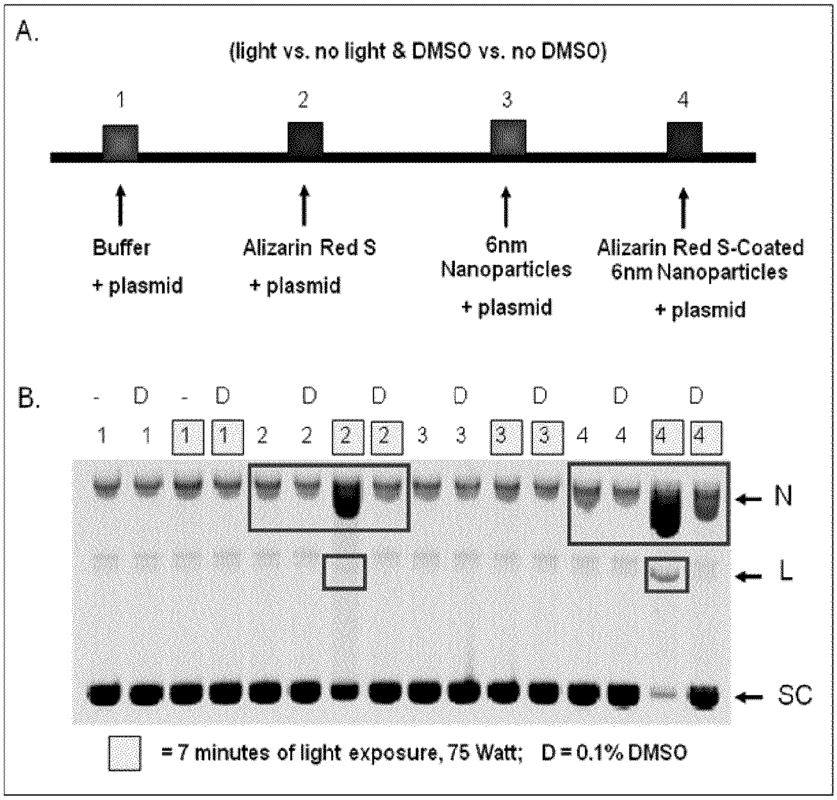
FIG. 38. A) Samples exposed to either no light or light and no DMSO or DMSO. B)

To determine the mechanism of plasmid DNA cleavage resulting from excitation of alizarin red s and alizarin red s-coated $TiO_2$ nanoparticles, the same types of samples were illuminated either in the presence or absence of the reactive oxygen species scavenger, DMSO (Ashikaga et al Mutat. Res. 2000, 466, 1-7) (FIG. 38). No increase in nicked or linearized plasmid was observed upon excitation when samples contained either buffer or $TiO_2$ nanoparticles and the presence of DMSO did not alter this finding (FIG. 38B, lane 1 and 3). As before, the presence alizarin red s in samples exposed to light resulted in an increase in both nicked and linearized plasmid and the presence of alizarin red s-coated $TiO_2$ nanoparticles greatly accentuated this effect (FIG. 38B, lanes 2 and 4). In both of these cases, the addition of DMSO curbed DNA damage resulting from light exposure, indicating DNA damage by production of reactive oxygen species (FIG. 38B, lanes 2 and 4 marked D).

This increase in DNA damage resulting from excited alizarin red s-coated nanoparticles is likely due to many factors, including a red shift in absorbance of the nanoconjugate (compared to its components) (Example 4) as well as interaction between the nanoconjugate and plasmid DNA. It has been established that $TiO_2$ has an affinity for polyphosphates (Michelmore et al Phys. Chem. Chemical Phys. 2000, 2, 2985-2992). The role of the latter was investigated by expanding upon previous experiments and using $TiO_2$ nanoparticles that were coated with glycidyl isopropyl ether (GIE), which reduces interaction between the nanoparticle surface and its surrounding environment (Paunesku et al Nat. Mater. 2003, 2, 343-346; Rajh et al Nano Lett. 2004, 4, 1017-1023). Plasmid samples containing either GIE, GIE and alizarin red s, or GIE-alizarin red s-coated $TiO_2$ nanoparticles were illuminated for 5 minutes with 150W halogen bulb (FIG. 39). Three independent replicate experiments demonstrated that plasmid DNA exposed to light was not cleaved in the presence of GIE alone, but was cleaved when alizarin red s was added to the GIE-containing solution (FIG. 39B, lanes 1 and 2). This finding supported previous findings and indicated that the addition of GIE did not act as a notable scavenger of reactive oxygen species. Conversely, when the illuminated plasmid solution contained GIE-alizarin red s-coated $TiO_2$ nanoparticles, no notable plasmid cleavage was observed (FIG. 39B, lane 3). Comparing these results with previous observations (where excitation of alizarin red s-coated nanoparticles that were not coated with GIE yielded significantly more plasmid cleavage than alizarin red s alone) supports the literature findings that additional coating of the nanoparticle surface with GIE reduces interaction between the $TiO_2$ nanoparticle and the polyphosphate backbone of DNA. The fact that reactive oxygen species only exist for less than 100 ns and can only travel short distances in solution or cells (2-100 nm) (Hall Chapter 1-Physics and Chemistry of Radiation Absorption, in Radiobiology for the Radiologist Lippincott Wilkins & Williams: Philadelphia, Pa., USA, 2006, 5-15; Niedre et al Photochem. Photobiol. 2002, 75, 382-391; Moan Photochem. Photobiol. 1990, 6, 343-347) further supports this interpretation and demonstrates that DNA cleavage resulting from excitation of alizarin red s-coated $TiO_2$ nanoparticles is tunable, due to production of reactive oxygen species, and dependent upon close spatial proximity between the nanoparticle to its DNA target.

Previous studies have shown that DNA-$TiO_2$ nanoconjugates can hybridize with complementary DNA in a sequence-specific manner and consequently be retained in sub-cellular compartments dependent upon the nucleic acid sequence of the nanoconjugate (Paunesku et al Nat. Mater. 2003, 2, 343-346; Paunesku et al Nano Lett. 207, 7, 596-601; Paunesku et al Nanomed. 2008, 4, 201-207; Example 4 herein). Peptide nucleic acids as a class of DNA analog (Nielsen et al Science 1991, 254, 1497-1500) that possess many advantages in hybridization abilities over traditional DNAs (Armitage et al Nucl. Acids Res. 1997, 25, 4674-4678; Betts et al Science 1995, 270, 1838-1841; Brown et al Science 1994, 265, 777-780; Demidov et al Biochem. Pharmacol. 1994, 48, 1310-1313; Eriksson et al Nat. Struct. Biol. 1996, 3, 410-413; Hamliton et al Med. Chem. Lett. 1996, 6, 2897-2900;

Kaihatsu et al Chem. Biol. 11, 749-758; Kaihatsu et al Biochem. 2003, 42, 13996-14003; Rasmussen et al Nat. Struct. Biol. 1997, 4, 98-101; Smolina et al Nucl. Acids Res. 2005, 33, e146; Summerton et al in Peptide Nucleic Acids, Morpholinos, and Related Antisense Biomlecules, During, C. G. J. A. M. K., Ed. Springer US, 2006). The ability of alizarin red s-coated PNA-$TiO_2$ nanoconjugates to hybridize in a sequence-specific manner to a mixed-base target within supercoiled plasmid DNA was previously characterized (Brown et al Anal. Biochem. 2008, 383, 226-235), and this system may be manipulated in biomedical imaging and therapy of target DNA sequences. If the reduction in cleavage product observed when using GIE-coated nanoparticles is due to lower interaction between the nanoparticle and phosphate backbone as proposed, then conjugating PNAs to the nanoparticle surface may restore interaction between the plasmid and the nanoparticle in a sequence-specific manner, as indicated by a return of cleavage product. The effect of conjugating different peptide nucleic acid sequences to GIE-alizarin-coated $TiO_2$ nanoparticles on DNA cleavage was investigated (FIG. 40A). The results of this experiment confirmed the previous findings that upon excitation by white light, plasmid DNA strand scission occurs in samples containing alizarin red s and GIE, but not in alizarin red s and GIE-coated $TiO_2$ nanoparticles (FIG. 40B, lanes 1-3). On the other hand, plasmid scission can be recovered when PNAs are additionally conjugated to the surface of GIE-alizarin red s-coated $TiO_2$ nanoparticles (forming nanoconjugates). Excitation of nanoconjugates containing the R18 PNA sequence (specific for the inserted plasmid target) resulted in significantly increased nicked plasmid cleavage than either the TIS (30%) or 5'LINE (14%) PNA nanoconjugates (FIG. 40B, lanes 4-6 and FIG. 41). The present invention is not limited to a particular mechanism. Indeed, an understanding of the mechanism is not necessary to practice the present invention. Nonetheless, it is contemplated that analyses of the plasmid sequence indicates that the lower quantity cleavage products observed in samples containing either TIS or 5'LINE nanoconjugates may be due to shorter stretches of base matches and partial mismatches residing within alternative regions of the plasmid DNA (FIGS. 42-44). Hybridization between PNA-$TiO_2$ nanocojugates and DNA sequences can form stable complexes at room temperature with matches of little as 7 bases (Liu et al Pros. of SPIE 2006, 6096, 1-10). As in the case of alizarin red s-coated $TiO_2$ nanoparticles, the mechanism of plasmid cleavage for excited GIE-alizarin red s-coated PNA-$TiO_2$ nanoconjugates was also production of reactive oxygen species as indicated by reduction in plasmid cleavage in samples containing the scavenger DMSO (FIG. 45)

To further assess the specificity of cleavage products resulting from excitation of GIE-alizarin red s-coated PNA-$TiO_2$ nanoconjugates, linearized DNA cleavage fragments were excised from the agarose gel, extracted, and then digested with the restriction enzyme FspI, possessing a single restriction site on the opposite side of the plasmid from the inserted target (FIG. 46). After enzyme digestion and inactivation, the DNA fragments were rerun on an agarose gel, imaged, and analyzed. Although complete plasmid digestion was obtained in the controls, plasmid samples that had been linearized by excitation of PNA-$TiO_2$ nanoconjugates experienced incomplete digestion, likely due to some generalized DNA degradation post excitation (FIG. 47). Nevertheless, two more prominent linear fragments were recovered in all samples that had been exposed to the excited GIE-alizarin red s-coated PNA-$TiO_2$ nanoconjugates, and these fragments matched the sizes predicted by a double enzyme control digest using FspI and XhoI (the later restriction enzyme site being located just downstream of the insert and serving as a control for sequence-specific nanoconjugate induced cleavage) (FIG. 47). The highest quantity of the two predicted linear fragments was recovered in the case of the samples that had been exposed to the excited PNA(R18)-$TiO_2$ nanoconjugate (FIG. 47). Comparisons between replicate experiments indicated that this 15% increase in cleavage in the case of the R18 sequence was significantly higher than either the 5'LINE or TIS sequence (FIG. 47) which supported earlier results.

This work has investigated the manner in which photoreactive dyes (used for nanoparticle imaging) can be used in a multifunctional manner to also convey therapeutic capabilities by enabling enhanced, activate able scission of DNA that is tunable for sequence-specificity through application appropriate of nanoparticle surface coatings and rationally designed nucleic acids. The effect of coating $TiO_2$ nanoparticles with the fluorescent dye alizarin red s has been examined, and thereby it has been demonstrated that, upon photoactivation, such coating leads to enhanced cleavage of plasmid DNA through production of reactive oxygen species. This enhanced DNA cleavage is due to both a red shift in light absorbance of the nanoconjugate compared to its components and interaction between the nanoparticle and DNA phosphate backbone. This non-specific interaction between the $TiO_2$ nanoparticle and DNA can be relieved by coating the nanoparticles with GIE and then restored in a sequence-specific manner through conjugation of PNAs to the nanoparticle surface. Upon activation by light, these GIE-alizarin red s-coated PNA-$TiO_2$ nanoconjugates can enhance sequence-specific cleavage of the plasmid DNA. These results show that how nucleic acid-nanoparticle nanoconjugates can be used to not only for imaging of deleterious DNA sequences but also for therapeutic cleavage purposes. This finding highlights the extraordinary multifunctional abilities that nanomaterials offer to diverse biomedical applications.

Example 7

Gadolinium-Conjugated $TiO_2$-DNA Oligonucleotide Nanoconjugates Show Prolonged Intracellular Retention Period and T1-Weighted Contrast Enhancement in Magnetic Resonance Images A. Experimental (1) Synthesis of Contrast Agent The first step of the synthesis process was synthesis of poly(1-glutamic acid) (PGA; $M_n$=69.1 kDa, $M_w$=80.8 kDa) using the procedure described by Idelson and Blout (Idelson et al Polypeptides 1958, 80, 2387-2393). Poly(1-glutamic acid) N-hydroxysuccinimide esters (PGA-OSu) (compound 1, FIG. 48) and 1,4,7,10-tetraazacyclododecane-1,4,7-tris (acetic acid)-10-(acetic acid-1,6-hexanediamine monoamide (compound 2, FIG. 48) were prepared according to the literature (Ke et al Mag. Reson. Imaging 2006, 24, 931-940). The other reagents were purchased from Sigma-Aldrich (St. Louis, Mo.). Spectra/Por 6 membrane (molecular weight cut-off 25,000) was purchased from Spectrum Laboratory, Inc. (Rancho Dominguez, Calif.).

The molecular weights of the polymers were determined by size exclusion chromatography with poly((N-2-hydroxypropyl)methacrylamide) calibration on an AKTA fast protein liquid chromatography system with a Superose 6 column (GE Healthcare, Piscataway, N.J.), ultraviolet, and refractive index detectors. The Gd wt % content in the copolymers was determined by inductively coupled plasma-optical emission spectroscopy (Optima 3100XL; Perkin-Elmer, Norwalk, Conn.). The content of dopamine in the conjugate was determined by ultraviolet spectroscopy.

PGA-1,6-hexanediamine-(Gd-DOTA)-dopamine conjugate (Zhu et al J. Nanosci. Nanotech. 2006, 6, 996-1003) was prepared according to FIG. 48. Briefly, PGA-OSu (compound 1, 80 mg), 1,4,7,10-tetraazacyclododecane-1,4,7-tris (acetic acid)-10-(acetic acid-1,6-hexanediamine monoamide) (compound 2, 373 mg, 0.34 mmol), dopamine (compound 3, 5.0 mg, 0.036 mmol), p-(dimethylamino)pyridine (55 mg, 0.45 mmol), and 2.0 mL triethylamine were added sequentially into 15 mL anhydrous dimethylformamide (DMF) with stirring. The mixture was stirred overnight at room temperature (18-26° C.), and the solvent was then evaporated under vacuum. The product was precipitated from acetone. The precipitate was then dissolved in deionized water, and the pH of the solution was adjusted to 5 to 6. An excess of $(CH_3CO_2)_3$ Gd (200 mg) was added to the solution, and the mixture was stirred overnight at room temperature. Xylenol Orange indicator was added into the solution, and EDTA was then added until the pink color disappeared. The polymer conjugate was purified by dialysis with Spectra/Por 6 membrane (MW cutoff 25,000; Spectrum Laboratory, Inc., Rancho Dominigues, Calif.). The solution was lyophilized to a pink product, which was dissolved in distilled water again and treated with sodium dithionite. After dialysis and lyophilization, a colorless final product was obtained. The yield was 67 mg. The molecular weight of the conjugate is 50.9 kDa (PDI, polydispersity distribution index=1.17). Based on weight content (9% for Gd, 2.7% for dopamine), each molecule of contrast agent contains 28 molecules of gadolinium and 10 molecules of dopamine. Because of the rigidity and bulk of the contrast agent molecule, it is anticipated that steric hindrance will make it unlikely that more than one dopamine per molecule of contrast agent establishes interactions with the $TiO_2$ nanoparticle surface.

(2) Synthesis of Nanoparticles and Nanoconjugates $TiO_2$ nanoparticles were prepared by a modification of a procedure published by Rajh and others (Paunesku et al Nat. Mater. 2003, 2, 343-346; Paunesku et al Nano Lett. 2007, 7, 596-601; Rajh et al J. Phys. Chem. B 2002, 106, 10643-10552). For the experiments described here, 0.8 μM ($TiO_2$) 6-nm nanoparticles were used. The concentration of the nanoparticles was determined by inductively coupled plasma-mass spectroscopy (ICP-MS). The size, dispersal, and uniformity of nanoparticles were examined by atomic force microscopy and transmission electron microscopy.

Uncoated $TiO_2$ nanoparticles were mixed with DNA oligonucleotides (synthesized with glycerol on the 3' end of the molecule) in the ratio of $TiO_2$ to oligonucleotide equal to 1:7 (corresponding to approximately a 1:0.01 ratio if the number of active nanoparticle surface sites is considered). The oligonucleotide sequence was matching the sense strand of the R18S ribosomal RNA gene: 5' ttccttggatgtggt-glycerol 3' (R18Ss) (SEQ ID NO:8) universally present in mammalian cells (Paunesku et al Nano Lett. 2007, 7, 596-601). Hydroxyl (—OH) groups of glycerol bound loosely to the surface of the nanoparticles, similarly to the —OH groups of phosphates (Michelmore et al Phys. Chem. Chem. Phys. 2000, 2, 2985-2992). Such nanoconjugates were mixed with Gd contrast agent in a 1:69 molar ratio (for an active surface sites ratio of 1:0.1). Because each contrast agent molecule contained more than one Gd atom, with this stoichiometry it was expected that the final molar ratio of $TiO_2$ to Gd could be as high as 1932:1. Using ICP-MS, however, the actual ratio was found to be maximally 630:1. This may be a result of steric hindrance between contrast agent molecules as they compete for binding sites on the $TiO_2$ nanoparticle surface. Conjugation between the dopamine-Gd contrast agent molecule and $TiO_2$ was immediate, and the color of nanoparticle conjugates upon binding changed from transparent whitish to ochre; this was expected, because binding all active surface sites of $TiO_2$ with dopamine causes a color change to deep brown (Rajh et al J. Phys. Chem. B 2002, 106, 10543-10552). Completed nanoconjugates were dialyzed in 10 mM sodium phosphate, purified and concentrated by centrifugation to 4 μM $TiO_2$-DNA-Gd and stored at 4° C.

(3) Cell Culture and Nanoconjugate Transfections

For transfection experiments MCF-7/W8/WS8 breast cancer cells (American Type Culture Collection, ATCC, Manassas, Va.) and PC3-M prostate cancer cells (ATCC) were grown in a 5% $CO_2$ humidified atmosphere in RPMI1640 cell culture medium (this and all other standard cell culture supplements were from Invitrogen/Gibco, Carlsbad, Calif.) supplemented with 10% fetal bovine serum and antibiotic-antimycotic. MCF-7/WS8 medium also contained insulin at a concentration of 10 μg/mL (Sigma, St. Louis, Mo.), 200 mM 1-glutamine, and 10 mM nonessential amino acids; PC3-M medium also contained 25 μg/mL G418 and 2.4 mg/mL HEPES. Nearly confluent cells were serum-starved for 16 to 20 hours before transfection or treatment.

For SuperFect transfection, 60 μL of SuperFect reagent (Qiagen, Valencia, Calif.) and 300 μL of any one of the following: (1) Gd contrast agent, (2) $TiO_2$ nanoparticles, or (3) $TiO_2$-DNA-Gd nanoconjugates were used; these mixtures were applied onto 16 million cells each. Final concentrations of these agents in the medium were (1) 144 μM Gd; (2) 0.12 μM $TiO_2$ nanoparticles, or (3) $TiO_2$-DNA-Gd nanoconjugates wherein $TiO_2$ nanoparticles were 0.12 μM and Gd was 75.6 μM in concentration. Media were exchanged for fresh complete cell media 24 hours later and, after an additional 24-hour incubation, cells were harvested for imaging.

For transfection by electroporation, cells were collected by trypsinization (0.05% trypsin, Invitrogen/Gibco) and resuspended in MZB solution (Tritech, Carlsbad, Calif.). For each electroporation, a mixture of $10^6$ cells and 5 μL of nanoconjugate each was electroporated using the Mammozapper apparatus (Tritech), following the manufacturer's instructions. The cells were placed in complete medium and allowed to grow for 24 hours before harvesting.

In all cases, cells harvested for MRI were embedded in 300 μL agarose phantoms. Once the MRI was completed, these phantoms were used for ICP-MS and/or preparation of paraffin-embedded samples for sectioning and imaging by x-ray fluorescence microscopy.

(4) Magnetic Resonance Imaging

To prepare samples for MRI, 150 μL of Hank's balanced buffered salt solution (HBBS; Invitrogen/Gibco) containing cells were mixed with 2% agarose melted in 150 μL of HBBS. Cells in agarose solidified as a plug and were transferred into tubes, placed in a water bath, and imaged using a 1.5 T Siemens Sonata system (Erlangen, Germany) with a four-channel head coil for signal reception and body coil for excitation. T 1 of each sample was measured using an inversion recovery sequence with repetition time ($T_R$)=4000 ms and inversion times of 50, 200, 500, 800, 1000, 1200, 1500, and 2000 ms. Other scan parameters were: field of view=125×200 $mm^2$; acquisition matrix=115×192; readout bandwidth=965 Hz/pixel; slice thickness=5 mm; all images were acquired in the coronal orientation.

For data analysis the raw data of signal intensity versus TI were fit to the equation: Signal intensity=abs(A*(1−2*exp(−R1*TI))+C, where R1=1/T1. Variables A and C are free parameters of the model. The confidence interval was determined statistically; R2 indicates goodness of fit. The TI corresponding to the lowest signal intensity ($TI_{null}$) is an indication of the T1 value; this relationship can be estimated by the equation: $T1=TI_{null}/\ln(2)$. T1 values determined using the results of the equation fit and the null point relationship are listed in Table 2. Signal intensity, a quantitative metric of relative brightness, was measured with a circular region-of-interest within each sample.

(5) X-Ray Fluorescence Imaging

Agarose phantoms with cells used for MRI were embedded in paraffin and sectioned. Five-micron-thick sections were placed on silicon nitride ($Si_3N_4$) windows (Silson, Northampton, United Kingdom). Kα characteristic x-ray fluorescence of elements between P and Zn and Lα shell characteristic x-ray fluorescence of Gd were mapped simultaneously in 2D using an ultra-LEGe energy dispersive detector (Can berra, Meriden, Conn.) (Paunesku et al Nat. Mater. 2003, 2, 343-346; Paunesku et al Nano Lett. 2007, 7, 596-601; Panesku et al J. Cell Biochem. 2006, 99, 1489-1502). The hard x-ray fluorescence microprobe (XFM) facility at the 2-ID-D beamline at the Advanced Photon Source in the Argonne National Laboratory (Argonne, Ill.) was used to focus hard x-rays with photon energy of 10 keV into a beam spot ~0.3×0.2 μm. The fluorescence spectra were acquired at every pixel of 2D raster scan. The spectra were fitted with modified Gaussians corresponding to x-ray fluorescence lines. Elemental quantification against NBS thin film standards 1832 and 1833 (NIST, Gaithersburg, Md.) and co-localization of elemental signals were investigated using MAPS program (Vogt et al J. Physique Iv. 2003, 104, 617-622).

B. Results

MRI measurements were performed with PC3-M or MCF-7 cells, 24 or 48 hours after treatment, respectively. These two different types of cells were either transfected by electroporation or chemically (SuperFect reagent) with complete nanoconjugate or its components. FIG. 49 shows a set of T1-weighted images acquired at an inversion time of 1000 ms. Signal enhancement was only observed in those samples that contained cells treated with $TiO_2$-DNA-Gd, whereas cell samples treated with $TiO_2$ or "free" Gd contrast agent showed no T1-weighted enhancement at this time. Results of signal intensity and T 1 measurements done on samples in FIG. 49 are shown in Table 2.

TABLE 2

T1 values of samples from FIG. 49, calculated using two different approaches

| Cell number | Treatment (transfection) | Null point method | Equation method | 95% CI* | R2*† | Signal intensity |
|---|---|---|---|---|---|---|
| $7 \times 10^6$ | $TiO_2$-DNA-Gd (electroporation) | 813 | 621 | ±50 | 0.9841 | 428 |
| $15 \times 10^6$ | | 759 | 615 | ±43 | 0.9887 | 405 |
| $5 \times 10^5$ | $TiO_2$-DNA-Gd (SuperFect) | 446 | 626 | ±84 | 0.9662 | 348 |
| $5 \times 10^6$ | | 205 | 351 | ±68 | 0.9973 | 766 |
| $5 \times 10^5$ | Gd (SuperFect) | 1436 | 1799 | ±28 | 0.9958 | 33 |
| $5 \times 10^6$ | | 1235 | 1625 | ±27 | 0.9938 | 71 |
| $5 \times 10^5$ | $TiO_2$ (SuperFect) | 1459 | 2210 | ±20 | 0.9977 | 30 |
| $5 \times 10^6$ | | 1309 | 1783 | ±40 | 0.9868 | 48 |
| $5 \times 10^5$ | Control | 1326 | 1608 | ±36 | 0.9924 | 49 |
| $5 \times 10^6$ | Control | 1245 | 1655 | ±40 | 0.986 | 46 |

*Equation method.

†R2 indicates goodness of fit.

The use of the SuperFect transfection procedure showed no differences in cell viability between cells treated with $TiO_2$ nanoparticles or $TiO_2$-DNA-Gd nanoconjugates. Nevertheless, SuperFect-mediated transfection with such high quantities of nanoparticles resulted in high cell mortality (between 50% and 75% in different experiments), and it was decided to improve cell viability by decreasing the nanoparticle quantity and performing the transfection by electroporation. Cell viability following electroporation was nearly 100%, and cells continued to grow in culture without any noticeable change in growth rate. Results demonstrate that the Gd conjugation did not change toxicity of nanoparticles.

Sections of agarose phantoms with embedded cells were analyzed by ICP-MS. If one considers that the volume of $5\times10^6$ cells is at most one twentieth of the volume of the phantom (considering cellular r=10 μm, phantom V of 300 μL), the intracellular concentration of Gd in cells treated with Gd contrast agent alone reaches an average of 0.75 μM, whereas intracellular concentration of Gd in cells treated with nanoconjugates reaches an average of 3940 μM. In terms of retention of the material present in the cell media during the first 24 hours of incubation, these numbers correspond to 0.75 μM/144 μM Gd or 0.5% Gd retention for the free contrast agent versus 3940 μM/75.6 μM or 500% Gd retention for the $TiO_2$-DNA-Gd nanoconjugate treatment. Therefore, at 48 hours after transfection, Gd in cells treated with nanoconjugates rather than the "free" Gd contrast agent achieved about 1000-fold higher Gd concentration. This is a combined outcome of increasing nanoconjugate retention by using a DNA oligonucleotide as a tether (Paunesku et al Nano Lett. 2007, 7, 596-601) and by concentrating Gd through its binding it to a nanoparticle (groups of up to 630 Gd atoms travel as a package attached to the nanoparticle).

FIG. 50 shows co-localization of Ti and Gd inside cells. XFM maps of two cells treated by $TiO_2$-DNA-Gd show the positions of nuclei by the regions of more intense P and Zn signals, corresponding to location of DNA and Zn finger nuclear transcription factors, respectively (Panesku et al J. Cell Biochem. 2006, 99, 1489-1502). Localization of Ti and Gd in these cells overlaps with P and Zn, indicating intranuclear nanoconjugate accumulation. The ratio of Ti/Gd in $\mu g/cm^2$ varying between 1:7 and 1:14 does not reflect well the molar ratio of Ti/Gd, considering that (1) the ratio ($TiO_2$)/Gd is 1:27 to 1:630, (2) each $TiO_2$ nanoparticle has 3320 Ti atoms, MW ~48 daltons, and (iii) Gd MW ~157 daltons. Based on these data, the expected weight ratio of Ti/Gd would be 37:1 to 37:23. This discrepancy between the expected and obtained Ti/Gd ratio can be explained by the fact that the calibration of XFM for elements that are detected by Lα fluorescence (such as Gd) and Kα fluorescence (such as Ti) may not be readily directly comparable.

Example 8

Doxorubicine—$TiO_2$ Shell Nanoparticles

Doxorubicin is a chemotherapeutic agent that has been the subject of much study due to its long-standing role as a widely accepted choice for cancer treatment. The most successful application of nanotechnology to doxorubicin delivery has been through the use of liposomal delivery systems that can be selectively degraded upon reaching their target. While these nanoscale developments have made improvements in reducing the associated cardiotoxicity of doxorubicin and common mechanisms of doxorubicin resistance, problems still remain, and many tumors are finding new ways to circumvent doxorubicin's cytotoxicity. This example describes the use of $TiO_2$-doxorubicin nanoconjugates for improved delivery of doxorubicin and characterizing the mechanism through which it enhances its cytotoxicity.

Doxorubicin

Doxorubicin (also called Adriamycin) is an anthracycline antibiotic used for its clinical effectiveness in the treatment of a variety of malignancies. Its discovery is owed to two groups of French and Italian researchers, who in the 1960's discovered that the soil-dwelling bacterium, Streptomyces peucetius produced a red pigment with anti-tumor properties. The pigment, daunorubicin, was found to be effective against acute lymphoblastic or myeloblastic leukemias (ALL, AML). Subsequent formulations to improve the efficacy of daunorubicin produced doxorubicin (FIG. 51), which has been found to be more effective against solid tumors, such as breast cancer, childhood solid tumors, lung tumors, sarcomas, and certain lymphomas. Both daunorubicin and doxorubicin are still widely used today for their cytotoxic properties against malignant cells and remain some of the most effective cancer treatments available.

The most significant drawback to doxorubicin and daunorubicin treatment is a fatal cardiotoxicity characterized by dilated cardiomyopathy and congestive heart failure. This toxicity is attributable to the cumulative dose of anthracyclines received, so it follows that finding methods of reducing the cumulative dose while maintaining the therapeutic efficacy has been studied extensively. Chemical modification of various functional groups present on doxorubicin and daunorubicin has been explored broadly, and to date on the order of 2000 variations exist. However, doxorubicin and daunorubicin remain as the standards for cancer treatment amongst anthracyclines.

The mechanism(s) by which doxorubicin exerts a cytotoxic effect are continually being elucidated. The present invention is not limited to a particular mechanism. Indeed, an understanding of the mechanism is not necessary to practice the present invention. Nonetheless, it is contemplated that concentration of drug in the serum plays a large factor in the manner in which doxorubicin mediates cell death. Doxorubicin itself passes through the phospholipids bilayer via simple diffusion. In the cytoplasm it binds with a proteasome, forming a complex which is delivered to the nucleus and enters the intranuclear milieu via an ATP-mediated nuclear pore mechanism. Once in the nucleus, doxorubicin intercalates into DNA and acts to block the action of topoisomerase II (topoII) by stabilizing an intermediate step. TopoII normally functions by cleaving both strands of DNA to allow passage of another DNA strand through, thus relieving mechanical stress and chromosome entanglement. It then re-ligates the strands together. Doxorubicin stabilizes the step in which both strands of DNA are cleaved, and topoII becomes unable to re-ligate the ends pieces. Apoptotic signaling ensues, resulting in activation of p53 and its downstream mediators, including p21, XRCC1, Bcl-2 (inactivation), and caspases. The gene expression signature of doxorubicin treatment in both doxorubicin-sensitive and -resistant cells lines has been examined via microarray, and a number of genes affected by doxorubicin are not only involved in apoptotic machinery, but also cell cycle regulation, metabolism, transcription factors, signal transduction, and protein degradation.

At supraclinical concentrations (>5 μm), doxorubicin has been found to exert a number of other effects, including but not limited to free radical generation, lipid peroxidation, DNA cross-linking, inhibition of helicase II, and degradation of telomeric DNA. Doxorubicin can also cause mitochondria to release cytochrome c, initiating caspase activation and apoptosis. In the presence of oxidoreductases, doxorubicin is reduced by one electron to a semiquinone free radical. The highly reactive intermediate reacts with oxygen to regenerate itself, producing free radical superoxide and hydrogen peroxide in the process. In the case of iron metabolism, doxorubicin creates formaldehyde, which in turn forms a conjugate (DOX-FORM), whose active metabolite forms a "virtual crosslink" with DNA. More recent studies have shown that this pathway is not necessarily dependent on iron metabolism, but that other cellular processes can induce this formaldehyde formation. Supraclinical concentrations have also produced malondialdehyde-DNA (MDA-DNA) adducts that lead to cell cycle arrest. MDA is a byproduct ROS generation and is well know for its mutagenic properties. A large number of these studies have been conducted in MCF-7 breast cancer cells, as doxorubicin has been used extensively in the treatment of breast tumors.

Resistance to doxorubicin is most commonly due to the up-regulation of a membrane-associated, energy-dependent efflux transporter that pumps out not only doxorubicin, but often other cytotoxic drugs such as vinblastine and colchicine as well. Doxorubicin-resistant cell lines are typically appended with "/ADR" after their designation, e.g. "MCF-7/ADR". The best characterized of these multidrug resistance (MDR) transporters is p-glycoprotein (pgp, ABCB1), a product of the mdr1 gene. Like all of these transporters, it has the ability to capture doxorubicin even before it can pass completely through the plasma membrane. A number of other non-pgp transporters have been identified, including the MDR-associated protein (MRP) and breast cancer related protein (BCRP, ABCG2), all of which are members of the ATP-binding cassette family.

A number of alternative delivery methods have been explored to overcome this method of resistance. Doxorubicin itself has a characteristic fluorescence (λex=488 nm, λem=595 nm) that allows it to be easily identified using flow cytometry or fluorescence microscopy. This is particularly useful when studying the uptake and retention of doxorubicin. The most commonly used and continually successful way of challenging the energy-dependent efflux has been to encapsulate the drug itself in phospholipids or polyethylene glycol (PEG), forming a liposome that depends on its lipophilicity for improved uptake into the intracellular milieu. Some efforts have also been made in the way of forming polymer-bound drugs and photodynamic therapy to alter the pH of endocytic vesicles to allow doxorubicin release into the cytoplasm.

Creation of $TiO_2$-doxorubicin Nanoconjugates

Formation of covalent bonds between $TiO_2$ and dopamine or alizarin is dependent on the presence of a bidentate functional group on the ligand. It was investigated whether doxorubicin binds to $TiO_2$ in a similar manner. Solutions of doxorubicin were combined with 6 nm $TiO_2$ nanoparticles at varying ratios. The samples were subjected to UV absorbance measurements using a Nanodrop ND-1000 Spectrophotometer (Thermo Scientific), and it was found that a ratio corresponding to approximately 35% coverage of each nanoparticle by doxorubicin had the highest change in UV absorption.

This correlated to a doxorubicin concentration of 1.72 μm and nanoparticle concentration of 0.72 μM. Additionally, upon mixing it was found that there was a change in color of the solution, distinct from free doxorubicin in the absence of nanoparticles. This change in the optical properties was taken as indicative of successful surface modification of $TiO_2$, as had been previously described.

Nanoconjugates were dialyzed in 10 mM Na2HPO4 buffer to remove any unbound doxorubicin, should any exist. After dialysis, infrared spectroscopy was done and the same "new" peaks in the nanoconjugates (DOX nanoconjugates dotted line; dopamine nanoconjugates black line) compared to the nanoparticle alone indicate stable covalent binding of doxorubicin to nanoparticles. In addition, UV-visible light absorption was found to be unchanged (compared to the absorption prior to dyalisis), indicating that all doxorubicin had been bound to open sites on the nanoparticle (FIG. 52).

Cytotoxicity

Studies of changes in cytotoxic activity of nanoconjugates versus free doxorubicin involved treatment of PC12 cells with nanoconjugates, free doxorubicin (1.72 μM), and unbound $TiO_2$ nanoparticles (0.72 μM) in $Na_2HPO_4$ buffer, and $Na_2HPO_4$ buffer (10 mM) alone. Cell media was changed and treatments added directly to new media. PC12 cells were chosen because they possess an intact p53 signaling mechanism, considered to be the major mediator by which doxorubicin exerts apoptotic effects at clinical concentrations. Cells were incubated at 37° C. for 2-4 days, until cell death was first evident via low-power optical microscope. At 4 days post-treatment, cell viability as detected by flow cytometry and DAPI staining showed a cell viability of 38.5% in nanoconjugate-treated cells, as opposed to 79.6% in cells treated with free doxorubicin.

Na2HPO4 treated cells were split into two groups, one of which was exposed to 10 Gy of ionizing radiation to ensure DNA damage and provide a positive control for the COMET assay.

Cellular Uptake

OVCAR-8 and NIH/ADR-RES cells were treated for 4 hours with either DOX alone or DOX-NP nanoconjugates. It was found that DOX conjugation to $Fe_3O_4$@$TiO_2$ nanoparticles delayed nuclear localization of DOX in the susceptible OVCAR-8 cell line. In the NIH/ADR-RES resistant model, however, conjugation of DOX to nanoparticles improved nuclear localization as compared to DOX alone (FIG. 54).

In order to determine how nanoconjugates localize within cells after uptake, MCF-7 cells were treated with nanoconjugates, free doxorubicin, and $Na_2HPO_4$ for 1 hour. Treatment with unmodified $TiO_2$ nanoparticles was omitted as they were not detectable with confocal fluorescent microscopy without alizarin surface modifications.

No signal was found in the negative control, while free doxorubicin was found to be predominantly located in the cell nucleus. Nanoconjugates were mainly localized to the cytosol.

Example 9

Targeting Cancer Cells with Nanoparticles In Vivo

Transgenic mouse prostate cancer model with the C3(1) promoter controlling expression of SV40 large T oncogene, shows onset of prostate neoplasia by 7 months of age. These mice spontaneously develop adenocarcinomas similar to the poorly differentiated variants of human prostate cancer (Maroulakou et al., Proc Natl Acad Sci USA 1994; 91: 11236-11240; Shibata et al. Toxicol Pathol. (1998) 26(1):177-82). In three animals 200 μl of 30 uM nanoparticle suspension was injected through tail vein. These $Fe_3O_4$ core-$TiO_2$ shell nanoparticles were 6 nm in size and coated with glucose. MRI contrast was obtained in the mouse prostate at 20 minutes post-injection; 24 hours post injection, prostate samples were harvested and subjected to: 1) elemental (P, Fe, Ti, Zn) mapping using X-ray fluorescence microscopy (XFM), 2) Immunohistochemistry for Ki67 as a marker of cell proliferation. A good overlap of Zn XFM signal and Ki67 IHC signal was expected because early prostate neoplasia is characterized by expression of Ki67 protein, often showing a strong relationship with Gleason grade (Bubendorf et al., HUMAN PATHOLOGY (1998) 29(9): 949-954), as well as accumulation of zinc (Cortesi et al., Prostate (2008) 68 994-1006) (FIG. 55). However, a good overlap between these two markers of neoplasia and Ti signal indicates that neoplastic prostate cells have taken up and retained significant amount of glucose coated $TiO_2$ shell nanoparticles at 24 hours after IV injection.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

What is claimed is:

1. A multifunctional nanoconjugate comprising:

a) a nanoparticle comprising a magnetic or superparamagnetic iron oxide core covered by a $TiO_2$nanoparticle shell;

b) at least one biological molecule conjugated to said nanoparticle core; and c) an imaging contrast agent conjugated to the surface of said nanoparticle, wherein said imaging contrast agent comprises PGA-1,6-hexanediamine-(Gd-DOTA)-dopamine.

2. The nanoconjugate of claim 1, wherein said nanoparticles are between 100 nm and 0.1 nm in diameter.

3. The nanoconjugate of claim 2, wherein said nanoparticles are approximately 5 nm in diameter.

4. The nanoconjugate of claim 1, wherein said biological molecule is selected from the group consisting of a nucleic acid, a peptide-nucleic acid (PNA), a peptide, a polypeptide and an antibody.

5. The nanoconjugate of claim 4, wherein said biological molecule specifically intertacts with an in vivo target.

6. The nanoconjugate of claim 4, wherein said in vivo target is a cancer marker.

7. The nanoconjugate of claim 1, wherein said nanconjugate further comprises a therapeutic agent.

8. The nanoconjugate of claim 7, wherein said therapeutic agent is selected from the group consisting of a chemotherapeutic agent and a photosensitizer agent for photodynamic therapy.

9. The nanoconjugate of claim 1, wherein said PGA-1,6-hexanediamine-(Gd-DOTA)-dopamine comprises 28 molecules of gadolinium.

10. A method of targeting an in vivo target, comprising:

contacting an organism with the nanoconjugate of claim 1 under conditions such that said nanoconjugate interacts with said in vivo target.

11. The method of claim 10, wherein said nanoparticles are between 100 nm and 0.1 nm in diameter.

12. The method of claim 11, wherein said nanoparticles are approximately 5 nm in diameter.

13. The method of claim 10, further comprising the step of visualizing said nanoconjugate in said organism.

14. The method of claim 13, wherein visualizing said imaging agent utilizes an imaging technique selected from the group consisting of X-ray imaging, computer tomography (CT) imaging, and magnetic reasonance imaging (MRI).

15. The method of claim 10, wherein said biological molecule is selected from the group consisting of a nucleic acid, a PNA, a peptide, a polypeptide and an antibody.

16. The method of claim 10, wherein said in vivo target is a cancer marker.

17. The method of claim 10, further comprising the step of destroying said in vivo target.

18. The method of claim 17, wherein the step of destroying said in vivo target comprises a technique selected from the group consisting of neutron capture therapy by said nanoconjugate or generation of reactive oxygen species by said nanoconjuqate.

19. The method of claim 17, said nanoconjugate further comprising a therapeutic agent and wherein the step of destroying said in vivo target comprises contacting said in vivo target with said therapeutic agent.

20. The method of claim 19, wherein said therapeutic agent is selected from the group consisting of a chemotherapeutic agent and a photosensitizer agent for photodynamic therapy.

* * * * *